United States Patent
Schwarz

(12) 
(10) Patent No.: US 11,458,307 B2
(45) Date of Patent: Oct. 4, 2022

(54) SYSTEMS AND METHODS FOR TISSUE TREATMENT

(71) Applicant: BTL Healthcare Technologies a.s., Prague (CZ)

(72) Inventor: Tomás Schwarz, Prague (CZ)

(73) Assignee: BTL Healthcare Technologies A.S., Prague (CZ)

( * ) Notice: Subject to any disclaimer, the term of this patent is extended or adjusted under 35 U.S.C. 154(b) by 0 days.

(21) Appl. No.: 16/727,458

(22) Filed: Dec. 26, 2019

(65) Prior Publication Data

US 2020/0129759 A1    Apr. 30, 2020

Related U.S. Application Data

(63) Continuation of application No. 15/603,162, filed on May 23, 2017, now Pat. No. 10,583,287.

(Continued)

(51) Int. Cl.
*A61N 1/32* (2006.01)
*A61N 1/36* (2006.01)
(Continued)

(52) U.S. Cl.
CPC ......... *A61N 1/328* (2013.01); *A61N 1/36003* (2013.01); *A61N 1/36021* (2013.01);
(Continued)

(58) Field of Classification Search
CPC ................ A61N 1/328; A61N 1/36003; A61N 1/36021; A61N 1/40; A61N 2005/0644;
(Continued)

(56) References Cited

U.S. PATENT DOCUMENTS

| 1,973,387 A | 9/1934 | Neymann |
| 2,021,676 A | 11/1935 | Wood |

(Continued)

FOREIGN PATENT DOCUMENTS

| AU | 747678 B2 | 5/2002 |
| AU | 2011265424 B2 | 7/2014 |

(Continued)

OTHER PUBLICATIONS

Mekawy et al., Influence of Electro-lipolysis on Lipid Profile and Central Obesity in Obese Premenopausal Women, Bull. Fac. Ph. Th. Cairo Univ., vol. 17, No. (1) Jan. 2012 pp. 59-68.

(Continued)

*Primary Examiner* — George Manuel
(74) *Attorney, Agent, or Firm* — Sterne, Kessler, Goldstein & Fox P.L.L.C.

(57) ABSTRACT

A method for aesthetic soft tissue treatment includes placing at least one applicator in contact with the patient's body. The applicator has at least one electrode. Electrotherapy and radio frequency therapy are provided to the soft tissue, optionally with overlay or sequentially. A handheld applicator may be used, with the applicator moving during the therapy, which may provide muscle stimulation in the patient, or provide an analgesic effect during the treatment. A spacing object may be positioned between the skin of the patient and the applicator.

20 Claims, 3 Drawing Sheets

Related U.S. Application Data

(60) Provisional application No. 62/340,398, filed on May 23, 2016.

(51) Int. Cl.
  *A61N 1/40* (2006.01)
  *A61N 7/00* (2006.01)
  *A61N 5/06* (2006.01)

(52) U.S. Cl.
  CPC ............. *A61N 1/40* (2013.01); *A61N 7/00* (2013.01); *A61N 5/0616* (2013.01); *A61N 2005/0644* (2013.01); *A61N 2007/0034* (2013.01)

(58) Field of Classification Search
  CPC . A61N 2007/0034; A61N 5/0616; A61N 7/00
  See application file for complete search history.

(56) References Cited

U.S. PATENT DOCUMENTS

| | | |
|---|---|---|
| 3,163,161 A | 12/1964 | Courtin |
| 3,566,877 A | 3/1971 | Smith |
| 3,658,051 A | 4/1972 | MacLean |
| 3,841,306 A | 10/1974 | Hallgren |
| 3,915,151 A | 10/1975 | Kraus |
| 3,946,349 A | 3/1976 | Haldeman, III |
| 3,952,751 A | 4/1976 | Yarger |
| 3,971,387 A | 7/1976 | Mantell |
| 4,068,292 A | 1/1978 | Berry |
| 4,143,661 A | 3/1979 | Laforge |
| 4,197,851 A | 4/1980 | Fellus |
| 4,237,898 A | 12/1980 | Whalley |
| 4,305,115 A | 12/1981 | Armitage |
| 4,315,503 A | 2/1982 | Ryaby |
| 4,392,040 A | 7/1983 | Rand |
| 4,454,883 A | 6/1984 | Fellus |
| 4,456,001 A | 6/1984 | Pescatore |
| 4,550,714 A | 11/1985 | Talish |
| 4,556,056 A | 12/1985 | Fischer et al. |
| 4,665,898 A | 5/1987 | Costa |
| 4,674,482 A | 6/1987 | Waltonen |
| 4,674,505 A | 6/1987 | Pauli |
| 4,723,536 A | 2/1988 | Rauscher |
| 4,850,959 A | 7/1989 | Findl |
| 4,889,526 A | 12/1989 | Rauscher |
| 4,957,480 A | 9/1990 | Morenings |
| 4,989,604 A | 2/1991 | Fang |
| 4,993,413 A | 2/1991 | McLeod |
| 5,061,234 A | 10/1991 | Chaney |
| 5,067,940 A | 11/1991 | Liboff |
| 5,085,626 A | 2/1992 | Frey |
| 5,143,063 A | 9/1992 | Fellner |
| 5,156,587 A | 10/1992 | Montone |
| 5,181,902 A | 1/1993 | Erickson |
| 5,199,951 A | 4/1993 | Spears |
| 5,334,181 A | 8/1994 | Rubinsky |
| 5,344,384 A | 9/1994 | Ostrow |
| 5,401,233 A | 3/1995 | Erickson |
| 5,415,617 A | 5/1995 | Kraus |
| 5,419,344 A | 5/1995 | Dewitt |
| 5,433,737 A | 7/1995 | Aimone |
| 5,433,740 A | 7/1995 | Yamaguchi |
| 5,584,863 A | 12/1996 | Rauch |
| 5,620,463 A | 4/1997 | Drolet |
| 5,660,836 A | 8/1997 | Knowlton |
| 5,674,218 A | 10/1997 | Rubinsky |
| 5,690,692 A | 11/1997 | Fleming |
| 5,691,873 A | 11/1997 | Masaki |
| 5,718,662 A | 2/1998 | Jalinous |
| 5,725,471 A | 3/1998 | Davey |
| 5,755,753 A | 5/1998 | Knowlton |
| 5,766,124 A | 6/1998 | Polson |
| 5,782,743 A | 7/1998 | Russell |
| 5,807,232 A | 9/1998 | Espinoza |
| 5,857,957 A | 1/1999 | Lin |
| 5,908,444 A | 6/1999 | Azure |
| 5,919,219 A | 7/1999 | Knowlton |
| 5,968,527 A | 10/1999 | Litovitz |
| 5,984,854 A | 11/1999 | Ishikawa |
| 6,017,337 A | 1/2000 | Pira |
| 6,032,675 A | 3/2000 | Rubinsky |
| 6,038,485 A | 3/2000 | Axelgaard |
| 6,047,215 A | 4/2000 | McClure |
| 6,063,108 A | 5/2000 | Salansky |
| 6,067,474 A | 5/2000 | Schulman |
| 6,086,525 A | 7/2000 | Davey |
| 6,094,599 A | 7/2000 | Bingham |
| 6,099,459 A | 8/2000 | Jacobson |
| 6,099,523 A | 8/2000 | Kim |
| 6,117,066 A | 9/2000 | Abrams |
| 6,132,361 A | 10/2000 | Epstein |
| 6,141,985 A | 11/2000 | Cluzeau |
| 6,155,966 A | 12/2000 | Parker |
| 6,161,757 A | 12/2000 | Morris |
| 6,179,769 B1 | 1/2001 | Ishikawa |
| 6,179,770 B1 | 1/2001 | Mould |
| 6,179,771 B1 | 1/2001 | Mueller |
| 6,213,933 B1 | 4/2001 | Lin |
| 6,223,750 B1 | 5/2001 | Ishikawa |
| 6,246,905 B1 | 6/2001 | Mogul |
| 6,255,815 B1 | 7/2001 | Davey |
| 6,261,301 B1 | 7/2001 | Knesch |
| 6,273,862 B1 | 8/2001 | Privitera |
| 6,273,884 B1 | 8/2001 | Altshuler |
| 6,280,376 B1 | 8/2001 | Holcomb |
| 6,282,448 B1 | 8/2001 | Katz |
| D447,806 S | 9/2001 | Davey |
| 6,311,090 B1 | 10/2001 | Knowlton |
| 6,324,430 B1 | 11/2001 | Zarinetchi |
| 6,324,432 B1 | 11/2001 | Rigaux |
| 6,334,069 B1 | 12/2001 | George |
| 6,334,074 B1 | 12/2001 | Spertell |
| 6,350,276 B1 | 2/2002 | Knowlton |
| 6,402,678 B1 | 6/2002 | Fischell |
| 6,413,255 B1 | 7/2002 | Stern |
| 6,418,345 B1 | 7/2002 | Tepper |
| 6,424,864 B1 | 7/2002 | Matsuura |
| 6,425,852 B1 | 7/2002 | Epstein |
| 6,443,883 B1 | 9/2002 | Ostrow |
| 6,445,955 B1 | 9/2002 | Michelson et al. |
| 6,447,440 B1 | 9/2002 | Markoll |
| 6,453,202 B1 | 9/2002 | Knowlton |
| 6,461,375 B1 | 10/2002 | Baudry |
| 6,491,620 B1 | 12/2002 | Davey |
| 6,500,110 B1 | 12/2002 | Davey |
| 6,520,903 B1 | 2/2003 | Yamashiro |
| 6,527,694 B1 | 3/2003 | Ishikawa |
| 6,527,695 B1 | 3/2003 | Davey |
| 6,537,197 B1 | 3/2003 | Ruohonen |
| 6,569,078 B2 | 5/2003 | Ishikawa |
| 6,605,080 B1 | 8/2003 | Altshuler |
| 6,635,053 B1 | 10/2003 | Lalonde |
| 6,658,301 B2 | 12/2003 | Loeb |
| 6,662,054 B2 | 12/2003 | Kreindel |
| 6,663,556 B2 | 12/2003 | Barker |
| 6,663,659 B2 | 12/2003 | McDaniel |
| 6,701,185 B2 | 3/2004 | Burnett |
| 6,735,481 B1 | 5/2004 | Bingham |
| 6,738,667 B2 | 5/2004 | Deno |
| 6,749,624 B2 | 6/2004 | Knowlton |
| 6,827,681 B2 | 12/2004 | Tanner |
| 6,849,040 B2 | 2/2005 | Ruohonen |
| 6,860,852 B2 | 3/2005 | Klaus |
| 6,871,099 B1 | 3/2005 | Whitehurst |
| 6,879,859 B1 | 4/2005 | Boveja |
| 6,889,090 B2 | 5/2005 | Kreindel |
| 6,920,883 B2 | 7/2005 | Bessette |
| 6,939,287 B1 | 9/2005 | Ardizzone |
| 6,960,202 B2 | 11/2005 | Cluzeau |
| 6,990,427 B2 | 1/2006 | Kirsch et al. |
| 7,024,239 B2 | 4/2006 | George |
| 7,030,764 B2 | 4/2006 | Smith |
| 7,041,100 B2 | 5/2006 | Kreindel |

(56) References Cited

U.S. PATENT DOCUMENTS

| | | |
|---|---|---|
| 7,083,580 B2 | 8/2006 | Bernabei |
| 7,186,209 B2 | 3/2007 | Jacobson |
| 7,217,265 B2 | 5/2007 | Hennings |
| 7,276,058 B2 | 10/2007 | Altshuler |
| 7,309,309 B2 | 12/2007 | Wang |
| 7,318,821 B2 | 1/2008 | Lalonde |
| 7,351,252 B2 | 4/2008 | Altshuler |
| 7,367,341 B2 | 5/2008 | Anderson |
| 7,369,895 B2 | 5/2008 | Hurtado |
| 7,372,271 B2 | 5/2008 | Roozen |
| 7,376,460 B2 | 5/2008 | Bernabei |
| 7,396,326 B2 | 7/2008 | Ghiron |
| 7,496,401 B2 | 2/2009 | Bernabei |
| 7,520,849 B1 | 4/2009 | Simon |
| 7,520,875 B2 | 4/2009 | Bernabei |
| 7,532,926 B2 | 5/2009 | Bernabei |
| 7,571,003 B2 | 8/2009 | Pozzato |
| 7,591,776 B2 | 9/2009 | Phillips |
| 7,601,115 B2 | 10/2009 | Riehl |
| 7,608,035 B2 | 10/2009 | Farone |
| 7,618,429 B2 | 11/2009 | Mulholland |
| 7,630,774 B2 | 12/2009 | Karni |
| 7,643,883 B2 | 1/2010 | Kreindel |
| 7,697,998 B2 | 4/2010 | Axelgaard |
| 7,699,768 B2 | 4/2010 | Kishawi et al. |
| 7,740,574 B2 | 6/2010 | Pilla |
| 7,744,523 B2 | 6/2010 | Epstein |
| 7,783,348 B2 | 8/2010 | Gill |
| 7,785,358 B2 | 8/2010 | Lach |
| 7,854,754 B2 | 12/2010 | Ting |
| 7,909,786 B2 | 3/2011 | Bonnefin |
| 7,914,469 B2 | 3/2011 | Torbati |
| 7,945,321 B2 | 5/2011 | Bernabei |
| 7,946,973 B2 | 5/2011 | Peterchev |
| 7,953,500 B2 | 5/2011 | Bingham |
| 7,998,053 B2 | 8/2011 | Aho |
| 8,035,385 B2 | 10/2011 | Tomiha |
| RE43,007 E | 12/2011 | Lalonde |
| 8,088,058 B2 | 1/2012 | Juliana |
| 8,128,549 B2 | 3/2012 | Testani |
| 8,133,191 B2 | 3/2012 | Rosenberg |
| 8,137,258 B1 | 3/2012 | Dennis |
| 8,172,835 B2 | 5/2012 | Leyh |
| 8,192,474 B2 | 6/2012 | Levinson |
| 8,204,446 B2 | 6/2012 | Scheer |
| 8,251,986 B2 | 8/2012 | Chornenky |
| 8,265,763 B2 | 9/2012 | Fahey |
| 8,271,090 B1 | 9/2012 | Hartman et al. |
| 8,275,442 B2 | 9/2012 | Allison |
| 8,285,390 B2 | 10/2012 | Levinson |
| 8,335,566 B2 | 12/2012 | Mueller |
| 8,337,539 B2 | 12/2012 | Ting |
| 8,366,756 B2 | 2/2013 | Tucek |
| 8,376,825 B2 | 2/2013 | Guinn |
| 8,376,925 B1 | 2/2013 | Dennis |
| 8,454,591 B2 | 6/2013 | Leyh |
| 8,457,751 B2 | 6/2013 | Pozzato |
| 8,475,354 B2 | 7/2013 | Phillips et al. |
| 8,523,927 B2 | 9/2013 | Levinson |
| 8,548,599 B2 | 10/2013 | Zarsky |
| 8,565,888 B2 | 10/2013 | Buhlmann |
| 8,579,953 B1 | 11/2013 | Dunbar |
| 8,588,930 B2 | 11/2013 | DiUbaldi et al. |
| 8,593,245 B2 | 11/2013 | Zeng |
| 8,603,073 B2 | 12/2013 | Allison |
| 8,646,239 B2 | 2/2014 | Rulon |
| 8,666,492 B2 | 3/2014 | Muller |
| 8,676,338 B2 | 3/2014 | Levinson |
| 8,684,901 B1 | 4/2014 | Zabara |
| 8,700,176 B2 | 4/2014 | Azar |
| 8,702,774 B2 | 4/2014 | Baker |
| 8,725,270 B2 | 5/2014 | Towe |
| 8,771,326 B2 | 7/2014 | Myeong |
| 8,788,060 B2 | 7/2014 | Nebrigic et al. |
| 8,795,148 B2 | 8/2014 | Schneider et al. |
| 8,834,547 B2 | 9/2014 | Anderson |
| 8,840,608 B2 | 9/2014 | Anderson |
| 8,864,641 B2 | 10/2014 | Riehl et al. |
| 8,868,177 B2 | 10/2014 | Simon |
| 8,906,009 B2 | 12/2014 | Nebrigic |
| 8,915,948 B2 | 12/2014 | Altshuler |
| 8,932,338 B2 | 1/2015 | Lim |
| 8,979,727 B2 | 3/2015 | Ron Edoute |
| 8,985,331 B2 | 3/2015 | Guenter et al. |
| 8,998,791 B2 | 4/2015 | Ron Edoute |
| 9,002,477 B2 | 4/2015 | Burnett |
| 9,028,469 B2 | 5/2015 | Jones |
| 9,037,247 B2 | 5/2015 | Simon |
| 9,044,595 B2 | 6/2015 | Araya |
| 9,061,128 B2 | 6/2015 | Hall |
| 9,072,891 B1 | 7/2015 | Rao |
| 9,078,634 B2 | 7/2015 | Gonzales |
| 9,089,719 B2 | 7/2015 | Simon |
| 9,101,524 B2 | 8/2015 | Aghion |
| 9,132,031 B2 | 9/2015 | Levinson |
| 9,149,650 B2 | 10/2015 | Shanks |
| 9,168,096 B2 | 10/2015 | Kreindel |
| 9,233,257 B1 | 1/2016 | Zabara |
| 9,254,395 B1 | 2/2016 | Shambayati |
| 9,261,574 B2 | 2/2016 | Boskamp |
| 9,265,690 B2 | 2/2016 | Kriksunov |
| 9,308,120 B2 | 4/2016 | Anderson |
| 9,314,368 B2 | 4/2016 | Allison |
| 9,326,910 B2 | 5/2016 | Eckhouse |
| 9,339,641 B2 | 5/2016 | Rajguru |
| 9,358,068 B2 | 6/2016 | Schomacker |
| 9,358,149 B2 | 6/2016 | Anderson |
| 9,375,345 B2 | 6/2016 | Levinson |
| 9,387,339 B2 | 7/2016 | Sham |
| 9,398,975 B2 | 7/2016 | Müller |
| 9,408,745 B2 | 8/2016 | Levinson |
| 9,414,759 B2 | 8/2016 | Lang |
| 9,433,797 B2 | 9/2016 | Pilla |
| 9,439,805 B2 | 9/2016 | Gonzales |
| 9,446,258 B1 | 9/2016 | Schwarz |
| 9,468,774 B2 | 10/2016 | Zárský |
| 9,532,832 B2 | 1/2017 | Ron Edoute |
| 9,545,523 B2 | 1/2017 | Nanda |
| 9,561,357 B2 | 2/2017 | Hall |
| 9,586,057 B2 | 3/2017 | Ladman |
| 9,596,920 B2 | 3/2017 | Shalev |
| 9,610,429 B2 | 4/2017 | Harris |
| 9,610,459 B2 | 4/2017 | Burnett |
| 9,615,854 B2 | 4/2017 | Matsushita |
| 9,636,516 B2 | 5/2017 | Schwarz |
| 9,636,519 B2 | 5/2017 | Ladman |
| 9,649,220 B2 | 5/2017 | Anderson |
| 9,655,770 B2 | 5/2017 | Levinson |
| 9,694,194 B2 | 7/2017 | Ron Edoute |
| 9,737,238 B2 | 8/2017 | Wright et al. |
| 9,737,434 B2 | 8/2017 | Allison |
| 9,757,584 B2 | 9/2017 | Burnett |
| 9,782,324 B2 | 10/2017 | Crunick |
| 9,814,897 B2 | 11/2017 | Ron Edoute |
| 9,844,460 B2 | 12/2017 | Weber |
| 9,844,461 B2 | 12/2017 | Levinson |
| 9,855,166 B2 | 1/2018 | Anderson |
| 9,861,421 B2 | 1/2018 | O'Neil |
| 9,861,520 B2 | 1/2018 | Baker |
| 9,867,996 B2 | 1/2018 | Zarsky |
| 9,901,743 B2 | 2/2018 | Ron Edoute |
| 9,919,161 B2 | 3/2018 | Schwarz |
| 9,937,358 B2 | 4/2018 | Schwarz |
| 9,962,553 B2 | 5/2018 | Schwarz |
| 9,968,797 B2 | 5/2018 | Sham |
| 9,974,519 B1 | 5/2018 | Schwarz |
| 9,974,684 B2 | 5/2018 | Anderson |
| 9,980,765 B2 | 5/2018 | Avram |
| 9,981,143 B2 | 5/2018 | Ron Edoute |
| 9,999,780 B2 | 6/2018 | Weyh |
| 10,037,867 B2 | 7/2018 | Godyak |
| 10,039,929 B1 | 8/2018 | Schwarz |
| 10,080,906 B2 | 9/2018 | Schwarz |
| 10,092,346 B2 | 10/2018 | Levinson |

(56) References Cited

U.S. PATENT DOCUMENTS

| | | |
|---|---|---|
| 10,111,770 B2 | 10/2018 | Harris |
| 10,111,774 B2 | 10/2018 | Gonzales |
| 10,124,187 B2 | 11/2018 | Schwarz |
| 10,183,172 B2 | 1/2019 | Ghiron |
| 10,195,453 B2 | 2/2019 | Schwarz |
| 10,195,454 B2 | 2/2019 | Yamashiro |
| 10,201,380 B2 | 2/2019 | Debenedictis |
| 10,245,439 B1 | 4/2019 | Schwarz |
| 10,271,900 B2 | 4/2019 | Marchitto |
| 10,342,988 B2 | 7/2019 | Midorikawa |
| 10,413,745 B2 | 9/2019 | Riehl |
| 10,463,869 B2 | 11/2019 | Ron Edoute |
| 10,471,269 B1 | 11/2019 | Schwarz |
| 10,478,588 B2 | 11/2019 | Walpole |
| 10,478,633 B2 | 11/2019 | Schwarz |
| 10,478,634 B2 | 11/2019 | Schwarz |
| 10,493,293 B2 | 12/2019 | Schwarz |
| 10,518,098 B2 | 12/2019 | Hong |
| 10,549,109 B2 | 2/2020 | Schwarz |
| 10,549,110 B1 | 2/2020 | Schwarz |
| 10,556,121 B2 | 2/2020 | Gurfein |
| 10,556,122 B1 | 2/2020 | Schwarz |
| 10,569,094 B2 | 2/2020 | Schwarz |
| 10,569,095 B1 | 2/2020 | Schwarz |
| 10,583,287 B2 | 3/2020 | Schwarz |
| 10,596,386 B2 | 3/2020 | Schwarz |
| 10,610,696 B1 | 4/2020 | Peled |
| 10,632,321 B2 | 4/2020 | Schwarz |
| 10,639,490 B2 | 5/2020 | Simon |
| 10,661,093 B2 | 5/2020 | Ron Edoute |
| 10,675,819 B2 | 6/2020 | Li |
| 10,688,310 B2 | 6/2020 | Schwarz |
| 10,695,575 B1 | 6/2020 | Schwarz |
| 10,695,576 B2 | 6/2020 | Schwarz |
| 10,709,894 B2 | 7/2020 | Schwarz |
| 10,709,895 B2 | 7/2020 | Schwarz |
| 10,806,943 B2 | 10/2020 | Sokolowski |
| 10,821,295 B1 | 11/2020 | Schwarz |
| 10,849,784 B2 | 12/2020 | Jurna et al. |
| 2001/0018547 A1 | 8/2001 | Mechlenburg et al. |
| 2001/0031906 A1 | 10/2001 | Ishikawa |
| 2002/0010414 A1 | 1/2002 | Coston |
| 2002/0049483 A1 | 4/2002 | Knowlton |
| 2002/0082466 A1 | 6/2002 | Han |
| 2002/0128686 A1 | 9/2002 | Minogue et al. |
| 2002/0143365 A1 | 10/2002 | Herbst |
| 2002/0160436 A1 | 10/2002 | Markov |
| 2002/0165590 A1 | 11/2002 | Crowe |
| 2003/0028072 A1 | 2/2003 | Fischell |
| 2003/0032900 A1 | 2/2003 | Ella |
| 2003/0032950 A1 | 2/2003 | Altshuler |
| 2003/0050527 A1 | 3/2003 | Fox |
| 2003/0074037 A1 | 4/2003 | Moore |
| 2003/0078646 A1 | 4/2003 | Axelgaard |
| 2003/0093133 A1 | 5/2003 | Crowe et al. |
| 2003/0130711 A1 | 7/2003 | Pearson |
| 2003/0149451 A1 | 8/2003 | Chomenky |
| 2003/0153958 A1 | 8/2003 | Yamazaki |
| 2003/0158585 A1 | 8/2003 | Burnett |
| 2003/0216729 A1 | 11/2003 | Marchitto et al. |
| 2003/0220674 A1 | 11/2003 | Anderson |
| 2003/0236487 A1 | 12/2003 | Knowlton |
| 2004/0015163 A1 | 1/2004 | Buysse |
| 2004/0034346 A1 | 2/2004 | Stern et al. |
| 2004/0039279 A1 | 2/2004 | Ruohonen |
| 2004/0073079 A1 | 4/2004 | Altshuler |
| 2004/0077977 A1 | 4/2004 | Ella et al. |
| 2004/0093042 A1 | 5/2004 | Altshuler |
| 2004/0102768 A1 | 5/2004 | Cluzeau |
| 2004/0162583 A1 | 8/2004 | Bingham |
| 2004/0193003 A1 | 9/2004 | Mechlenburg |
| 2004/0206365 A1 | 10/2004 | Knowlton |
| 2004/0210214 A1 | 10/2004 | Knowlton |
| 2004/0210282 A1 | 10/2004 | Flock et al. |
| 2004/0210287 A1 | 10/2004 | Greene |
| 2004/0230226 A1 | 11/2004 | Bingham |
| 2005/0038313 A1 | 2/2005 | Ardizzone |
| 2005/0049543 A1 | 3/2005 | Anderson |
| 2005/0075701 A1 | 4/2005 | Shafer |
| 2005/0075702 A1 | 4/2005 | Shafer |
| 2005/0090814 A1 | 4/2005 | Lalonde |
| 2005/0107656 A1 | 5/2005 | Jang et al. |
| 2005/0134193 A1 | 6/2005 | Myers |
| 2005/0187599 A1 | 8/2005 | Sharkey et al. |
| 2005/0203504 A1 | 9/2005 | Wham |
| 2005/0215987 A1 | 9/2005 | Slatkine |
| 2005/0216062 A1 | 9/2005 | Herbst |
| 2005/0251120 A1 | 11/2005 | Anderson |
| 2006/0004244 A1 | 1/2006 | Phillips |
| 2006/0020236 A1 | 1/2006 | Ben-Nun |
| 2006/0036300 A1 | 2/2006 | Kreindel |
| 2006/0094924 A1 | 5/2006 | Riehl |
| 2006/0106375 A1 | 5/2006 | Werneth |
| 2006/0152301 A1 | 7/2006 | Rohwedder |
| 2006/0184214 A1 | 8/2006 | McDaniel |
| 2006/0187607 A1 | 8/2006 | Mo |
| 2006/0195168 A1 | 8/2006 | Dunbar |
| 2006/0199992 A1 | 9/2006 | Eisenberg |
| 2006/0206103 A1 | 9/2006 | Altshuler |
| 2006/0206180 A1 | 9/2006 | Alcidi |
| 2006/0253176 A1 | 11/2006 | Caruso |
| 2006/0259102 A1 | 11/2006 | Slatkine |
| 2006/0271028 A1 | 11/2006 | Altshuler |
| 2006/0287566 A1 | 12/2006 | Zangen |
| 2006/0293719 A1 | 12/2006 | Naghavi |
| 2007/0010766 A1 | 1/2007 | Gil |
| 2007/0010861 A1 | 1/2007 | Anderson |
| 2007/0016274 A1 | 1/2007 | Boveja et al. |
| 2007/0027411 A1 | 2/2007 | Ella et al. |
| 2007/0083237 A1 | 4/2007 | Teruel |
| 2007/0088413 A1 | 4/2007 | Weber |
| 2007/0088419 A1 | 4/2007 | Fiorina et al. |
| 2007/0135811 A1 | 6/2007 | Hooven |
| 2007/0142886 A1 | 6/2007 | Fischell et al. |
| 2007/0173749 A1 | 7/2007 | Williams |
| 2007/0173805 A1 | 7/2007 | Weinberg |
| 2007/0179534 A1 | 8/2007 | Firlik et al. |
| 2007/0198071 A1 | 8/2007 | Ting |
| 2007/0232966 A1 | 10/2007 | Applebaum |
| 2007/0244530 A1 | 10/2007 | Ren |
| 2007/0255355 A1 | 11/2007 | Altshuler |
| 2007/0255362 A1 | 11/2007 | Levinson |
| 2007/0260107 A1 | 11/2007 | Mishelevich |
| 2007/0270795 A1 | 11/2007 | Francischelli |
| 2007/0270925 A1 | 11/2007 | Levinson |
| 2007/0282156 A1 | 12/2007 | Konings |
| 2007/0293911 A1 | 12/2007 | Crowe |
| 2007/0293918 A1 | 12/2007 | Thompson et al. |
| 2008/0009885 A1 | 1/2008 | Del Giglio |
| 2008/0046053 A1 | 2/2008 | Wagner et al. |
| 2008/0077201 A1 | 3/2008 | Levinson |
| 2008/0077202 A1 | 3/2008 | Levinson |
| 2008/0077211 A1 | 3/2008 | Levinson |
| 2008/0082094 A1 | 4/2008 | McPherson |
| 2008/0082153 A1 | 4/2008 | Gadsby et al. |
| 2008/0103565 A1 | 5/2008 | Altshuler |
| 2008/0132971 A1 | 6/2008 | Pille |
| 2008/0183251 A1 | 7/2008 | Azar |
| 2008/0188915 A1 | 8/2008 | Mills |
| 2008/0228520 A1 | 9/2008 | Day |
| 2008/0234534 A1 | 9/2008 | Mikas |
| 2008/0249350 A1 | 10/2008 | Marchitto |
| 2008/0255572 A1 | 10/2008 | Zeller |
| 2008/0255637 A1 | 10/2008 | Oishi |
| 2008/0262287 A1 | 10/2008 | Dussau |
| 2008/0262574 A1 | 10/2008 | Briefs |
| 2008/0287839 A1 | 11/2008 | Rosen |
| 2008/0287948 A1 | 11/2008 | Newton |
| 2008/0306325 A1 | 12/2008 | Burnett |
| 2008/0306326 A1 | 12/2008 | Epstein |
| 2008/0312647 A1 | 12/2008 | Knopp |
| 2009/0005631 A1 | 1/2009 | Simenhaus |
| 2009/0018384 A1 | 1/2009 | Boyden |
| 2009/0018623 A1 | 1/2009 | Levinson |

(56) References Cited

U.S. PATENT DOCUMENTS

| | | |
|---|---|---|
| 2009/0018624 A1 | 1/2009 | Levinson |
| 2009/0018625 A1 | 1/2009 | Levinson |
| 2009/0018626 A1 | 1/2009 | Levinson |
| 2009/0018627 A1 | 1/2009 | Levinson |
| 2009/0018628 A1 | 1/2009 | Burns |
| 2009/0024192 A1 | 1/2009 | Mulholland |
| 2009/0024193 A1 | 1/2009 | Altshuler |
| 2009/0036958 A1 | 2/2009 | Mehta |
| 2009/0043293 A1 | 2/2009 | Pankratov |
| 2009/0099405 A1 | 4/2009 | Schneider et al. |
| 2009/0108969 A1 | 4/2009 | Sims |
| 2009/0118722 A1 | 5/2009 | Ebbers |
| 2009/0118790 A1 | 5/2009 | Van Herk |
| 2009/0149300 A1 | 6/2009 | Chen |
| 2009/0149929 A1 | 6/2009 | Levinson |
| 2009/0149930 A1 | 6/2009 | Schenck |
| 2009/0156958 A1* | 6/2009 | Mehta .................. A61B 18/203 600/549 |
| 2009/0221938 A1 | 9/2009 | Rosenberg |
| 2009/0227831 A1 | 9/2009 | Burnett |
| 2009/0234423 A1 | 9/2009 | Vetanze |
| 2009/0248004 A1 | 10/2009 | Altshuler |
| 2009/0254154 A1 | 10/2009 | De Taboada |
| 2009/0270945 A1 | 10/2009 | Markoll et al. |
| 2009/0284339 A1 | 11/2009 | Choi |
| 2009/0306648 A1 | 12/2009 | Podhajsky |
| 2009/0326571 A1 | 12/2009 | Mulholland |
| 2010/0004536 A1 | 1/2010 | Rosenberg |
| 2010/0004715 A1 | 1/2010 | Fahey |
| 2010/0016761 A1 | 1/2010 | Rosenberg |
| 2010/0036191 A1 | 2/2010 | Walter et al. |
| 2010/0036368 A1 | 2/2010 | England |
| 2010/0049188 A1* | 2/2010 | Nelson ............... A61B 18/1206 606/34 |
| 2010/0069704 A1 | 3/2010 | Peterchev |
| 2010/0081971 A1 | 4/2010 | Allison |
| 2010/0087699 A1 | 4/2010 | Peterchev |
| 2010/0087816 A1 | 4/2010 | Roy |
| 2010/0121131 A1 | 5/2010 | Mathes |
| 2010/0130945 A1 | 5/2010 | Laniado |
| 2010/0145399 A1 | 6/2010 | Johari |
| 2010/0152522 A1 | 6/2010 | Roth |
| 2010/0152824 A1 | 6/2010 | Allison |
| 2010/0160712 A1 | 6/2010 | Burnett |
| 2010/0168501 A1 | 7/2010 | Burnett |
| 2010/0179372 A1 | 7/2010 | Glassman |
| 2010/0185042 A1 | 7/2010 | Schneider et al. |
| 2010/0217253 A1 | 8/2010 | Mehta |
| 2010/0222629 A1 | 9/2010 | Burnett |
| 2010/0228250 A1 | 9/2010 | Brogna |
| 2010/0256438 A1 | 10/2010 | Mishelevich et al. |
| 2010/0256439 A1 | 10/2010 | Schneider et al. |
| 2010/0261992 A1 | 10/2010 | Axelgaard |
| 2010/0274327 A1 | 10/2010 | Carroll et al. |
| 2010/0274329 A1 | 10/2010 | Bradley |
| 2010/0280582 A1 | 11/2010 | Baker |
| 2010/0286470 A1 | 11/2010 | Schneider et al. |
| 2010/0286691 A1 | 11/2010 | Kerr |
| 2010/0298623 A1 | 11/2010 | Mishelevich et al. |
| 2010/0309689 A1 | 12/2010 | Coulson |
| 2010/0324611 A1 | 12/2010 | Deming |
| 2010/0331602 A1 | 12/2010 | Mishelevich et al. |
| 2010/0331603 A1 | 12/2010 | Szecsi |
| 2011/0004261 A1 | 1/2011 | Sham |
| 2011/0007745 A1 | 1/2011 | Schultz |
| 2011/0009737 A1 | 1/2011 | Manstein |
| 2011/0015464 A1 | 1/2011 | Riehl |
| 2011/0021863 A1 | 1/2011 | Burnett |
| 2011/0046432 A1 | 2/2011 | Simon |
| 2011/0046523 A1 | 2/2011 | Altshuler |
| 2011/0066216 A1 | 3/2011 | Ting |
| 2011/0077451 A1 | 3/2011 | Marchitto |
| 2011/0082383 A1* | 4/2011 | Cory .................. A61B 5/0536 600/547 |
| 2011/0087312 A1 | 4/2011 | Shanks |
| 2011/0105826 A1 | 5/2011 | Mishelevich et al. |
| 2011/0112520 A1 | 5/2011 | Michael |
| 2011/0118722 A1 | 5/2011 | Lischinsky et al. |
| 2011/0125203 A1 | 5/2011 | Simon |
| 2011/0130618 A1 | 6/2011 | Ron Edoute |
| 2011/0130713 A1 | 6/2011 | Dufay |
| 2011/0130796 A1 | 6/2011 | Louise |
| 2011/0152967 A1 | 6/2011 | Simon |
| 2011/0172735 A1 | 7/2011 | Johari |
| 2011/0172752 A1 | 7/2011 | Bingham |
| 2011/0190569 A1 | 8/2011 | Simon |
| 2011/0196438 A1 | 8/2011 | Mnozil et al. |
| 2011/0202058 A1 | 8/2011 | Eder |
| 2011/0218464 A1 | 9/2011 | Iger |
| 2011/0224761 A1 | 9/2011 | Manstein |
| 2011/0237921 A1 | 9/2011 | Askin, III et al. |
| 2011/0238050 A1 | 9/2011 | Allison |
| 2011/0238051 A1 | 9/2011 | Levinson |
| 2011/0245900 A1 | 10/2011 | Turner |
| 2011/0263925 A1 | 10/2011 | Bratton |
| 2011/0273251 A1 | 11/2011 | Mishelevich et al. |
| 2011/0275927 A1 | 11/2011 | Wagner et al. |
| 2011/0276108 A1 | 11/2011 | Crowe et al. |
| 2011/0300079 A1 | 12/2011 | Martens |
| 2011/0306943 A1 | 12/2011 | Dunbar |
| 2011/0319700 A1 | 12/2011 | Schneider |
| 2012/0016359 A1 | 1/2012 | Podhajsky |
| 2012/0022518 A1 | 1/2012 | Levinson |
| 2012/0029394 A1 | 2/2012 | Babaev |
| 2012/0035608 A1 | 2/2012 | Marchitto et al. |
| 2012/0046598 A1 | 2/2012 | Kardos |
| 2012/0046653 A1 | 2/2012 | Welches |
| 2012/0053449 A1 | 3/2012 | Moses |
| 2012/0101326 A1 | 4/2012 | Simon et al. |
| 2012/0108883 A1 | 5/2012 | Peterchev |
| 2012/0108884 A1 | 5/2012 | Bechler |
| 2012/0109241 A1 | 5/2012 | Rauscher |
| 2012/0116271 A1 | 5/2012 | Caruso |
| 2012/0150079 A1 | 6/2012 | Rosenberg |
| 2012/0157747 A1 | 6/2012 | Rybski |
| 2012/0158100 A1 | 6/2012 | Schomacker |
| 2012/0172653 A1 | 7/2012 | Chornenky |
| 2012/0197361 A1 | 8/2012 | Gonzales |
| 2012/0215210 A1 | 8/2012 | Brown |
| 2012/0226272 A1 | 9/2012 | Chernov |
| 2012/0226330 A1 | 9/2012 | Kolen et al. |
| 2012/0239123 A1 | 9/2012 | Weber |
| 2012/0240940 A1 | 9/2012 | Paraschac |
| 2012/0245483 A1 | 9/2012 | Lundqvist |
| 2012/0253098 A1 | 10/2012 | George et al. |
| 2012/0271206 A1 | 10/2012 | Shalev |
| 2012/0271294 A1 | 10/2012 | Barthe |
| 2012/0277587 A1 | 11/2012 | Adanny |
| 2012/0302821 A1 | 11/2012 | Burnett |
| 2012/0303076 A1 | 11/2012 | Fahey |
| 2012/0310033 A1 | 12/2012 | Muntermann |
| 2012/0310035 A1 | 12/2012 | Schneider et al. |
| 2012/0310311 A1 | 12/2012 | Elkah |
| 2012/0330090 A1 | 12/2012 | Sham |
| 2013/0006039 A1 | 1/2013 | Sadler |
| 2013/0012755 A1 | 1/2013 | Slayton |
| 2013/0030239 A1 | 1/2013 | Weyh |
| 2013/0035745 A1 | 2/2013 | Ahmed |
| 2013/0053620 A1 | 2/2013 | Susedik |
| 2013/0066309 A1 | 3/2013 | Levinson |
| 2013/0079684 A1 | 3/2013 | Rosen |
| 2013/0096363 A1 | 4/2013 | Schneider et al. |
| 2013/0103127 A1 | 4/2013 | Mueller |
| 2013/0116758 A1 | 5/2013 | Levinson |
| 2013/0116759 A1 | 5/2013 | Levinson |
| 2013/0123568 A1 | 5/2013 | Hamilton |
| 2013/0123629 A1 | 5/2013 | Rosenberg |
| 2013/0123764 A1 | 5/2013 | Zarsky |
| 2013/0123765 A1 | 5/2013 | Zarsky |
| 2013/0131764 A1 | 5/2013 | Grove |
| 2013/0137918 A1 | 5/2013 | Phillips |
| 2013/0144280 A1 | 6/2013 | Eckhouse |
| 2013/0150653 A1 | 6/2013 | Borsody |
| 2013/0158440 A1 | 6/2013 | Allison |

(56) References Cited

U.S. PATENT DOCUMENTS

| | | |
|---|---|---|
| 2013/0158634 A1 | 6/2013 | Ron Edoute |
| 2013/0158636 A1 | 6/2013 | Ting |
| 2013/0178764 A1 | 7/2013 | Eckhouse |
| 2013/0184693 A1 | 7/2013 | Neev |
| 2013/0190744 A1 | 7/2013 | Avram |
| 2013/0238043 A1 | 9/2013 | Beardall |
| 2013/0238061 A1 | 9/2013 | Ron Edoute |
| 2013/0238062 A1 | 9/2013 | Ron Edoute |
| 2013/0245731 A1 | 9/2013 | Allison |
| 2013/0253384 A1 | 9/2013 | Anderson |
| 2013/0253493 A1 | 9/2013 | Anderson |
| 2013/0253494 A1 | 9/2013 | Anderson |
| 2013/0253495 A1 | 9/2013 | Anderson |
| 2013/0253496 A1 | 9/2013 | Anderson |
| 2013/0261374 A1 | 10/2013 | Elder |
| 2013/0261683 A1 | 10/2013 | Soikum |
| 2013/0267943 A1 | 10/2013 | Hancock |
| 2013/0289433 A1 | 10/2013 | Jin et al. |
| 2013/0303904 A1 | 11/2013 | Barthe |
| 2013/0304159 A1 | 11/2013 | Simon |
| 2013/0317281 A1 | 11/2013 | Schneider |
| 2013/0317282 A1 | 11/2013 | Ron Edoute |
| 2013/0331637 A1 | 12/2013 | Greff |
| 2014/0005758 A1 | 1/2014 | Ben-Yehuda |
| 2014/0005760 A1 | 1/2014 | Levinson |
| 2014/0012064 A1 | 1/2014 | Riehl et al. |
| 2014/0018767 A1 | 1/2014 | Harris |
| 2014/0025033 A1 | 1/2014 | Mirkov |
| 2014/0025142 A1 | 1/2014 | Zarksy |
| 2014/0046423 A1 | 2/2014 | Rajguru |
| 2014/0066786 A1 | 3/2014 | Naghavi |
| 2014/0067025 A1 | 3/2014 | Levinson |
| 2014/0081359 A1 | 3/2014 | Sand |
| 2014/0148870 A1 | 5/2014 | Burnett |
| 2014/0194958 A1 | 7/2014 | Chabal |
| 2014/0200388 A1 | 7/2014 | Schneider |
| 2014/0221990 A1 | 8/2014 | Kreindel |
| 2014/0235928 A1 | 8/2014 | Zangen et al. |
| 2014/0243933 A1 | 8/2014 | Ginggen |
| 2014/0249355 A1 | 9/2014 | Martinez |
| 2014/0249609 A1 | 9/2014 | Zarsky |
| 2014/0257071 A1 | 9/2014 | Curran |
| 2014/0257443 A1 | 9/2014 | Baker |
| 2014/0276248 A1 | 9/2014 | Hall |
| 2014/0276693 A1 | 9/2014 | Altshuler |
| 2014/0277219 A1 | 9/2014 | Nanda |
| 2014/0277302 A1 | 9/2014 | Weber |
| 2014/0303425 A1 | 10/2014 | Pilla |
| 2014/0303525 A1 | 10/2014 | Sitharaman |
| 2014/0303696 A1 | 10/2014 | Anderson |
| 2014/0303697 A1 | 10/2014 | Anderson |
| 2014/0316393 A1 | 10/2014 | Levinson |
| 2014/0324120 A1 | 10/2014 | Bogie et al. |
| 2014/0330067 A1 | 11/2014 | Jordan |
| 2014/0350438 A1 | 11/2014 | Papirov |
| 2014/0357935 A1 | 12/2014 | Ilmoniemi et al. |
| 2014/0364841 A1 | 12/2014 | Kornstein |
| 2014/0371515 A1 | 12/2014 | John |
| 2014/0378875 A1 | 12/2014 | Ron Edoute |
| 2015/0005569 A1 | 1/2015 | Missoli |
| 2015/0005759 A1 | 1/2015 | Welches et al. |
| 2015/0018667 A1 | 1/2015 | Radman et al. |
| 2015/0025299 A1 | 1/2015 | Ron Edoute |
| 2015/0080769 A1 | 3/2015 | Lotsch |
| 2015/0088105 A1 | 3/2015 | Fatemi |
| 2015/0094788 A1 | 4/2015 | Pierenkemper |
| 2015/0112412 A1 | 4/2015 | Anderson |
| 2015/0119849 A1 | 4/2015 | Aronhalt |
| 2015/0123661 A1 | 5/2015 | Yui |
| 2015/0127075 A1 | 5/2015 | Ward |
| 2015/0133717 A1 | 5/2015 | Ghiron |
| 2015/0133718 A1 | 5/2015 | Schneider et al. |
| 2015/0141877 A1 | 5/2015 | Feldman |
| 2015/0148858 A1 | 5/2015 | Kaib |
| 2015/0157873 A1 | 6/2015 | Sokolowski |
| 2015/0165226 A1 | 6/2015 | Simon |
| 2015/0165232 A1 | 6/2015 | Altshuler |
| 2015/0165238 A1 | 6/2015 | Slayton |
| 2015/0174002 A1 | 6/2015 | Burbank |
| 2015/0202454 A1 | 7/2015 | Burnett |
| 2015/0216719 A1 | 8/2015 | Debenedictis |
| 2015/0216720 A1 | 8/2015 | Debenedictis |
| 2015/0216816 A1 | 8/2015 | O'Neil |
| 2015/0223975 A1 | 8/2015 | Anderson |
| 2015/0238248 A1 | 8/2015 | Thompson |
| 2015/0238771 A1 | 8/2015 | Zársk |
| 2015/0272776 A1 | 10/2015 | Gonzales |
| 2015/0283022 A1 | 10/2015 | Lee |
| 2015/0297909 A1 | 10/2015 | Peashock |
| 2015/0314133 A1 | 11/2015 | Yamashiro |
| 2015/0328077 A1 | 11/2015 | Levinson |
| 2015/0328475 A1 | 11/2015 | Kim |
| 2015/0342661 A1 | 12/2015 | Ron Edoute |
| 2015/0342780 A1 | 12/2015 | Levinson |
| 2015/0360045 A1 | 12/2015 | Fischell |
| 2015/0367141 A1 | 12/2015 | Goetz |
| 2015/0375005 A1 | 12/2015 | Segal |
| 2016/0015995 A1 | 1/2016 | Leung |
| 2016/0016013 A1 | 1/2016 | Capelli |
| 2016/0020070 A1 | 1/2016 | Kim |
| 2016/0022349 A1* | 1/2016 | Woloszko ......... A61B 18/1206 606/34 |
| 2016/0030763 A1 | 2/2016 | Midorikawa |
| 2016/0045755 A1 | 2/2016 | Chun |
| 2016/0051401 A1 | 2/2016 | Yee |
| 2016/0051827 A1 | 2/2016 | Ron Edoute |
| 2016/0066977 A1 | 3/2016 | Neal, II |
| 2016/0066994 A1 | 3/2016 | Shanks |
| 2016/0067516 A1 | 3/2016 | Schneider |
| 2016/0067517 A1 | 3/2016 | Burnett |
| 2016/0089550 A1 | 3/2016 | Debenedictis |
| 2016/0106982 A1 | 4/2016 | Cakmak |
| 2016/0121112 A1 | 5/2016 | Azar |
| 2016/0129273 A1 | 5/2016 | Park |
| 2016/0129274 A1 | 5/2016 | Park |
| 2016/0136462 A1 | 5/2016 | Lewis, Jr. et al. |
| 2016/0150494 A1 | 5/2016 | Tabet |
| 2016/0151637 A1 | 6/2016 | Abe |
| 2016/0158574 A1 | 6/2016 | Eckhouse |
| 2016/0175193 A1 | 6/2016 | Jung |
| 2016/0184601 A1 | 6/2016 | Gleich |
| 2016/0193466 A1 | 7/2016 | Burnett |
| 2016/0213924 A1 | 7/2016 | Coleman |
| 2016/0220834 A1 | 8/2016 | Schwarz |
| 2016/0250494 A1 | 9/2016 | Sakaki |
| 2016/0256702 A1 | 9/2016 | Schwarz |
| 2016/0256703 A1 | 9/2016 | Schwarz |
| 2016/0270951 A1 | 9/2016 | Martins |
| 2016/0317346 A1 | 11/2016 | Kovach |
| 2016/0317827 A1 | 11/2016 | Schwarz |
| 2016/0324684 A1 | 11/2016 | Levinson |
| 2016/0346561 A1 | 12/2016 | Ron Edoute |
| 2016/0354237 A1 | 12/2016 | Gonzales |
| 2017/0001024 A1 | 1/2017 | Prouza |
| 2017/0001025 A1 | 1/2017 | Schwarz |
| 2017/0001026 A1 | 1/2017 | Schwarz |
| 2017/0001027 A1 | 1/2017 | Ladman |
| 2017/0001028 A1 | 1/2017 | Ladman |
| 2017/0001029 A1 | 1/2017 | Pribula |
| 2017/0001030 A1 | 1/2017 | Pribula |
| 2017/0007309 A1 | 1/2017 | Debenedictis |
| 2017/0036019 A1 | 2/2017 | Matsushita |
| 2017/0043177 A1 | 2/2017 | Ron Edoute |
| 2017/0050019 A1 | 2/2017 | Ron Edoute |
| 2017/0072212 A1 | 3/2017 | Ladman |
| 2017/0087373 A1 | 3/2017 | Schwarz |
| 2017/0100585 A1 | 4/2017 | Hall |
| 2017/0105869 A1 | 4/2017 | Frangineas, Jr. |
| 2017/0106201 A1 | 4/2017 | Schwarz |
| 2017/0106203 A1 | 4/2017 | Schneider et al. |
| 2017/0120067 A1 | 5/2017 | Prouza |
| 2017/0143958 A1 | 5/2017 | Shalev |
| 2017/0156907 A1 | 6/2017 | Harris |
| 2017/0173347 A1 | 6/2017 | Schwarz |

(56) References Cited

U.S. PATENT DOCUMENTS

| | | |
|---|---|---|
| 2017/0182334 A1 | 6/2017 | Altshuler |
| 2017/0182335 A1 | 6/2017 | Altshuler |
| 2017/0189707 A1 | 7/2017 | Zabara |
| 2017/0196731 A1 | 7/2017 | Debenedictis |
| 2017/0209708 A1 | 7/2017 | Schwarz |
| 2017/0239079 A1 | 8/2017 | Root |
| 2017/0239467 A1 | 8/2017 | Shalev |
| 2017/0259077 A1 | 9/2017 | Jin |
| 2017/0280889 A1 | 10/2017 | Koch |
| 2017/0304642 A1 | 10/2017 | Ron Edoute |
| 2017/0319378 A1 | 11/2017 | Anderson |
| 2017/0325992 A1 | 11/2017 | Debenedictis |
| 2017/0325993 A1 | 11/2017 | Jimenez Lozano |
| 2017/0326042 A1 | 11/2017 | Zeng |
| 2017/0326346 A1 | 11/2017 | Jimenez Lozano |
| 2017/0333705 A1 | 11/2017 | Schwarz |
| 2017/0348143 A1 | 12/2017 | Rosen |
| 2017/0348539 A1 | 12/2017 | Schwarz |
| 2017/0354530 A1 | 12/2017 | Shagdar |
| 2017/0361095 A1 | 12/2017 | Mueller et al. |
| 2018/0000347 A1 | 1/2018 | Perez et al. |
| 2018/0001106 A1 | 1/2018 | Schwarz |
| 2018/0001107 A1 | 1/2018 | Schwarz |
| 2018/0021565 A1 | 1/2018 | Dar et al. |
| 2018/0028831 A1 | 2/2018 | Ron Edoute |
| 2018/0036548 A1 | 2/2018 | Nusse |
| 2018/0043151 A1 | 2/2018 | Ejiri et al. |
| 2018/0071544 A1 | 3/2018 | Ghiron et al. |
| 2018/0103991 A1 | 4/2018 | Linhart |
| 2018/0125416 A1 | 5/2018 | Schwarz |
| 2018/0133498 A1 | 5/2018 | Chornenky |
| 2018/0153736 A1 | 6/2018 | Mills |
| 2018/0153760 A1 | 6/2018 | Rosen |
| 2018/0161197 A1 | 6/2018 | Baker |
| 2018/0177996 A1 | 6/2018 | Gozani et al. |
| 2018/0185081 A1 | 7/2018 | O'Neil |
| 2018/0185189 A1 | 7/2018 | Weber |
| 2018/0214300 A1 | 8/2018 | Anderson |
| 2018/0228646 A1 | 8/2018 | Gonzales |
| 2018/0229048 A1 | 8/2018 | Sikora |
| 2018/0236254 A1 | 8/2018 | Schwarz |
| 2018/0250056 A1 | 9/2018 | Avram |
| 2018/0263677 A1 | 9/2018 | Hilton |
| 2018/0264245 A1 | 9/2018 | Edwards |
| 2018/0271767 A1 | 9/2018 | Jimenez Lozano |
| 2018/0296831 A1 | 10/2018 | Matsushita |
| 2018/0310950 A1 | 11/2018 | Yee |
| 2018/0345012 A1 | 12/2018 | Schwarz |
| 2018/0353767 A1 | 12/2018 | Biginton |
| 2019/0000524 A1 | 1/2019 | Rosen |
| 2019/0000529 A1 | 1/2019 | Kothare |
| 2019/0000663 A1 | 1/2019 | Anderson |
| 2019/0029876 A1 | 1/2019 | Anderson |
| 2019/0030356 A1 | 1/2019 | Schwarz |
| 2019/0053941 A1 | 2/2019 | Samson |
| 2019/0111255 A1 | 4/2019 | Errico et al. |
| 2019/0117965 A1 | 4/2019 | Iger et al. |
| 2019/0134414 A1 | 5/2019 | Prouza |
| 2019/0151655 A1 | 5/2019 | Hall |
| 2019/0168012 A1 | 6/2019 | Biginton |
| 2019/0183562 A1 | 6/2019 | Widgerow |
| 2019/0192219 A1 | 6/2019 | Kreindel |
| 2019/0192853 A1 | 6/2019 | Kim et al. |
| 2019/0192872 A1 | 6/2019 | Schwarz |
| 2019/0192873 A1 | 6/2019 | Schwarz |
| 2019/0192875 A1 | 6/2019 | Schwarz |
| 2019/0201705 A1 | 7/2019 | Schwarz |
| 2019/0201706 A1 | 7/2019 | Schwarz |
| 2019/0209836 A1 | 7/2019 | Yakoub et al. |
| 2019/0255346 A1 | 8/2019 | Ghiron |
| 2019/0269909 A1 | 9/2019 | Gozani et al. |
| 2019/0275320 A1 | 9/2019 | Kim et al. |
| 2019/0299018 A1 | 10/2019 | Chornenky |
| 2019/0314629 A1 | 10/2019 | Kreindel |
| 2019/0314638 A1 | 10/2019 | Kreindel |
| 2019/0329065 A1 | 10/2019 | Gandel |
| 2019/0336783 A1 | 11/2019 | Sokolowski |
| 2019/0344091 A1 | 11/2019 | Fischer |
| 2019/0350646 A1 | 11/2019 | Kreindel |
| 2019/0365462 A1 | 12/2019 | Casalino |
| 2019/0388698 A1 | 12/2019 | Schwarz |
| 2020/0001103 A1 | 1/2020 | Schwarz |
| 2020/0016422 A1 | 1/2020 | Ron Edoute |
| 2020/0016423 A1 | 1/2020 | Ron Edoute |
| 2020/0054890 A1 | 2/2020 | Schwarz |
| 2020/0061385 A1 | 2/2020 | Schwarz |
| 2020/0061386 A1 | 2/2020 | Schwarz |
| 2020/0094066 A1 | 3/2020 | Heath |
| 2020/0114160 A1 | 4/2020 | Blendermann |
| 2020/0129759 A1 | 4/2020 | Schwarz |
| 2020/0139148 A1 | 5/2020 | Schwarz |
| 2020/0155221 A1 | 5/2020 | Marchitto |
| 2020/0171297 A1 | 6/2020 | Kirson et al. |
| 2020/0197696 A1 | 6/2020 | Nagel et al. |
| 2020/0206524 A1 | 7/2020 | Katznelson |
| 2020/0237424 A1 | 7/2020 | Hunziker |
| 2020/0281642 A1 | 9/2020 | Kreindel |
| 2020/0289838 A1 | 9/2020 | Schwarz |
| 2020/0324133 A1 | 10/2020 | Schwarz |
| 2020/0330782 A1 | 10/2020 | Zabara |
| 2020/0352633 A1 | 11/2020 | Treen et al. |
| 2020/0353244 A1 | 11/2020 | Yamazaki |
| 2020/0353273 A1 | 11/2020 | Zucco |
| 2020/0360681 A1 | 11/2020 | Lay |
| 2021/0008369 A1 | 1/2021 | Crosson |
| 2021/0038894 A1 | 2/2021 | Mowery et al. |
| 2021/0146150 A1 | 5/2021 | Frangineas, Jr. et al. |
| 2021/0275825 A1 | 9/2021 | Kreindel |
| 2021/0283395 A1 | 9/2021 | Kreindel |
| 2021/0361938 A1 | 11/2021 | Gershonowitz |

FOREIGN PATENT DOCUMENTS

| | | |
|---|---|---|
| AU | 2012244313 B2 | 11/2014 |
| AU | 2014203094 B2 | 7/2015 |
| AU | 2013207657 B2 | 11/2015 |
| BR | PI0812502 A2 | 6/2015 |
| BR | PI08125023 | 6/2015 |
| CA | 2484880 A1 | 4/2006 |
| CA | 2604112 C | 7/2016 |
| CA | 3019140 A1 | 10/2017 |
| CA | 3019410 A1 | 10/2017 |
| CA | 3023821 A1 | 11/2017 |
| CH | 714113 A2 | 3/2019 |
| CN | 86204070 U | 9/1987 |
| CN | 87203746 U | 12/1987 |
| CN | 87215926 U | 7/1988 |
| CN | 1026953 C | 12/1994 |
| CN | 1027958 C | 3/1995 |
| CN | 2192348 Y | 3/1995 |
| CN | 1206975 C | 6/2005 |
| CN | 101234231 A | 8/2008 |
| CN | 101327358 A | 12/2008 |
| CN | 201906360 U | 7/2011 |
| CN | 102319141 A | 1/2012 |
| CN | 102711706 | 10/2012 |
| CN | 102711706 A | 10/2012 |
| CN | 102847231 A | 1/2013 |
| CN | 202637725 U | 1/2013 |
| CN | 203169831 U | 9/2013 |
| CN | 102319141 B | 8/2014 |
| CN | 106540375 A | 3/2017 |
| CN | 107613914 A | 1/2018 |
| CN | 108882992 A | 11/2018 |
| CN | 109310516 A | 2/2019 |
| CN | 112221015 A | 1/2021 |
| DE | 718637 C | 3/1942 |
| DE | 1118902 B | 12/1961 |
| DE | 2748780 A1 | 5/1978 |
| DE | 3205048 A1 | 8/1983 |
| DE | 3340974 A1 | 5/1985 |
| DE | 3610474 A1 | 10/1986 |
| DE | 3825165 A1 | 1/1990 |
| DE | 3340974 C2 | 7/1994 |

(56) References Cited

FOREIGN PATENT DOCUMENTS

| | | |
|---|---|---|
| DE | 69318706 T2 | 1/1999 |
| DE | 10062050 A1 | 4/2002 |
| DE | 102004006192 A1 | 9/2005 |
| DE | 60033756 T2 | 6/2007 |
| DE | 102009023855 A1 | 12/2010 |
| DE | 102009050010 A1 | 5/2011 |
| DE | 102010004307 A1 | 7/2011 |
| DE | 102011014291 A1 | 9/2012 |
| DE | 102013211859 B4 | 7/2015 |
| DE | 102016116399 A1 | 3/2018 |
| DE | 202016008884 U1 | 7/2020 |
| DE | 102010014157 B4 | 2/2021 |
| DK | 0633008 T3 | 3/1999 |
| EA | 000494 B1 | 8/1999 |
| EA | 002087 B1 | 12/2001 |
| EA | 002179 B1 | 2/2002 |
| EA | 003851 B1 | 10/2003 |
| EA | 007347 B1 | 8/2006 |
| EA | 007975 B1 | 2/2007 |
| EP | 0048451 A1 | 3/1982 |
| EP | 0209246 A1 | 1/1987 |
| EP | 0459101 A1 | 12/1991 |
| EP | 0459401 A1 | 12/1991 |
| EP | 0633008 A1 | 1/1995 |
| EP | 0788813 A1 | 8/1997 |
| EP | 0633008 B1 | 5/1998 |
| EP | 0692993 B1 | 9/1999 |
| EP | 1022034 A1 | 7/2000 |
| EP | 1916013 A1 | 4/2008 |
| EP | 2069014 | 6/2009 |
| EP | 2139560 | 1/2010 |
| EP | 2124800 B1 | 11/2010 |
| EP | 1917935 B1 | 1/2011 |
| EP | 2308559 A2 | 4/2011 |
| EP | 2461765 | 6/2012 |
| EP | 2461765 A1 | 6/2012 |
| EP | 2501352 | 9/2012 |
| EP | 2614807 | 7/2013 |
| EP | 2614807 A1 | 7/2013 |
| EP | 2676700 A2 | 12/2013 |
| EP | 2694159 A2 | 2/2014 |
| EP | 2749259 A1 | 7/2014 |
| EP | 2814445 A1 | 12/2014 |
| EP | 2856986 A1 | 4/2015 |
| EP | 3009167 A1 | 4/2016 |
| EP | 2501352 B1 | 7/2016 |
| EP | 3209246 A1 | 8/2017 |
| EP | 3342379 A1 | 7/2018 |
| EP | 3389532 | 10/2018 |
| EP | 3389532 A1 | 10/2018 |
| EP | 3434323 A1 | 1/2019 |
| EP | 3721939 A1 | 10/2020 |
| ES | 2118925 T3 | 10/1998 |
| ES | 2300569 T3 | 6/2008 |
| ES | 2305698 T3 | 11/2008 |
| ES | 2359581 T3 | 5/2011 |
| ES | 2533145 A2 | 4/2015 |
| ES | 2533145 R1 | 10/2015 |
| ES | 2533145 B1 | 7/2016 |
| FR | 3041881 A1 | 4/2017 |
| FR | 3061012 A1 | 6/2018 |
| GB | 260116 A | 10/1926 |
| GB | 304587 A | 3/1930 |
| GB | 390500 A | 4/1933 |
| GB | 871672 A | 6/1961 |
| GB | 2176009 A | 12/1986 |
| GB | 2188238 A | 9/1987 |
| GB | 2176009 B | 12/1989 |
| GB | 2261820 A | 6/1993 |
| GB | 2286660 A | 8/1995 |
| GB | 2395907 B | 12/2004 |
| GB | 2504984 A | 2/2014 |
| GB | 2521240 A | 6/2015 |
| GB | 2552004 A | 1/2018 |
| GR | 3027678 T3 | 11/1998 |
| IT | 1217550 B | 3/1990 |
| IT | RE20120010 A1 | 8/2013 |
| IT | UB20159823 A1 | 7/2017 |
| JP | 2003305131 A | 10/2003 |
| JP | 2006130055 A | 5/2006 |
| JP | 4178762 B2 | 11/2008 |
| JP | 4324673 B2 | 9/2009 |
| JP | 2010207268 A | 9/2010 |
| JP | 2010533054 A | 10/2010 |
| JP | 2011194176 A | 10/2011 |
| JP | 2013063285 | 4/2013 |
| JP | 2013063285 A | 4/2013 |
| JP | 2017518857 A | 7/2017 |
| JP | 2018501927 | 1/2018 |
| JP | 2018018650 A | 2/2018 |
| KR | 20030065126 A | 8/2003 |
| KR | 100484618 B1 | 4/2005 |
| KR | 100491988 B1 | 5/2005 |
| KR | 200407524 Y1 | 1/2006 |
| KR | 100556230 B1 | 3/2006 |
| KR | 200410065 Y1 | 3/2006 |
| KR | 100841596 B1 | 6/2008 |
| KR | 20090063618 A | 6/2009 |
| KR | 20090095143 A | 9/2009 |
| KR | 100936914 B1 | 1/2010 |
| KR | 1020100026107 A | 3/2010 |
| KR | 101022244 B1 | 3/2011 |
| KR | 20110123831 A | 11/2011 |
| KR | 20120037011 | 4/2012 |
| KR | 20120037011 A | 4/2012 |
| KR | 101233286 B1 | 2/2013 |
| KR | 101233287 B1 | 2/2013 |
| KR | 20130072244 A | 7/2013 |
| KR | 101292289 B1 | 8/2013 |
| KR | 20130128391 | 11/2013 |
| KR | 20130128391 A | 11/2013 |
| KR | 101413022 B1 | 7/2014 |
| KR | 101415141 B1 | 7/2014 |
| KR | 101447532 B1 | 10/2014 |
| KR | 101511444 B1 | 4/2015 |
| KR | 20150058102 A | 5/2015 |
| KR | 101539633 B1 | 7/2015 |
| KR | 20150079619 A | 7/2015 |
| KR | 20150106379 A | 9/2015 |
| KR | 101650155 B1 | 8/2016 |
| KR | 101673182 B1 | 11/2016 |
| KR | 20170090654 A | 8/2017 |
| KR | 20170107603 A | 9/2017 |
| KR | 101794269 B1 | 11/2017 |
| KR | 20180059114 A | 6/2018 |
| KR | 20180092020 A | 8/2018 |
| KR | 101941863 | 1/2019 |
| KR | 101941863 B1 | 1/2019 |
| KR | 20190005981 A | 1/2019 |
| KR | 102000971 B1 | 7/2019 |
| KR | 20190001779 U | 7/2019 |
| KR | 200491572 Y1 | 5/2020 |
| KR | 20200000889 U | 5/2020 |
| KR | 20200052602 A | 5/2020 |
| KR | 20200056692 A | 5/2020 |
| KR | 20200056693 A | 5/2020 |
| KR | 20200056801 A | 5/2020 |
| KR | 20200056802 A | 5/2020 |
| KR | 20200057154 A | 5/2020 |
| KR | 20210002973 A | 1/2021 |
| KR | 20210002974 A | 1/2021 |
| MX | 2012012158 A | 4/2014 |
| NL | 7510644 A | 3/1977 |
| NL | 1037451 C2 | 5/2011 |
| RU | 2212909 C2 | 9/2003 |
| RU | 2226115 C2 | 3/2004 |
| RU | 2281128 C2 | 8/2006 |
| RU | 2373971 C2 | 11/2009 |
| RU | 2392979 C2 | 6/2010 |
| RU | 2395267 C2 | 7/2010 |
| RU | 2496532 C2 | 10/2013 |
| RU | 2529471 C2 | 9/2014 |
| RU | 2596053 C2 | 8/2016 |
| RU | 2637104-02 | 11/2017 |

(56) References Cited

FOREIGN PATENT DOCUMENTS

| | | |
|---|---|---|
| RU | 2645923 C2 | 2/2018 |
| SI | 24921 A | 8/2016 |
| TW | 200423986 | 11/2004 |
| WO | WO-9312835 A1 | 7/1993 |
| WO | 9521655 A1 | 8/1995 |
| WO | 9527533 | 10/1995 |
| WO | 9932191 A1 | 7/1999 |
| WO | 0013749 A1 | 3/2000 |
| WO | 0044346 A1 | 8/2000 |
| WO | 0107111 A2 | 2/2001 |
| WO | 0112089 | 2/2001 |
| WO | 0112089 A1 | 2/2001 |
| WO | 0193797 A2 | 12/2001 |
| WO | 0225675 A1 | 3/2002 |
| WO | 03078596 A2 | 9/2003 |
| WO | 03079916 | 10/2003 |
| WO | 03090863 A1 | 11/2003 |
| WO | 03103769 A1 | 12/2003 |
| WO | WO-2004078255 A1 | 9/2004 |
| WO | 2004087255 A1 | 10/2004 |
| WO | 2004095385 A2 | 11/2004 |
| WO | 2004095835 A1 | 11/2004 |
| WO | WO-2004096343 A2 | 11/2004 |
| WO | 2004108211 | 12/2004 |
| WO | 2004108211 A1 | 12/2004 |
| WO | 2005032660 A1 | 4/2005 |
| WO | WO-2005107866 A1 | 11/2005 |
| WO | 2006115120 A1 | 11/2006 |
| WO | WO-2007096206 A1 | 8/2007 |
| WO | 2007140584 A1 | 12/2007 |
| WO | 2008012827 | 1/2008 |
| WO | 2008012827 A2 | 1/2008 |
| WO | 2008060494 | 5/2008 |
| WO | WO-2008049775 A1 | 5/2008 |
| WO | 2008109058 A1 | 9/2008 |
| WO | 2008127011 A2 | 10/2008 |
| WO | 2008145260 A2 | 12/2008 |
| WO | 2009011708 A1 | 1/2009 |
| WO | 2009013729 | 1/2009 |
| WO | 2009013729 A2 | 1/2009 |
| WO | WO-2009036040 A1 | 3/2009 |
| WO | 2009042863 A1 | 4/2009 |
| WO | 2009044400 | 4/2009 |
| WO | 2009044400 A2 | 4/2009 |
| WO | WO-2009047628 A2 | 4/2009 |
| WO | 2009083915 A2 | 7/2009 |
| WO | 2010007614 A2 | 1/2010 |
| WO | 2010007614 A3 | 1/2010 |
| WO | 2010022278 | 2/2010 |
| WO | 2010135425 A1 | 11/2010 |
| WO | 2010139376 A1 | 12/2010 |
| WO | 2011011749 A1 | 1/2011 |
| WO | 2011016019 | 2/2011 |
| WO | 2011016019 A1 | 2/2011 |
| WO | 2011021184 | 2/2011 |
| WO | 2011045002 A1 | 4/2011 |
| WO | 2011058556 | 5/2011 |
| WO | 2011058565 A2 | 5/2011 |
| WO | WO-2011053607 A1 | 5/2011 |
| WO | 2011156495 | 12/2011 |
| WO | 2011156495 A2 | 12/2011 |
| WO | WO-2012005766 A1 | 1/2012 |
| WO | 2012029065 | 3/2012 |
| WO | 2012029065 A2 | 3/2012 |
| WO | 2012040243 A1 | 3/2012 |
| WO | WO-2012073232 A1 | 6/2012 |
| WO | 2012103632 A1 | 8/2012 |
| WO | WO-2012119293 A1 | 9/2012 |
| WO | 2012138169 A2 | 10/2012 |
| WO | 2013021380 A1 | 2/2013 |
| WO | 2013026393 A1 | 2/2013 |
| WO | 2013035088 A1 | 3/2013 |
| WO | 2013074576 | 5/2013 |
| WO | 2013074576 A2 | 5/2013 |
| WO | 2013098815 A1 | 7/2013 |
| WO | 2013191699 A1 | 12/2013 |
| WO | 2014009875 | 1/2014 |
| WO | 2014016820 A2 | 1/2014 |
| WO | 2014109653 A1 | 7/2014 |
| WO | 2014141229 | 9/2014 |
| WO | 2014141229 A1 | 9/2014 |
| WO | 2014149021 | 9/2014 |
| WO | 2014149021 A2 | 9/2014 |
| WO | 2014151431 | 9/2014 |
| WO | 2014151431 A2 | 9/2014 |
| WO | WO-2014137344 A1 | 9/2014 |
| WO | 2014163020 A1 | 10/2014 |
| WO | 2014164926 A1 | 10/2014 |
| WO | 2015012672 A1 | 1/2015 |
| WO | WO-2015004540 A2 | 1/2015 |
| WO | WO-2015012639 A1 | 1/2015 |
| WO | 2015052705 A1 | 4/2015 |
| WO | 2015083305 A1 | 6/2015 |
| WO | 2015137733 A1 | 9/2015 |
| WO | 2015157725 A1 | 10/2015 |
| WO | 2015179571 A1 | 11/2015 |
| WO | WO-2016116747 A1 | 7/2016 |
| WO | 2016140871 A1 | 9/2016 |
| WO | 2017002065 A1 | 1/2017 |
| WO | 2017103923 | 6/2017 |
| WO | 2017159959 A1 | 9/2017 |
| WO | 2017160097 A2 | 9/2017 |
| WO | 2017176621 A1 | 10/2017 |
| WO | 2017196548 A1 | 11/2017 |
| WO | WO-2017212253 A1 | 12/2017 |
| WO | 2018008023 A1 | 1/2018 |
| WO | WO-2018006086 A1 | 1/2018 |
| WO | 2018044825 A1 | 3/2018 |
| WO | 2018121998 A2 | 7/2018 |
| WO | 2018122535 A1 | 7/2018 |
| WO | 2017160097 A3 | 9/2018 |
| WO | 2018208992 A1 | 11/2018 |
| WO | WO-2019120420 A1 | 6/2019 |
| WO | WO-2019150378 A1 | 8/2019 |
| WO | 2019166965 A1 | 9/2019 |
| WO | 2019173866 A1 | 9/2019 |
| WO | 2019183622 A1 | 9/2019 |
| WO | 2020002801 | 1/2020 |
| WO | 2020002801 A1 | 1/2020 |
| WO | 2020035852 | 2/2020 |
| WO | 2020035852 A2 | 2/2020 |
| WO | 2020041502 A1 | 2/2020 |
| WO | WO-2020142470 A1 | 7/2020 |
| WO | WO-2020144486 A1 | 7/2020 |
| WO | 2020174444 A1 | 9/2020 |
| WO | WO-2020183508 A1 | 9/2020 |
| WO | WO-2020190514 A1 | 9/2020 |
| WO | 2020208590 A1 | 10/2020 |
| WO | WO-2020264263 A1 | 12/2020 |
| WO | WO-2021013654 A1 | 1/2021 |
| WO | WO-2021102365 A1 | 5/2021 |

OTHER PUBLICATIONS

Wanitphakdeedecha et al., Treatment of abdominal cellulite and circumference reduction with radiofrequency and dynamic muscle activation, J. Cosmetic and Laser Therapy, 17:5, 246-251 (2015).
Kocbach et al., A Simulation Approach to Optimizing Performance of Equipment for Thermostimulation of Muscle Tissue using COMSOL Multiphysics, Biophysics & Bioeng. Letters, 4(2), (2011) (26 pages).
Maximus Non-invasive Body Shaping System User Manual, http://download.lifvation.com/Maximus_UserManual.pdf, May 2012 (44 pages).
Notice of Allowance dated Oct. 8, 2019 for U.S. Appl. No. 15/603,162 (pp. 1-8).
Office Action dated Aug. 15, 2019 for U.S. Appl. No. 16/194,800 (pp. 1-12).
Office Action dated Oct. 7, 2019 for U.S. Appl. No. 15/678,915 (pp. 1-8).
Trifractional FAQs, http://pollogen.lifvation.com/FAQ/TriFractional%20FAQs.pdf, Aug. 2011 (4 pages).
TriLipo MED Procedure, http://download.lifvation.com/Maximus_TriLipoMED_Intro.pdf, Apr. 2013 (66 pages).

(56) References Cited

OTHER PUBLICATIONS

Venus Swan, http://www.medicom.cz/UserFiles/File/LekarskeNenue/020Swan%20EN.pdf, Apr. 2016 (2 pages).
501 (k) K030708 Slendertone FLEX Letter from Department of Health and Humane Serivces, Public Health Service, Jun. 25, 2003, 6 pages.
501 (k) K163165 AM-100 Letter from Department of Health and Human Services, Public Health Service, Feb. 16, 2017, 9 pages.
Abulhasan JF, "Peripheral Electrical and Magnetic Stimulation to Augment Resistance Training", J Func Morph, Sep. 1, 2016, 15 pages.
Accent Radiofrequency System, Operator's Manual, Alma Lasers, Wellbeing Through Technology, 2008, 82 Pages.
Alma Lasers., "Accent Radiofrequency System, Operator's Manual," Wellbeing Through Technology, 2008, Chapters 1-8, Appendix A, 79 pages.
Arjunan, P.A., et al., "Computation and Evaluation of Features of Surface Electromyogram to Identify the Force of Muscle Contraction and Muscle Fatigue," BioMed research international 2014:197960, Hindawi Pub. Co, United States (2014) 7 pages.
Avram, M.M and Harry, R.S., "Cryolipolysis for Subcutaneous Fat Layer Reduction," Lasers in Surgery and Medicine, 41(10):703-708, Wiley-Liss, United States (Dec. 2009).
Bachasson D, "Quadriceps function assessment using an incremental test and magnetic neurostimulation: A reliability study", J. Electromyography & Kinesiology, Dec. 20, 2012, 10 pages.
Baranov, A., Krion, Whole Body Cryotherapy, Russia, 19 Pages.
Barker, A.T, "An Introduction to the Basic Principles of Magnetic Nerve Stimulation," Journal of Clinical Neurophysiology, 8(1):26-37, Lippincott Williams & Wilkins, United States, (Jan. 1991).
Barker, A.T., "The History and Basic Principles of Magnetic Nerve Stimulation," Electroencephalography and Clinical Neurophysiology 51:3-21, Elsevier, Netherlands (1999).
Barker, A.T., et al., "Non-Invasive Magnetic Stimulation of Human Motor Cortex," Lancet 1(8437):1106-1107, Elsevier, England (May 1985).
Barrett, J., et al., "Mechanisms of Action Underlying the Effect of Repetitive Transcranial Magnetic Stimulation on Mood: Behavioral and Brain Imaging Studies," Neuropsychopharmacology 29(6):1172-1189, Nature Publishing Group, England (Jun. 1905).
Basic Protocol of Salus, Talent with Incontinence Chair, REMED, Nov. 9, 2015, 1 page.
Behrens, M., et al., "Repetitive Peripheral Magnetic Stimulation (15 Hz RPMS) of the Human Soleus Muscle did not Affect Spinal Excitability," Journal of Sports Science and Medicine, 10(1):39-44, Dept. of Sports Medicine, Medical Faculty of Uludag University, Turkey (Mar. 2011).
Beilin, G., et al., "Electromagnetic Fields Applied to the Reduction of Abdominal Obesity," Journal of Cosmetic & Laser Therapy, 14(1):24-42, Informa Healthcare, England, (Feb. 2012).
Belanger, A-Y., "Chapter 13: Neuromuscular Electrical Stimulation," in Therapeutic Electrophysical Agents: Evidence Behind Practice, 3rd Edition, Lupash, E., ed., pp. 220-255, Lippincott Williams & Wilkins, United States (2015).
Benton, et al., "Functional Electrical Stimulation—A Practical Clinical Guide," Second Edition, The Professional Staff Association of the Rancho Los Amigos Hospital, Inc., 42 pages (1981).
Benton, L.A., et al., "Chapter 2: Physiological Basis of Nerve and Muscle Excitation" and "Chapter 4: General Uses of Electrical Stimulation," in Functional Electrical Stimulation: A Practical Guide, 2nd Edition, pp. 11-30 and 53-71, Rancho Los Amigos Rehabilitation Engineering Center, Downey, CA (1981), 42 pages.
Bergh, U., and Ekblom, B., "Influence of Muscle Temperature on Maximal Muscle Strength and Power Output in Human Skeletal Muscles," Acta Physiologica Scandinavica 107(1):33-37, Blackwell Scientific Publications, England (Aug. 1979).
Binder-Macleod, S.A., et al., "Force Output of Cat Motor Units Stimulated with Trains of Linearly Varying Frequency," Journal of Neurophysiology 61(1):208-217, American Physiological Society, United States (Jan. 1989).

Binder-Macleod, S.A., et al., "Use of a Catchlike Property of Human Skeletal Muscle to Reduce Fatigue," Muscle & Nerve 14(9):850-857, John Wiley & Sons, United States (Sep. 1991).
Bio Medical Research Limited., "Slendertone Flex Abdominal Training System, Instructions for Use," All pages (Aug. 2006) 29 pages.
Bio Medical Research Limited., "Slendertone Flex Max Instruction Manual," 36 pages (Apr. 2006).
Bio-Medical Research Ltd., K010335, 510(k) Summary, Slendertone Flex, 933 pages (Sep. 2001).
Bio-Medical Research Ltd., K022855 510(k) Summary, Slendertone, 1-6 (Mar. 2003).
Bischoff, C., et al., "Repetitive Magnetic Nerve Stimulation: Technical Considerations and Clinical Use in the Assessment of Neuromuscular Transmission," Electroencephalography and Clinical Neurophysiology 93(1):15-20, Elsevier, Ireland (Feb. 1994).
Bourland, J.D., et al., "Transchest Magnetic (Eddy-Current) Stimulation of the Dog Heart," Medical & Biological Engineering & Computing 28(2):196-198, Springer, United States (Mar. 1990).
*BTL Industries, Inc.* v. *Allergan Ltd. et al* DDE-1-20-cv-01046, Complaint for Patent Infringement and Exhibits 1-38, 821 pages (Aug. 2020).
*BTL Industries, Inc.* v. *Allergan Ltd. et al* DDE-1-20-CV-01046, Order Granting Motion to Stay Pending Resolution of Proceedings at the International Trade Commission (Unopposed), 2 pages (Oct. 2020).
*BTL Industries, Inc.* v. *Allergan PLC et al* DDE-1-19-cv-02356, Complaint for Patent Infringement and Exhibits 1-34, 375 pages (Dec. 2019).
*BTL Industries, Inc.* v. *Allergan PLC et al* DDE-1-19-cv-02356, Order Granting Stipulation to Stay, Oct. 1, 2020, 1 page.
BTL Industries, Inc., K163165 510(k) Summary, AM-100, All pages (Feb. 2017).
BTL Industries, Inc., K180813 510(k) Summary, Emsculpt, 9 pages (Mar. 2018).
Buenos Aires, Oct. 14, 2014, Venus Concept, Provision No. 7246, 56 pages (With Machine Translation).
Burge, S.M and Dawber, R.P., "Hair Follicle Destruction and Regeneration in Guinea Pig Skin After Cutaneous Freeze Injury," Cryobiology, 27(2):153-163, Elsevier, Netherlands (Apr. 1990).
Busso, M. and Denkova, R., "Efficacy of High Intensity Focused Electro-Magnetic (HIFEM) Field Therapy When Used For Non-Invasive Buttocks Augmentation and Lifting: A Clinical Study" American Society for Laser Medicine and Surgery Abstracts, 382 (2018).
Bustamante, V., et al., "Muscle Training With Repetitive Magnetic Stimulation of the Quadriceps in Severe COPD Patients," Respiratory Medicine, 104(2):237-245, Elsevier, England, (Feb. 2010).
Bustamante, V., et al., "Redox Balance Following Magnetic Stimulation Training in the Quadriceps of Patients With Severe COPD," Free Radical Research, 42(11-12):939-948, Informa Healthcare, England, (Nov. 2008).
Callaghan, M.J., et al., "Electric Muscle Stimulation of the Quadriceps in the Treatment of Patellofemoral Pain," Archives of Physical Medicine and Rehabilitation 85(6):956-962, W.B. Saunders, United Staes (Jun. 2004).
Carbonaro, M., et al., "Architectural Changes in Superficial and Deep Compartments of the Tibialis Anterior during Electrical Stimulation over Different Sites," IEEE transactions on Neural Systems and Rehabilitation Engineering 28(11):2557-2565, IEEE, United States (Nov. 2020).
Caress, J.B., et al., "A Novel Method of Inducing Muscle Cramps Using Repetitive Magnetic Stimulation," Muscle Nerve, 23(1):126-128, John Wiley & Sons, United States, (Jan. 2000).
Certain Non-Invasive Aesthetic Body Contouring Devices, Components Thereof, and Methods of Using the Same, Inv. No. 337-TA-1219, BTL's Statement of Suggested Claim Terms to Be Construed Pursuant to Ground Rule 6b, Nov. 4, 2020, 2 pages.
Certain Non-Invasive Aesthetic Body Contouring Devices, Components Thereof, and Methods of Using the Same, Inv. No. 337-TA-1219, Complainant BTL's Proposed Construction of Disputed Claim Terms, Dec. 8, 2020, 19 pages.

(56) References Cited

OTHER PUBLICATIONS

Certain Non-Invasive Aesthetic Body Contouring Devices, Components Thereof, and Methods of Using the Same, Inv. No. 337-TA-1219, Complaint, Aug. 5, 2020, 93 pages.
Certain Non-Invasive Aesthetic Body Contouring Devices, Components Thereof, and Methods of Using the Same, Inv. No. 337-TA-1219, Joint Claim Construction Chart, Dec. 14, 2020, 15 pages.
Certain Non-Invasive Aesthetic Body Contouring Devices, Components Thereof, and Methods of Using the Same, Inv. No. 337-TA-1219, Respondents' Allergan Limited, Allergan USA, Inc., Allergan, Inc., Zeltiq Aesthetics, Inc., Zeltiq Ireland Unlimited Company, and Zimmer MedizinSysteme GmbH's Notice of Prior Art, Nov. 20, 2020, 53 pages.
Certain Non-Invasive Aesthetic Body Contouring Devices, Components Thereof, and Methods of Using the Same, Inv. No. 337-TA-1219, Respondents' List of Claim Terms for Construction, Nov. 4, 2020, 8 pages.
Certain Non-Invasive Aesthetic Body Contouring Devices, Components Thereof, and Methods of Using the Same, Inv. No. 337-TA-1219, Response of Respondent Zimmer MedizinSysteme GmbH to the Complaint and Notice of Investigation, Oct. 22, 2020, 68 pages.
Certain Non-Invasive Aesthetic Body Contouring Devices, Components Thereof, and Methods of Using the Same, Inv. No. 337-TA-1219, Response of Respondents Allergan Limited, Allergan USA, Inc., Allergan, Inc., Zeltiq Aesthetics, Inc., and Zeltiq IrelandUnlimited Company to the Complaint and Notice of Investigation, Oct. 22, 2020, 69 pages.
Certain Non-Invasive Aesthetic Body Contouring Devices, Components Thereof, and Methods of Using the Same; Inv. No. 337-TA-1219, Joint Claim Construction Chart, Dec. 18, 2020, 15 pages.
Certain Non-Invasive Aesthetic Body Contouring Devices, Components Thereof, and Methods of Using the Same; Inv. No. 337-TA-1219, Respondents' List of Proposed Claim Constructions and Their Intrinsic and Extrinsic Support, filed Dec. 15, 2020, 23 pages.
Certain Non-Invasive Aesthetic Body-Contouring Devices, Components Thereof, and Methods of Using Same, Notice of Institution of Investigation, Inv. No. 337-TA-1219, Notice of Institution of Investigation, Sep. 2, 2020, 21 pages.
Certain Non-Invasive Aesthetic Body-Contouring Devices, Components Thereof, and Methods of Using the Same, Inv. No. 337-TA-1219, Order No. 21 (Initial Determination), Apr. 28, 2021, 5 pages.
Certain Non-Invasive Aesthetic Body-Contouring Devices, Componesnts Thereof, and Methods of Using the Same, Inv. No. 337-TA-1219, Order No. 17: Amending Procedural Schedule, Apr. 9, 2021, 4 pages.
Certified English Translation of Belyaev, A.G., "Effect of Magnetic Stimulation on the Strength Capacity of Skeletal Muscles," Ph.D. Thesis Abstract, Smolensk State Academy of Physical Culture, Sport, and Tourism, Dec. 11, 2020, 23 pages.
Certified English Translation of Belyaev, A.G., "Effect of Magnetic Stimulation on the Strength Capacity of Skeletal Muscles," Ph.D. Thesis, Smolensk State Academy of Physical Culture, Sport, and Tourism, Dec. 11, 2020, 117 pages.
Chattanooga Group of Encore Medical, L.P., "Intelect SWD 100 User Manual, Operation & Installation Instructions for Intelect SWD 00-Model 1600," 98 pages (2009).
Chesterton, L.S., et al., "Skin Temperature Response to Cryotherapy," Archives of Physical Medicine and Rehabilitation, 83(4):543-549, W.B. Saunders, United States (Apr. 2002).
Clinical Application of Electro Magnetic Stimulation, Salus-Talent, Korea Society of interventional Muscle and Soft Tissue Stimulation Therapy, CR Technology, 141 pages.
Collins, D.F., et al., "Large Involuntary Forces Consistent With Plateau-Like Behavior of Human Motoneurons," Journal of Neuroscience 21(11):4059-4065, Society for Neuroscience, United States (Jun. 2001).

Colson, S., et al., "Re-Examination of Training Effects by Electrostimulation in the Human Elbow Musculoskeletal System," International Journal of Sports Medicine 21(4):281-288, Stuttgart, Thieme (May 2000).
Course in Physical Therapy, Presentation, Jan. 4, 2013, 156 pages.
CR Technologies, "Notification of medical device manufacturing item permission, Salus Talent Pop KFDA Approval Document" (English Translation), 3 pages (Sep. 2011).
CR Technologies, "Salus Talent Pop Manual KFDA First Approval Document" (English Translation), Nov. 25, 2011, 47 pages.
CR Technology Co, Ltd., "Salus-Talent Double Sales Brochure" 2 pages, (Oct. 2020).
CR Technology Co. Ltd., "Medical Laser Irradiator Salus-Talent-Pop User Manual Version 1.00" (Nov. 2020) 33 pages.
CR Technology Co. Ltd., Salus Talent Pop User Manual, Ver. 1.00, 32 pages, Approx. 2012.
CR Technology, SALUS-TALENT, Technical File of Electromagnetic Stimulator, Document No. TF-C05, 2008, 241 pages.
CR Technology, Technology for Health and Business for Human Being, investor relations, 2008, 21 pages.
CryoGenTech GmbH, Company Profile, Creating CRYO, Medica, 9 pages.
Currier, D. P., "Effects of Electrical and Electromagnetic Stimulation after Anterior Cruciate Ligament Reconstruction," The Journal of Orthopaedic and Sports Physical Therapy 17(4):177-84, Williams and Wilkins, United States (1993).
Cutera—Trusculpt, 2018, 26 pages.
Cutera, truSculptflex, Brochure, dated 2019, 2 pages.
Cynosure, SculpSure TM, The New Shape of Energy-Based body Contouring, 2015, Cynosure INC, 2 pages.
Cynosure,Smooth Shapes XV, Now with Smoothshape petite, Transforming non-invasive Body Shaping,Retrieved from the Internet: (www.cynosure.com), 2011, Cynosure Inc, 8 pages.
Davies, C.T., et al., "Contractile Properties of the Human Triceps Surae With Some Observations on the Effects of Temperature and Exercise," European Journal of Applied Physiology and Occupational Physiology 49(2):255-269, Springer Verlag, Germany (Aug. 1982).
Deng, Z.D., et al., "Electric Field Depth-Focality Tradeoff in Transcranial Magnetic Stimulation: Simulation Comparison of 50 Coil Designs," Brain stimulation 6(1):1-13, Elsevier, New York (Jan. 2013).
Depatment of Health and Human Services, 501(k) Letter and Summary for K092476 Body Control System 4M Powered Muscle Stimulator, dated May 7, 2010, 5 pages.
Depatment of Health and Human Services, 501(k) Letter and Summary for K160992 HPM-6000 Powered Muscle Stimulator, dated Oct. 21, 2016, 9 pages.
Depatment of Health and Human Services, 501(k) Letter and Summary for K163415 SlimShape System Powered Muscle Stimulator, dated Apr. 20, 2017, 8 pages.
Depatment of Health and Human Services, 501(k) Letter and Summary for K182106 BTL 799-2T Powered Muscle Stimulator, dated Oct. 23, 2018, 9 pages.
Depatment of Health and Human Services, 501(k) Letter and Summary for K190456 BTL 799-2L Powered Muscle Stimulator, dated Jul. 5, 2019, 9 pages.
Depatment of Health and Human Services, 501(k) Letter and Summary for K192224 BTL 899 Powered Muscle Stimulator, dated Dec. 5, 2019, 11 pages.
Dudley, G. and Stevenson, S., "Use of Electrical Stimulation in Strength and Power Training," Special Problems in Strength and Power Training :426-435 (2003).
Duncan, D., et al., "Noninvasive Induction of Muscle Fiber Hypertrophy and Hyperplasia: Effects of High-Intensity Focused Electromagnetic Field Evaluated in an In-Vivo Porcine Model: A Pilot Study," Aesthetic Surgery Journal 40(5):568-574, Oxford University Press, United States (Apr. 2020).
DuoMAG Magnetic Stimulator, Alien Technik User Manuel, Jun. 26, 2012,48 pages, Version 2.1.
Dybek, T., et al., "Impact of 10 Sessions of Whole Body Cryostimulation on Aerobic and Anaerobic Capacity and on Selected Blood Count Parameters, " Biology of Sport, 29(1):39-43 (Jan. 2012).

(56) References Cited

OTHER PUBLICATIONS

Dynatronics., "Better Rehab Solutions for Better Outcomes," Rehabilitation Products Guide 2.3, 2017, 52 pages.

Effective PEMF Magnetic Fat Reduction Slimming Body Beauty Salon Machine (PEMF Star), Wolfbeauty 1980, PEMF Star, China, Retrieved from the Internet: (URL: https://www.ec21.com/product-details/Effective-PEMF-Magnetic-Fat-Reduction--8928746.html), 2019, 5 pages.

Elamed, Magnetic Therapeutic Apparatus for Running Pulse Magfield small-sized ALMAG-01 Manual, 22 pages, 2020.

Eliminate Stubborn Fat without Surgery or Downtime and Feel Great From Every Angle, Fear No Mirror®, Consultation Guide, Coolsculpting, 2014, 20 pages.

EndyMed PRO, 3 Deep, 3 Dimensional Control of the Target Zone, A Brilliant RadioFrequency Innovation, Eclipse Aesthetics, 2018, 7 Pages.

Energist Ltd—Acquired Chromogenez—Old Account, iLipo—Laser Liposuction (i-Lipo), Video Screenshots, Aug. 10, 2009, 5 pages.

Enoka, R.M., "Muscle Strength and Its Development," Sports Medicine 6:146-168, Springer (Oct. 1988).

Epstein, C., et al., "The Oxford Handbook of Transcranial Stimulation," 773 pages (2008).

European Commission, "Neurogenerative Disorders," 10 pages printed Dec. 27, 2016.

European Patent Office, International Search Report and Written Opinion for International Application No. PCT/IB2016/053930, dated Dec. 12, 2016, 19 pages.

Exilis, Operator's Manual, BTL, 2012, 44 Pages.

Faghri, P.D., et al., "The Effects of Functional Electrical Stimulation on Shoulder Subluxation, Arm Function Recovery, and Shoulder Pain in Hemiplegic Stroke Patients," Archives of Physical Medicine and Rehabilitation 75(1):73-79, W.B. Saunders, United States (Jan. 1994).

Fischer, J., et al., "Precise Subpixel Position Measurement with Linear Interpolation of CMOS Sensor Image Data," The 6th IEEE International Conference on Intelligent Data Acquisition and Advanced Computing Systems, 500-504 (Sep. 2011).

Fisher, R., et al., "ILAE Official Report: a Practical Clinical Definition of Epilepsy," Epilepsia, 55(4):475-482, Blackwell Science, United States (Apr. 2014).

FMS Tesla Stym—AKCE, Medila Cenova nabidika,Price offerc. 191, 24 pages.

Fujimura, K., et al., "Effects of Repetitive Peripheral Magnetic Stimulation on Shoulder Subluxations Caused by Stroke: A Preliminary Study," Neuromodulation : Journal of the International Neuromodulation Society 23(6):847-851, Wiley-Blackwell, United States (Nov. 2020).

Gaines, M., "Slendertone Abdominal Training System, the First FDA-Cleared Abdominal Belt, Introduced in United States by Compex Technologies on Time for Holiday Gift-Giving," Business Wire 44199 (Oct. 2003) 3 pages.

Geddes, L.A., "History of Magnetic Stimulation of the Nervous System," Journal of Clinical Neurophysiology 8(1):3-9, Lippincott Williams & Wilkins, United States (Jan. 1991).

Goetz, S.M., et al., "Coil Design for Neuromuscular Magnetic Stimulation Based on a Detailed 3-D Thigh Model," IEEE Transactions on Magnetics, 50(6):10, IEEE, (Jun. 2014) 10 pages.

Goodman, B.E., "Channels Active in the Excitability of Nerves and Skeletal Muscles Across the Neuromuscular Junction: Basic Function and Pathophysiology," Advances in Physiology Education 32(2):127-135, American Physiological Society, United States (Jun. 2008).

Gorodnichev, R.M., "Magnetic Stimulation of Muscles as New Method to Enhance Their Strength," Velikie Luki State Academy of Physical Culture and Sport, Velikie Luki, 2016, 5 pages.

Gorodnichev, R.M., et al., "The Effect of Electromagnetic Stimulation on the Parameters of Muscular Strength," Human Physiology 40:65-69 (2014).

Halaas, Y. and Bernardy, J., "Biochemical Perspective of Fat Physiology after Application of HIFEM Field Technology: Additional Investigation of Fat Disruption Effects in a Porcine Study," American Society for Laser Medicine and Surgery Abstracts, S4 (2019).

Hamnegard, C.H., et al., "Quadriceps Strength Assessed by Magnetic Stimulation of the Femoral Nerve in Normal Subjects," Clinical Physiology and Functional Imaging, 24(5):276-280, Blackwell, England, (Sep. 2004).

Han, B.H., et al., "Development of four-channel magnetic nerve stimulator," 2001 Proceedings of the 23rd Annual EMBS International Conference, pp. 1325-1327, Turkey (2001).

Han, T.R., et al., "Magnetic Stimulation of the Quadriceps Femoris Muscle: Comparison of Pain With Electrical Stimulation," American Journal of Physical Medicine & Rehabilitation, 85(7):593-599, Lippincott Williams & Wilkins, United States, (Jul. 2006).

Harkey, M.S., "Disinhibitory Interventions and Voluntary Quadriceps Activation: A Systematic Review," Journal of Athletic Training 49(3):411-421, National Athletic Trainers' Association, United States (2014).

Hasala, O., et al., Case Study of Treating Acute Ankle Distortion Using TMS, Charles University, Faculty of Physical Education and Sports, Prague, Czech Republic, 2014, 4 Pages.

Heidland, A., et al., "Neuromuscular Electrostimulation Techniques: Historical Aspects and Current Possibilities in Treatment of Pain and Muscle Waisting," Clinical Nephrology 79 Suppl 1:S12-S23, Dustri-Verlag Dr. Karl Feistle, Germany (Jan. 2012).

Heisel, Jurgen, Physikalische Medizin, Stuttgart: Georg Thieme Verlag KG, 2005. ISBN 3-13-139881-7. p. 159.

Hill, A., "The Influence of Temperature on the Tension Developed in an Isometric Twitch," Proceeding of the Royal Society B 138:349-354, (Sep. 1951).

Hirvonen, H.E., et al., "Effectiveness of Different Cryotherapies on Pain and Disease Activity in Active Rheumatoid Arthritis. A Randomised Single Blinded Controlled Trial," Clinical and Experimental Rheumatology, 24(3):295-301, Clinical and Experimental Rheumatology S.A. S, Italy (May-Jun. 2006).

Hovey, C. and Jalinous, R., "The Guide to Magnetic Stimulation" Magstim, Pioneers in Nerve Stimulation and Monitoring, pp. 1-44 (2016).

Hovey, C., et al., "The Guide to Magnetic Stimulation," The Magstim Company Limited, 48 pages (Jul. 2006).

Huang, Y.Z., et al., "Theta Burst Stimulation of the Human Motor Cortex," Neuron 45(2):201-206, Cell Press, United States (Jan. 2005).

I-Lipo by Chromo genex, i-Lipo Ultra is the Intelligent, Non-Surgical Alternative to Liposuction, 2011, 2 pages.

Increasing Physiotherapy Presence in Cosmetology, Spa Inspirations, Jan. 2012, pp. 34-35.

Irazoqui P., Post Grant Review of U.S. Pat. No. 10,695,576, PTAB-PGR2021-00024, filed as EX1085, Dec. 14, 2020, 25 pages.

Iskra Medical, "TESLA Stym—Functional Magnetic Stimulation FMS," Nov. 2013, http://ww.iskramedical.eu/magneto-therapy-medical/tesla-stym, 5 pages.

Iskra Medical, Magneto System, 2012, 2 pages.

Izumiya, Y., et al., "Fast/Glycolytic Muscle Fiber Growth Reduces Fat Mass and Improves Metabolic Parameters in Obese Mice", Cell Metabolism 7(2):159-172, Cell Press, United States (Feb. 2008).

Jacob, C., et al., "High Intensity Focused Electro-Magnetic Technology (HIFEM) for Non-Invasive Buttock Lifting and Toning of Gluteal Muscles: A Multi-Center Efficacy and Safety Study," Journal of Drugs in Dermatology 17(11):1229-1232, Physicians Continuing Education Corporation, United States (Nov. 2018).

Jacob, C.I., et al., "Safety and Efficacy of a Novel High-Intensity Focused Electromagnetic Technology Device for Noninvasive Abdominal Body Shaping," Journal of Cosmetic Dermatology, 17(5):783-787, Blackwell Science, United States (Oct. 2018).

Jacobm C., and Paskova, "A Novel Non-Invasive Technology Based on Simultaneous Induction of Changes in Adipose and Muscle Tissues: Safety and Efficacy of a High Intensity Focused Electro-Magnetic (HIFEM) Field Device Used For Abdominal Body Shap-

(56) References Cited

OTHER PUBLICATIONS ing," American Society for Laser Medicine and Surgery, 2018 Electronic Posters (ePosters) Town Hall and ePosters, 369, p. 1, Wiley Periodicals, Inc. (2018).

Jeanrenaud, B., "Lipid components of adipose tissue, " Handbook of Physiology, Adipose Tissue, Chapter 15, 8 Pages.

Johari Digital Healthcare Ltd., 510(k)—K062439 Powertone Letter from Department of Health and Humane Services Summary, Public Health Service, Jan. 8, 2007, 6 pages.

Johari Digital Healthcare Ltd., "510(k)—K131291 Torc Body Letter from Department of Health and Humane Services", Public Health Service, Jun. 14, 2013, 10 pages.

Johari Digital Healthcare Ltd., K131291 510(k) Summary, TorcBody, All pages (Jun. 2013) 10 pages.

Jutte, L.S., et al., "The Relationship Between Intramuscular Temperature, Skin Temperature, and Adipose Thickness During Cryotherapy and Rewarming," Archives of Physical Medicine and Rehabilitation, 82(6):845-850, W.B. Saunders, United States (Jun. 2001).

Katuscakova, Z.L., et al., High Induction Magnet Therapy in Rehabilitation, Department of Physiactric Rehabilitation, 2012, 72 pages.

Katz, B., et al., "Changes in Subcutaneous Abdominal Fat Thickness Following High-Intensity Focused Electro-Magnetic (HIFEM) Field Treatments: A Multi Center Ultrasound Study," American Society for Laser Medicine and Surgery Abstracts, 360-361 (2018).

Katz, B., et al., "Ultrasound Assessment of Subcutaneous Abdominal Fat Thickness after Treatments with a High-Intensity Focused Electromagnetic Field Device: A Multicenter Study," Dermatologic Surgery 45(12):1542-1548, Williams & Wilkins, United States (Dec. 2019).

Kavanagh, S., et al., "Use of a Neuromuscular Electrical Stimulation Device for Facial Muscle Toning: A Randomized, Controlled Trial," Journal of Cosmetic Dermatology 11(4):261-266, Blackwell Science, United States (Dec. 2012).

Kent, D,E. and Jacob, C.I., Simultaneous Changes in Abdominal Adipose and Muscle Tissues Following Treatments by High-Intensity Focused Electromagnetic HIFEM Technology-Based Device: Computed Tomography Evaluation, Journal of Drugs in Dermatology 18(11):1098-1102, Physicians Continuing Education Corporation, United States (Nov. 2019).

Kent, D., and Jacob C., "Computed Tomography (CT) Based Evidence of Simultaneous Changes in Human Adipose and Muscle Tissues Following a High Intensity Focused Electro-Magnetic Field (HIFEM) Application: A New Method for Non-Invasive Body Sculpting," American Society for Laser Medicine and Surgery Abstracts, p. 370 (2018).

Kim, Y.H., et al., "The Effect of Cold Air Application on Intra-Articular and Skin Temperatures in the Knee," Yonsei Medical Journal, 43(5):621-626, Yonsei University, Korea (South) (Oct. 2002).

Kinney, B.M. and Lozanova P., "High Intensity Focused Electromagnetic Therapy Evaluated by Magnetic Resonance Imaging: Safety and Efficacy Study of a Dual Tissue Effect Based Non-Invasive Abdominal Body Shaping," Lasers in Surgery and Medicine 51(1):40-46, Wiley-Liss, United States (Jan. 2019).

Kolin, A., et al., "Stimulation of Irritable Tissues by means of an Alternating Magnetic Field," Proceedings of the Society for Experimental Biology and Medicine 102:251-253, Blackwell Science, United States (Oct. 1959).

Korman, P., et al., "Temperature Changes in Rheumatoid Hand Treated With Nitrogen Vapors and Cold Air," Rheumatology International, 32(10):2987-2992, Springer International, Germany (Oct. 2012).

Kotz, Y., "Theory and Practice of Physical Culture," Training of Skeletal Muscle With Method of Electrostimulation, 64-67 (Mar. 1971).

Kotz, Y., "Theory and Practice of Physical Culture," Training of Skeletal Muscle With Method of Electrostimulation, 66-72 (Apr. 1971).

Kumar, N. and Agnihotri, R.C., "Effect of Frequency and Amplitude of Fes Pulses on Muscle Fatigue During Toning of Muscles," Journal of Scientific and Industrial Research 67(4):288-290, (Apr. 2008).

Lampropoulou, S.I., et al., "Magnetic Versus Electrical Stimulation in the Interpolation Twitch Technique of Elbow Flexors," Journal of Sports Science and Medicine, 11(4):709-718, Dept. of Sports Medicine, Medical Faculty of Uludag University, Turkey (Dec. 2012).

Langford, J. and McCarthy, P.W., "Randomised controlled clinical trial of magnet use in chronic low back pain; a pilot study," Clinical Chiropractic 8(1):13-19, Elsevier (Mar. 2005).

Lee, P.B., et al., "Efficacy of Pulsed Electromagnetic Therapy for Chronic Lower Back Pain: a Randomized, Double-blind, Placebcontrolled Study," The Journal of International Medical Research 34(2):160-167, Cambridge Medical Publications, England (Mar.-Apr. 2006).

Leitch, M., et al., "Intramuscular Stimulation of Tibialis Anterior in Human Subjects: The Effects of Discharge Variability on Force Production and Fatigue," Physiological Reports 5(15):e13326, Wiley Periodicals, Inc., United States (Aug. 2017) 7 pages.

Leon-Salas, W.D., et al., "A Dual Mode Pulsed Electro-Magnetic Cell Stimulator Produces Acceleration of Myogenic Differentiation," Recent Patents on Biotechnology 7(1):71-81, Bentham Science Publishers, United Arab Emirates (Apr. 2013).

Letter from Department of Health and Human Services, Public Health Service, Dec. 19, 2014, 7 pages.

Lin, V.W., et al., "Functional Magnetic Stimulation for Conditioning of Expiratory Muscles in Patients with Spinal Cord Injury.," Archives of Physical medicine and Rehabilitation 82(2):162-166, W.B. Saunders, United States (Feb. 2001).

Lin, V.W., et al., "Functional Magnetic Stimulation for Restoring Cough in Patients With Tetraplegia," Archives of Physical Medicine and Rehabilitation, 79(5):517-522, W.B. Saunders, United States, (May 1998).

Lin, V.W., et al., "Functional Magnetic Stimulation of Expiratory Muscles: a Noninvasive and New Method for Restoring Cough," Journal of Applied Physiology (1985), 84(4):1144-1150, American Physiological Society, United States, (Apr. 1998).

Lin, V.W., et al., "Functional Magnetic Stimulation of the Respiratory Muscles in Dogs," Muscle & Nerve 21(8):1048-1057, John Wiley & Sons, United States (Aug. 1998).

Lin, V.W., et al., "Functional Magnetic Stimulation: A New Modality for Enhancing Systemic Fibrinolysis," Archives of Physical Medicine and Rehabilitation 80(5):545-550, W.B. Saunders, United States (May 1999).

Linehan, C., et al., Brainwave the Irish Epilepsy Assoication, "The Prevalence of Epilepsy in Ireland" Summary Report, pp. 1-8 (May 2009).

Lotz, B.P., et al., "Preferential Activation of Muscle Fibers with Peripheral Magnetic Stimulation of the Limb," Muscle & Nerve, 12(8):636-639, John Wiley & Sons, United States (Aug. 1989).

Madariaga, V.B., et al., "[Magnetic Stimulation of the Quadriceps: Analysis of 2 Stimulators Used for Diagnostic and Therapeutic Applications]," Archives De Bronconeumologi'a, 43(7):411-417, Elsevier Espana, Spain, (Jul. 2007).

Maffiuletti, N.A., et al., "Activation of Human Plantar Flexor Muscles Increases After Electromyostimulation Training," Journal of Applied Physiology 92(4):1383-1392, American Physiological Society, United States (Nov. 2001).

Maffiuletti, N.A., et al., "The Effects of Electromyostimulation Training and Basketball Practice on Muscle Strength and Jumping Ability," International journal of sports medicine 21(6):437-443, Thieme, Germany (Aug. 2000).

MAG and MORE Gmbh, Magnetic and Life Science System, Power Mag, 12 Pages.

MAG Expert, 2 pages.

Mag Venture, Magnetic Stimulation, Accessories Catalogue, Accessories Catalogue, 2011, 54 pages.

Magstim Company Limited, K051864 510(k) Summary, Magstim Rapid and Magstim Super Rapid, All pages (Dec. 2005) 6 pages.

Magstim Company US, LLC, K060847 510(k) Summary, Magstim Model 200-2 with Double 70mm Remote Coil, All pages (Sep. 2006) 3 pages.

(56) References Cited

OTHER PUBLICATIONS

Magstim Corporation US, K992911 510(k) Summary, Magstim Rapid, 3 pages (Jan. 2000).
MagVenture, MagPro® by MagVenture®, Versatility in Magnetic Stimulation, World Leading Transcranial Magnetic Stimulation Systems, 2011, 6 Pages.
Man, W.D-C., et al., "Magnetic Stimulation for the Measurement of Respiratory and Skeletal Muscle Function," The European Respiratory Journal 24(5):846-60, European Respiratory Society, England (2004).
Manstein, D., et al., "Selective Cryolysis: A Novel Method of Non-Invasive Fat Removal," Lasers in Surgery and Medicine, 40(9):595-604, Wiley-Liss, United States (Nov. 2008).
Mantovani, A., et al., "Applications of Transcranial Magnetic Stimulation to Therapy in Pyschiatry," Psychiatric Times 21(9), Intellisphere, 29 pages (Aug. 2004).
Markov, M.S., "Pulsed Electromagnetic Field Therapy History, State of the Art and Future," Environment Systems and Decisions 27(4):465-475, Springer (Dec. 2007).
MecoTec Freezing Technology, Presentation Cryoair Whole Body Cryotherapy Chambers, Germany, Jul. 2017, 52 Pages.
Medline, Body Temperature Norms, 2 pages (Year: 2019).
Mettler J.A., et al., "Low-Frequency Electrical Stimulation With Variable Intensity Preserves Torque," Journal of Electromyography and Kinesiology : Official Journal of the International Society of Electrophysiological Kinesiology 42:49-56, Oxford:Elsevier, England (Oct. 2018).
Mogyoros, I., et al., "Strength-Duration Properties of Human Peripheral Nerve," Brain 119(Pt 2):439-447, Oxford University Press, England (Apr. 1996).
Morrissey. M., "Electromyostimulation from a Clinical Perspective," Sports Medicine 6(1):29-41, Springer International, New Zealand (Aug. 1988).
Mulholland, R.S., Synergistic Multi-polar Radiofrequency and Pulsed Magnetic Fields in the Non-Invasive Treatment of Skin Laxity and Body Contouring, 4 pages.
Mustafa, B., "Design and Construction of a Low Cost dsPIC Controller Based Repetitive Transcranial Magnetic Stimulator TMS," Journal of medical systems 34(1):15-24, Kluwer Academic/Plenum Publishers, United States (2010).
Nadler, S.F., et al., "The Physiologic Basis and Clinical Applications of Cryotherapy and Thermotherapy for the Pain Practitioner," Pain Physician, 7(3):395-399, American Society of Interventional Pain Physicians, United States (Jul. 2004).
Nassab, R., "The Evidence Behind Noninvasive Body Contouring Devices," Aesthetic Surgery Journal, 35(3):279-293, Oxford University Press, England (Mar. 2015).
National Institute of Neurological Disorders and Stroke, Epilepsy Information Page, www.ninds.nih.gov/disorders/epilepsy/epilepsy.htm, pp. 1-6 (Feb. 1, 2016).
Neotonus, Inc., K973096 510(k) Summary, Neotonus Model 100 Muscle Stimulator System, (Jun. 1998) 4 pages.
Neotonus, Inc., K973929 510(k) Summary and FDA Correspondence, Neotonus, 5 pages (May 1998).
Neuro Star, TMS Therapy, Bringing Hope to Patients with Depression, 2013, 6 Pages.
Neurosoft Ltd., "Neurosoft—Neuro-MS Transcranial Magnetic Simulator Technical Manual," All pages (Nov. 2014).
Neurosoft, Ivanovo, Since 1992, Magnetic Stimulator, NEURO-MS, Technical Manual, Neurosoft Ltd, Ivanovo, Russia, 2006, 67 Pages.
Nexstim NBS System, Navigated Brain Stimulation, Noninvasive, direct cortical mapping, 2012, 5 Pages.
Neyroud, D., et al., "Comparison of Electrical Nerve Stimulation, Electrical Muscle Stimulation and Magnetic Nerve Stimulation to Assess the Neuromuscular Function of the Plantar Flexor Muscles," European journal of applied physiology 115(7):1429-1439, Springer-Verlag, Germany (2015).
Nielsen, J.F., et al., "A New High-frequency Magnetic Stimulator With an Oil-cooled Coil," Journal of Clinical Neurophysiology 12(5):460-467, Lippincott Williams & Wilkins, United States (Sep. 1995).
Non Final Office Action dated Jun. 23, 2017, in United States U.S. Appl. No. 15/473,390, Schwarz, T., et al., filed Mar. 29, 2017, 10 pages.
Notice of Allowance dated Mar. 24, 2021 for U.S. Appl. No. 17/087,850 (pp. 1-8).
Novickij, V., et al., "Compact Microsecond Pulsed Magnetic Field Generator for Application in Bioelectronics," Elektronika ir Elektrotechnika 19(8):25-28 (Oct. 2013).
Novickij, V., et al., "Design and Optimization of Pulsed Magnetic Field Generator for Cell Magneto-Permeabilization," Elektronika ir Elektrotechnika(Electronics and Electrical Engineering) 23(2):21-25 (Apr. 2017).
Novickij, V., et al., "Magneto-Permeabilization of Viable Cell Membrane Using High Pulsed Magnetic Field," IEEE Transactions on Magnetics 51(9), 5 pages (Sep. 2015).
Novickij, V., et al., "Programmable Pulsed Magnetic Field System for Biological Applications," IEEE Transactions on Magnetics 50(11):5 (Nov. 2014) 4 pages.
NPF Electroapparat, Amplipulse-5Br Manual, 2020, 55 pages.
Obsluze, N.K.,Usage Instructions, User's Manual, Device for high-induction magnetic stimulation of type designation:Saluter Moti, 2016,88 Pages.
Oliveira, P.DE., et al., "Neuromuscular Fatigue After Low-and Medium-frequency Electrical Stimulation in Healthy Adults," Muscle & Nerve 58(2):293-299, John Wiley & Sons, United States (Aug. 2018).
Operating Manual, Magstim R Air-Cooled Double 70mm Coil System, 1600-23-04, The Magstim Company Limited, 1999, 18 Pages.
Operating Manual, MAGSTIM, Model 200, P/N 3001-01, Double 70mm, Remote Coil, P/N 3190-00, The Magstim Company Limited, 2006, 32 pages.
Operating Manual: Magstim $D70^2$ Coil, MOP06-EN, Revision 01, The Magstim Company Limited, Feb. 2012, 14 Pages.
Operating Manual: Magstim Magstim $200^2$, MOP01-EN, Revision 01, The Magstim Company Limited, Sep. 2011, 25 Pages.
Operating Manual: Magstim R, 2nd, Generation Coil Family, 3100-23-02, Magstim Coils, The Magstim Company Limited, Nov. 2002, 14 Pages.
Operating Manual: Magstim R, Bistim System, P/N 3234-23-01, The Magstim Company Limited, Nov. 2004, 30 Pages.
Operating Manual: Magstim R, Coils & Accessories, 1623-23-07, Magstim Coils & Accessories, May 2010, 24 Pages.
Operating Manual: Magstim, Magstim Alpha Coil Range, MOP11-EN, Revision 01, Oct. 2012, 18 Pages.
Operating Manual: Magstim, Magstim $Bistim^2$, MOP02-EN, Revision, The Magstim Company Limited, 01, Sep. 2011, 27 Pages.
Operating Manual: Magstim, RAPID2, P/N 3576-23-09, The MAGSTIM Company LTD, Nov. 2009, 61 Pages.
Operator's Manual: BTL Emsculpt, BTL Industries Ltd, United Kingdom, 2018, 35 pages.
Operator's Manual: BTL, HPM-6000U, BTL Industries Ltd, United Kingdom, Dec. 2016, 36 pages.
Otte, J.S., et al., "Subcutaneous Adipose Tissue Thickness Alters Cooling Time During Cryotherapy," Archives of Physical Medicine and Rehabilitation, 83(11):1501-1505, W.B. Saunders, United States (Nov. 2002).
Pain Management Technologies, "Pain Management Technologies Product Catalog," (2012) 24 pages.
Papimi, For Scientific Research, Pap Ion Magnetic Inductor, Presentation, Magnetotherapeutic Device, Nov. 2009, 61 Pages.
Periso SA, CTU mega Diamagnetic Pump 20: Device For Diamagnetic Therapy, CTU Mega 20 Manual, dated Aug. 28, 2019, 44 pages, Pazzallo Switzerland.
Photograph, Alleged Photograph of Components of a Salus Talent Pop Double Device with An Aalleged Manufacture date of Nov. 14, 2012, 1 page.
Physiomed, MAG-Expert, Physiomed Manual, Dec. 19, 2012, 63 pages.

(56) References Cited

OTHER PUBLICATIONS

Physiomed, Physiomed Mag-Expert, Physiomed Catalog, pp. 81-83.
Platil, A., "Magnetopneumography Using Optical Position Reference," Sensor Letters 11(1):69-73, ResearchGate (2013).
Podebradsky.K., et al., Clinical study of high-inductive electromagnetic stimulator SALUS talent, 2010, 8 pages.
Pohanka, J., et al., "An Embedded Stereovision System: Aspects of Measurement Precision," 12th Biennial Baltic Electronics Conference, pp. 157-160 (Oct. 2010).
Polk, C., "Therapeutic Applications of Low-Frequency Sinusoidal and Pulsed Electric and Magnetic Fields," The Biomedical Engineering Handbook, vol. 1, 2000, Second edition, CRC Press LLC, pp. 1625-1636.
Polkey M.I., et al., "Functional Magnetic Stimulation of the Abdominal Muscles in Humans," American Journal of Respiratory and Critical Care Medicine, 160(2):513-522, American Thoracic Society, United States (Aug. 1999).
Polkey, M.I., et al., "Quadriceps Strength and Fatigue Assessed by Magnetic Stimulation of the Femoral Nerve in Man," Muscle Nerve, 19(5):549-555, John Wiley & Sons, United States, (May 1996).
Pollogen, TriLipo MED Procedure, Brochure, dated Apr. 7, 2021, 76 pages.
Porcari, J.P., et al., "Effects of Electrical Muscle Stimulation on Body Composition, Muscle Strength, and Physical Appearance," Journal of Strength and Conditioning Reasearch 16(2):165-172, Human Kinetics Pub., United States (May 2002).
Porcari, J.P., et al., "The Effects of Neuromuscular Electrical Stimulation Training on Abdominal Strength, Endurance, and Selected Anthropometric Measures," Journal of Sports Science and Medicine 4(1):66-75, Dept. of Sports Medicine, Turkey (Mar. 2005).
Pribula, O. and Fischer, J., "Real Time Precise Position Measurement Based on Low-Cost CMOS Image Sensor," IEEE, 5 pages (2011).
Pribula, O., et al., "cost-effective Image Acquisition System for Precise Pc-based Measurements," Przeglad Elektrotechniczny (Electrical Review), 2011, pp. 259-263.
Pribula, O., et al., "Optical Position Sensor Based on Digital Image Processing: Magnetic Field Mapping Improvement," Radioengineering 20 (1):55-60, (Apr. 2011).
Pribula, O., et al., "Real-Time Video Sequences Matching Spatio-Temporal Fingerprint," IEEE, 911-916 (Jun. 2010).
Prouza, O., "Ex-Post Analyza Spot Rebnich Dani," 58 pages, (2008).
Prouza, O., "Targeted Radiofrequency Therapy for Training Induced Muscle Fatigue—Effective or Not?," International Journal of Physiotherapy 3(6):707-710 (Dec. 2016).
Prouza, O., et al., "High-Intensity Electromagnetic Stimulation Can Reduce Spasticity in Post-Stroke Patients," International Journal of Physiotherapy 5(3):87-91 (2018).
PTAB-IPR2021-00296, U.S. Pat. No. 10,493,293, Petition for Inter Partes Review, Dec. 14, 2020, 117 pages.
PTAB-IPR2021-00312, U.S. Pat. No. 10,478,634, Petition for Inter Partes Review, Dec. 14, 2020, 108 pages.
PTAB-PGR2021-00015, U.S. Pat. No. 10,709,895, Petition for Post-Grant Review, Dec. 14, 2020, 140 pages.
PTAB-PGR2021-00016, U.S. Pat. No. 10,709,895, Petition for Post-Grant Review, Dec. 14, 2020, 144 pages.
PTAB-PGR2021-00017, U.S. Pat. No. 10,632,321, Petition for Post-Grant Review, Dec. 14, 2020, 121 pages.
PTAB-PGR2021-00018, U.S. Pat. No. 10,632,321, Petition for Post-Grant Review, Dec. 14, 2020, 140 pages.
PTAB-PGR2021-00020, U.S. Pat. No. 10,695,575, Petition for Post-Grant Review, Dec. 14, 2020, 112 pages.
PTAB-PGR2021-00021, U.S. Pat. No. 10,695,575, Petition for Post-Grant Review, Dec. 14, 2020, 117 pages.
PTAB-PGR2021-00022, U.S. Pat. No. 10,709,894, Petition for Post-Grant Review, Dec. 14, 2020, 119 pages.
PTAB-PGR2021-00023, U.S. Pat. No. 10,709,894, Petition for Post-Grant Review, Dec. 14, 2020, 136 pages.
PTAB-PGR2021-00024, U.S. Pat. No. 10,695,576, Petition for Post-Grant Review, Dec. 14, 2020, 136 pages.
PTAB-PGR2021-00025, U.S. Pat. No. 10,695,576, Petition for Post-Grant Review, Dec. 14, 2020, 135 pages.
Publication of Medical Device Manufacturing Approval of Salus-TALENT-Pro, approval date Mar. 11, 2014, 39 pages.
Quick Start Manuals, Magstim Super Rapid Plus Quick Start, Aalto TMS Laboratory, Aalto School of Science, 2013, 7 Pages.
Radakovic T. and Radakovic N., "The Effectiveness of the Functional Magnetic Stimulation Therapy in Treating Sciatica Syndrome," Open Journal of Therapy and Rehabilitation 3(3):63-69 (2015).
Reaction User Manual, Viora, Doc No. MK-004 A, 2008, 53 Pages.
Reshaping the Future of Your Practice, Cool sculpting, A Revolution in Aesthetic Fat Reduction, 2011, 10 Pages.
Riehl., M., "Chapter 3: TMS Stimulator Design" The Oxford Handbook of Transcranial Stimulation, Wasserman, E.M., ed., pp. 13-23, Oxford University Press, 26 pages, United Kingdom (2008).
Roots, H., and Ranatunga, K.W., "An Analysis of the Temperature Dependence of Force, During Steady Shortening at Different Velocities, in (Mammalian) Fast Muscle Fibres," Journal of Muscle Research and Cell Motility 29(1):9-24, Springer, Netherlands (Jun. 2008).
Rutkove, S., "Effects of Temperature on Neuromuscular Electrophysiology," Muscle & Nerve 24(7):867-882, John Wiley & Sons, United States (Jul. 2001).
Salus Talent Pop, The first sales bill, Authorization No. 20120221-41000096-66667961, 2 pages, (Feb. 2012).
Salus Talent Pro, Specification, 2 pages.
Salus Talent-A, Remed, User Guide, High Intensity Electro Magnetic Field Therapy, 2017, 37 pages.
Salus Talent—Pop Double, 2 pages.
Salus Talent, a Vertice and Talos, Drott, 6 pages.
Salus Talent, Deep Penetrating Electro-Magnetic Stimulator, CR Technology, 4 pages.
Salus Talent, Deep Penetrating Electro-Magnetic Stimulator, Rehabilitation Medical Company, New choice, new satisfaction, Talent, 4 pages.
Salus Talent, Electro Magnetic Stimulator, CR Technology, 9 Pages.
Salus-Talent, Device for Deep Electromagnetic Stimulation, Nowosc, Fizjoterapia, 6 Pages.
Salus, Talent Pro, The Birth of Salus Talent Pro inspired by 10 Years of Experience, Specification, Rehabilitation Medical Company, Slimon, 2 pages.
Salus, Talent Pro, The World's 1st Development 3 Tesla, 2Channel Magnetic field Therapy, Slimon, 10 pages.
Sargeant, A.J., "Effect of Muscle Temperature on Leg Extension Force and Short-term Power Output in Humans," European Journal of Applied Physiology and Occupational Physiology 56(6):693-698, Springer Verlag, Germany (Sep. 1987).
Schaefer, D.J., et al., "Review of Patient Safety in Time-Varying Gradient Fields," Journal of Magnetic Resonance Imaging, 12:20-29, Wiley-Liss, United States (Jul. 2000).
Scientific & Clinical Background of (MP)2®—A synergy between Multi polar RF and Pulsed Magnetic Field developed by Venus Concept. Prof. Yeouda Edoute M.D, Ph,D, 2 pages.
Shimada, Y., et al., "Effects of therapeutic magnetic stimulation on acute muscle atrophy in rats after hindlimb suspension," Biomedical Research 27(1):23-27, Biomedical Research Foundation, Japan (Feb. 2006).
Silinskas, V., et al., "Effect of Electrical Myostimulation on the Function of Lower Leg Muscles," Journal of strength and Conditioning Research 31(6):1577-1584, Human Kinetics Pub, United States (2017).
Sport-Elec S.A., K061914 510(k) Summary, Sport-Elec, 5 pages (Jul. 2007).
Sport-Elec S.A., K081026 510(k) Summary, Sport-Elec, 5 pages (Nov. 2008).
Starbelle, PEMF Shape, Webpage, dated Feb. 10, 2020, 3 pages, available at http://www.starbelle.cn/info/PEMFShape.html.
Stedman, T.L., "Aponeurosis—Apparatus," in Stedman's Medical Dictionary, 27th Edition, Pugh, M.B., ed., pp. 113-114, Lippincott Wiliams & Wilkins, Baltimore, MD (2000).

(56) References Cited

OTHER PUBLICATIONS

Struppler, A., et al., "Facilitation of Skilled Finger Movements by Repetitive Peripheral Magnetic Stimulation (RPMS)—A New Approach In Central Paresis.," NeuroRehabilitation 18(1):69-82, IOS Press, Amsterdam (2003).

Struppler, A., et al., "Modulatory Effect of Repetitive Peripheral Magnetic Stimulation on Skeletal Muscle Tone in Healthy Subjects: Stabilization of the Elbow Joint," Experimental Brain Research 157(1):59-66, Springer Verlag, Germany (Feb. 2004).

Suarez-Bagnasco, D., et al., "The Excitation Functional for Magnetic Stimulation of Fibers.," Annual International Conference of the IEEE Engineering in Medicine and Biology Society, IEEE Engineering in Medicine and Biology Society, Annual International Conference, 2010:4829-4833, IEEE, United States (2010).

Swallow, E.B., et al., "A Novel Technique for Nonvolitional Assessment of Quadriceps Muscle Endurance in Humans," Journal of Applied Physiology 103(3):739-746, American Physiological Society, United States (Sep. 2007).

Szecsi, J., et al., "A Comparison of Functional Electrical and Magnetic Stimulation for Propelled Cycling of Paretic Patients," Archives of Physical Medicine and Rehabilitation, 90(4):564-570, W.B. Saunders, United States, (Apr. 2009).

Szecsi, J., et al., "Force-pain Relationship in Functional Magnetic and Electrical Stimulation of Subjects With Paresis and Preserved Sensation," Clinical Neurophysiology, 121(9):1589-1597, Elsevier, Netherlands, (Sep. 2010).

Taylor, J.L, "Magnetic Muscle Stimulation Produces Fatigue Without Effort," Journal of Applied Physiology (1985), 103(3):733-734, American Physiological Society, United States, (Sep. 2007).

Tesla Stym, Iskra Medical, Tone the inner muscle with FMS Functional Magnetic Stimulation, 2013, 4 pages.

The Burn Centre Care, Education, 3 pages, printed from internet Nov. 13, 2017.

The Magstim Company Ltd, K080499 510(k) Summary, Magstim Double 70mm Air Film Coil, 5 pages (Dec. 2008).

The Magstim Company Ltd., K130403 510(k) Summary, Magstim D702 coil, 8 pages (Aug. 2013).

Thermi Launches Arvati, powered by Thermi, with newest advances in True Temperature Controlled Radiofrequency Technology, 5 pages (2018).

Thermi Smooth TM 250, High Power Temperature Controlled Radio Frequency, Thermi Aesthetics, 25 pages.

Thompson, M.T., "Inductance Calculation Techniques—Part II: Approxmiations and Handbook Methods," Power Control and Intelligent Motion, 11 pages (Dec. 1999) http://www.pcim.com/.

Thompson, M.T., "Inductance Calculation Techniques—Part II: Classical Methods," Power Control and Intelligent Motion, 25(12):40-45, (Dec. 1999) http://www.pcim.com/.

Tomek, J., et al., "Magnetopneumography—Incorporation of optical position reference," Journal of Electrical Engineering, 4 pages (2012).

Torbergsen, T., "Abstracts of the International Course and Symposium in Single Fibre EMG and Quantitative EMG Analysis. Tromsø, Norway, Jun. 4-8, 1984," Muscle & Nerve 9(6):562-574, John Wiley & Sons, United States (Jul.-Aug. 1986).

TSEM Med Swiss SA, Diamagnetic Therapy: A Revolutionary Therapy, CTU Mega 20 Catalogue, dated 2016, 24 pages, Lugano Switzerland.

U.S. Appl. No. 62/331,060, inventor Schwarz, T., filed May 3, 2016 (Not Published) 32 pages.

U.S. Appl. No. 62/331,072, inventor Schwarz, T., filed May 3, 2016 (Not Published) 34 pages.

U.S. Appl. No. 62/331,088, inventor Schwarz, T., filed May 3, 2016 (Not Published) 38 pages.

U.S. Appl. No. 62/333,666, inventor Schwarz, T., filed May 9, 2016 (Not Published) 39 pages.

U.S. Appl. No. 62/357,679, inventor Schwarz, T., filed Jul. 1, 2016 (Not Published) 22 pages.

U.S. Appl. No. 62/440,905, inventors Schwarz, T. et al., filed Dec. 30, 2016 (Not Published) 32 pages.

U.S. Appl. No. 62/440,912, inventors Schwarz, T. et al., filed Dec. 30, 2016 (Not Published) 19 pages.

U.S. Appl. No. 62/440,922, inventor Schwarz, T., filed Dec. 30, 2016 (Not Published) 10 pages.

U.S. Appl. No. 62/440,936, inventor Schwarz, T., filed Dec. 30, 2016 (Not Published) 9 pages.

U.S. Appl. No. 62/440,940, inventor Schwarz, T, filed Dec. 30, 2016 (Not Published) 8 pages.

U.S. Appl. No. 62/441,805, inventor Prouza, O., filed Jan. 3, 2017 (Not Published) 26 pages.

U.S. Appl. No. 62/786,731, inventor Schwarz, T., filed Dec. 31, 2018 (Not Published) 115 pages.

U.S. Appl. No. 62/351,156, inventor Schwarz, T., filed Jun. 16, 2016 (Not Published) 41 pages.

Ultra Slim Professional, The very best body Contouring, Wardphotonics LLC, 2018, 16 pages.

Unique Multi-Treatment Platform For, Feminine Health, Venus Fiore, Jul. 24, 2018, 12 pages.

Urban J., "Magnetotherapy and Physiotherapy", 40 pages.

Uro Diagnostic Clinic, Now in UDC, Automated pelvic floor muscle training, QRS International AG, 16 Pages.

USER Guide, Salus Talent Pro, REMED, High Intensity Electro magnetic Field Therapy-2 Channel, 2017, Version M-1.0.0, 45 pages.

User Guide, Salus Talent, REMED, High Intensity Electro magnetic Field Therapy, Version. M-1.0.0, 2017, 40 pages.

User Guide: Mag Venture, Magpro family, MagPro R30, MagPro R30 with MagOption, MagPro X100, MagPro X100 with MagOption, MagPro software v.5.0, US-edition, MagPro family User Guide, 2010, 52 Pages.

User Manual: Electro-magnetic Stimulator, SALUS-TALENT, Version 1.00, Rehabilitation Medical Company,2013, 34 Pages.

User Manual: Regenetron PRO, System Information, Regenetron PRO User Manual, Nov. 2014, 7 Pages.

User's Manual: BTL-6000, Super Inductive System Elite, BBTL Industries Ltd, United Kingdom, Sep. 2016, 36 pages.

Vance, C., et al., "Effects of Transcutaneous Electrical Nerve Stimulation on Pain, Pain Sensitivity, and Function in People with Knee Osteoarthritis," Physical Therapy 92:898-910 (2012).

Vanquish Operator's Manual, BTL, 2012, 48 Pages.

Venus Concept Ltd., VenusFreeze MP2, User Manual, dated Jun. 2012, 46 pages.

Venus Concept Ltd., VenusViva, User Manual, dated Aug. 2013, 51 pages.

Venus Legacy, Featuring LiftFX and SculptFX, Venus Concept, Delivering the Promise, 24 pages.

Venus Legacy, User Manual International, 2009, Venus Concept, 49 pages.

VenusFreeze, Experience the Energy, Venus Concept, Delivering the Promise, 2 pages.

Verges S., et al., "Comparison of Electrical and Magnetic Stimulations to Assess Quadriceps Muscle Function," Journal of Applied Physiology (1985), 106(2):701-710, American Physiological Society, United States, (Feb. 2009).

Wada, K., et al., "Design and Implementation of Multi-Frequency Magnetic Field Generator Producing Sinusoidal Current Waveform for Biological Researches," IEEE, 9 pages (2016).

Ward, A.R. and Shkuratova, N., "Russian Electrical Stimulation: The Early Experiments," Physical therapy, 82(10):1019-1030, Oxford University Press, United States (2002).

Wasilewski, M.L., Academy of Aesthetic and Anti-Aging Medicine, Application of magnetic fields with deep stimulation in the fight against local obesity of lower limbs, BTL, 2012, 4 pages.

Web MD, what is normal body temperature? 3 pages, printed Mar. 4, 2019.

Weight to volume aluminum, 2 pages. printed from internet Sep. 25, 2018.

Weight to volume copper, 2 pages printed from internet Sep. 25, 2018.

Weiss, R.A., et al., "Induction of Fat Apoptosis by a Non-Thermal Device: Mechanism of Action of Non-Invasive High-Intensity Electromagnetic Technology in a Porcine Model," Lasers in surgery and medicine 51(1):47-53, Wiley-Liss, United States (Jan. 2019).

(56) References Cited

OTHER PUBLICATIONS

Weng, O., "Electromagnetic Activation of the Calf Muscle Pump," UMI Dissertation Publishing (2014) 267 pages.

Werner, R., Magnetotherapy, Pulsating energy resonance therapy, 107 pages (Jun. 2007).

Yacyshy, A.F., et al., "The Inclusion of Interstimulus Interval Variability Does Not Mitigate Electrically-evoked Fatigue of the Knee Extensors," European Journal of Applied Physiology 120(12):2649-2656, Springer-Verlag, Germany (Sep. 2020).

Z Wave, Instructions for Use, Zimmer Aesthetic Division, Version 5, 44 pages.

Zao Okb Ritm, Electroneurostimulants, Transdermal Scenar—NT Instructions, 24 Pages (Nov. 2013).

Zao Okb Ritm, Percutaneous Electrical Stimulators With Individual Biofeedback Dosing Impact on Reflex Zones, 43 pages (Feb. 2, 2017).

Zelickson, B., et al., "Cryolipolysis For Noninvasive Fat Cell Destruction: Initial Results From a Pig Model, " Dermatologic Surgery, 35(10):1462-1470, Hagerstown, MD Lippincott, Williams & Wilkins, United States (Oct. 2009).

ZELTIQ System User Manual—Print and Binding Specifications, ZELTIQ Aesthetics, Inc, Mar. 2011, 88 pages.

Zerona R-Z6 by Erchonia, Specifications, Retrieved from the Internet: (www.myzerona.com), 2015, 1 page.

Zerona, Reveal your True Shape, Product Fact Sheet, 3 pages.

Zhang, G., et al., "A Method of Nerve Electrical Stimulation by Magnetic Induction," Annual International Conference of the IEEE Engineering in Medicine and Biology Society 2009:622-625, IEEE, United States (2009).

Zhi-De, D., "Electromagnetic Field Modeling of Transcranial Electric and Magnetic Stimulation: Targeting, Individualization, and Safety of Convulsive and Subconvulsive Applications," Academic Commons (2013) 326 pages.

Zhu, Y., et al., "Magnetic Stimulation of Muscle Evokes Cerebral Potentials by Direct Activation of Nerve Afferents: A Study During Muscle Paralysis," Muscle & Nerve 19(12):1570-1575, John Wiley & Sons, United Sates (Dec. 1996).

Agilent Technologies, Inc., "Agilent 33500 Series 30 MHz Function/ Arbitrary Waveform Generator User's Guide," Publication No. 33520-90001 (Dec. 2010), 278 pages.

Agilent Technologies, Inc., "Agilent Announces 30 MHz Function/ Arbitrary Waveform Generators," Microwave J., URL: <https://www.microwavejournal.com/articles/9851-agilent-announces-30-mhz-function-arbitrary-waveform-generators> (Aug. 3, 2010), 8 pages.

*Allergan, Inc. et al v. BTL Healthcare Technologies A. S.*, PTAB-PGR2021-00015, Paper 16 (Decision Denying Institution of Post-Grant Review), Jun. 17, 2021, 20 pages.

*Allergan, Inc. et al v. BTL Healthcare Technologies A. S.*, PTAB-PGR2021-00016, Paper 16 (Decision Denying Institution of Post-Grant Review), Jun. 17, 2021, 20 pages.

*Allergan, Inc. et al v. BTL Healthcare Technologies A. S.*, PTAB-PGR2021-00017, Paper 16 (Decision Denying Institution of Post-Grant Review), Jun. 16, 2021, 33 pages.

*Allergan, Inc. et al v. BTL Healthcare Technologies A. S.*, PTAB-PGR2021-00018, Paper 16 (Decision Denying Institution of Post-Grant Review), Jun. 16, 2021, 42 pages.

*Allergan, Inc. et al v. BTL Healthcare Technologies A. S.*, PTAB-PGR2021-00020, Paper 16 (Decision Denying Institution of Post-Grant Review), Jun. 16, 2021, 35 pages.

*Allergan, Inc. et al v. BTL Healthcare Technologies A. S.*, PTAB-PGR2021-00021, Paper 17 (Decision Denying Institution of Post-Grant Review), Jun. 16, 2021, 33 pages.

*Allergan, Inc. et al v. BTL Healthcare Technologies A. S.*, PTAB-PGR2021-00022; PTAB-PGR2021-00023; PTAB-PGR2021-00024; PTAB-PGR2021-00025; PTAB-IPR2021-00296; PTAB-IPR2021-00312, Paper 11 (Decision Settlement Prior to Institution of Trial), Jul. 6, 2021, 4 pages.

*BTL Industries, Inc. v. Allergan Ltd. et al.*, DDE-1-20-cv-01046, Order Adminstratively Closing Case, Jul. 26, 2021, 1 page.

*BTL Industries, Inc. v. Allergan USA, Inc. et al.*, DDE-1-19-CV-02356, Order Administratively Closing Case, Jul. 26, 2021, 1 page.

Certain Non-Invasive Aesthetic Body-Contouring Devices, Components Thereof, and Methods of Using the Same, Inv. No. 337-TA-1219, Order No. 30 (Order Concerning the Procedural Schedule), Aug. 4, 2021, 3 pages.

Doucet, B., et al., "Neuromuscular Electrical Stimulation for Skeletal Muscle Function," Yale Journal of Biology & Medicine 85:201-215 (2012).

Gorgey, A., et al., "Effects of Electrical Stimulation Parameters on Fatigue in Skeletal Muscle," J. Orthop. & Sports Phys. Therapy vol. 39(9):684-92 (Sep. 2009).

Hera Estetik Medikal, "Lipostar Manyetik incelme" https://www.heraestetik.com/en/urun-detay/liposter-manyetik-incelme, accessed Dec. 15, 2021.

Hera Estetik Medikal, "Lipostar" dated Jul. 7, 2014. https://www.youtube.com/watch?v=-R7OnFIK9go, accessed Dec. 15, 2021.

Iskra Medical, "TESLA Stym Website," URL: https://web.archive.org/web/20131106123126/http://www.iskramedical.eu:80/magneto-therapy-medicaPtesla-stym (Nov. 6, 2013).

Krueger, N. et al., "Safety and Efficacy of aNew Device Combining Radiofrequency and Low-Frequency Pulsed Electromagnetic Fields for the Treatment of Facial Rhytides," J Drugs Dematol., 11(11):1306-1309 (Nov. 2012).

*Lumenis Be Ltd. v. BTL Healthcare Technologies A. S.*, PTAB-IPR2021-01403, Declaration of Dr. Marom Bikson (EX1002), Sep. 13, 2021, 243 pages.

*Lumenis Be Ltd. v. BTL Healthcare Technologies A. S.*, PTAB-IPR2021-01403, U.S. Pat. No. 10,821,295 Petition for Inter Partes Review, Sep. 13, 2021, 84 pages.

*Lumenis Be Ltd. v. BTL Healthcare Technologies A. S.*, PTAB-IPR2021-01404, Declaration of Dr. MaromBikson(EX1002), Sep. 13, 2021, 245 pages.

*Lumenis Be Ltd. v. BTL Healthcare Technologies A. S.*, PTAB-IPR2021-01404, U.S. Pat. No. 10,124,187 Petition for Inter Partes Review, Sep. 13, 2021, 82 pages.

*Lumenis Be Ltd. v. BTL Healthcare Technologies A. S.*, PTAB-IPR2021-01405. Declaration of Dr. MaromBikson(EX1002), Sep. 13, 2021, 247 pages.

*Lumenis Be Ltd. v. BTL Healthcare Technologies A. S.*, PTAB-IPR2021-01405. U.S. Pat. No. 10,124,187 Petition for Inter Partes Review, Sep. 13, 2021, 86 pages.

*Lumenis Be Ltd. v. BTL Healthcare Technologies A.S.*, PTAB-IPR2021-01402. Declaration of Dr. Marom Bikson (EX1002), Sep. 13, 2021, 244 pages.

*Lumenis Be Ltd. v. BTL Healthcare Technologies A.S.*, PTAB-IPR2021-01402. U.S. Pat. No. 10,821,295 Petition for Inter Partes Review, Sep. 13, 2021, 81 pages.

*Lumenis Ltd. v. BTL Healthcare Technologies A.S.*, PTAB-IPR2021-01273, Declaration of Dr. MaromBikson (EX1002), Aug. 13, 2021, 225 pages.

*Lumenis Ltd. v. BTL Healthcare Technologies A.S.*, PTAB-IPR2021-01273, U.S. Pat. No. 10,478,634, Petition for Inter Partes Review, Aug. 13, 2021, 70 pages.

*Lumenis Ltd. v. BTL Healthcare Technologies A.S.*, PTAB-IPR2021-01275, Declaration of Dr. MaromBikson (EX1002), Aug. 5, 2021, 282 pages.

*Lumenis Ltd. v. BTL Healthcare Technologies A.S.*, PTAB-IPR2021-01275, U.S. Pat. No. 10,632,321, Petition for Inter Partes Review, Aug. 5, 2021, 92 pages.

*Lumenis Ltd. v. BTL Healthcare Technologies A.S.*, PTAB-IPR2021-01276, Declaration of Dr. MaromBikson (EX1002), Aug. 5, 2021, 241 pages.

*Lumenis Ltd. v. BTL Healthcare Technologies A.S.*, PTAB-IPR2021-01276, U.S. Pat. No. 10,965,575, Petition for Inter Partes Review, Aug. 5, 2021, 79 pages.

*Lumenis Ltd. v. BTL Healthcare Technologies A.S.*, PTAB-IPR2021-01278, Declaration of Dr. MaromBikson (EX1002), Aug. 13, 2021, 255 pages.

*Lumenis Ltd. v. BTL Healthcare Technologies A.S.*, PTAB-IPR2021-01278, U.S. Pat. No. 10,709,894, Petition for Inter Partes Review, Aug. 13, 2021, 85 pages.

(56) References Cited

OTHER PUBLICATIONS

*Lumenis Ltd.* v. *BTL Healthcare Technologies A.S.*, PTAB-IPR2021-01279, Declaration of Dr. MaromBikson (EX1002), Aug. 5, 2021, 258 pages.
*Lumenis Ltd.* v. *BTL Healthcare Technologies A.S.*, PTAB-IPR2021-01279, U.S. Pat. No. 10,709,895, Petition for Inter Partes Review, Aug. 5, 2021, 88 pages.
*Lumenis Ltd.* v. *BTL Healthcare Technologies A.S.*, PTAB-IPR2021-01280, Declaration of Dr. MaromBikson (EX1002), Aug. 13, 2021, 235 pages.
*Lumenis Ltd.* v. *BTL Healthcare Technologies A.S.*, PTAB-IPR2021-01280, U.S. Pat. No. 10,478,634, Petition for Inter Partes Review, Aug. 13, 2021, 69 pages.
*Lumenis Ltd.* v. *BTL Healthcare Technologies A.S.*, PTAB-IPR2021-01282, Declaration of Dr. MaromBikson (EX1002), Aug. 5, 2021, 267 pages.
*Lumenis Ltd.* v. *BTL Healthcare Technologies A.S.*, PTAB-IPR2021-01282, U.S. Pat. No. 10,632,321, Petition for Inter Partes Review, Aug. 5, 2021, 89 pages.
*Lumenis Ltd.* v. *BTL Healthcare Technologies A.S.*, PTAB-IPR2021-01283, Declaration of Dr. MaromBikson (EX1002), Aug. 5, 2021, 241 pages.
*Lumenis Ltd.* v. *BTL Healthcare Technologies A.S.*, PTAB-IPR2021-01283, U.S. Pat. No. 10,695,575, Petition for Inter Partes Review, Aug. 5, 2021, 84 pages.
*Lumenis Ltd.* v. *BTL Healthcare Technologies A.S.*, PTAB-IPR2021-01284, Declaration of Dr. MaromBikson (EX1002), Aug. 5, 2021, 279 pages.
*Lumenis Ltd.* v. *BTL Healthcare Technologies A.S.*, PTAB-IPR2021-01284, U.S. Pat. No. 10,709,895, Petition for Inter Partes Review, Aug. 5, 2021, 93 pages.
*Lumenis Ltd.* v. *BTL Healthcare Technologies A.S.*, PTAB-IPR2021-01285, Declaration of Dr. MaromBikson (EX1002), Aug. 13, 2021, 249 pages.
*Lumenis Ltd.* v. *BTL Healthcare Technologies A.S.*, PTAB-IPR2021-01285, U.S. Pat. No. 10,709,894, Petition for Inter Partes Review, Aug. 13, 2021, 79 pages.
Marek Heinfarth, "Lipostar" dated Jan. 10, 2013. https://www.youtube.com/watch?v=hZurkn8iU_U, accessed Dec. 15, 2021.
Notice of Allowance dated Jul. 21, 2021 for U.S. Appl. No. 17/087,850 (pp. 1-8).
Notice of Allowance dated May 6, 2020 for U.S. Appl. No. 16/194,800 (pp. 1-8).
Office Action dated Jul. 10, 2020 for U.S. Appl. No. 15/678,915 (pp. 1-9).
Ruiz-Esparza, J. & J. Barba Gomez, "The Medical Face Lift: A Noninvasive, Nonsurgical Approach to Tissue Tightening in Facial Skin Using Nonablative Radiofrequency," Dermatol Surg, 29(4):325-32 (Apr. 2003).
Stevens, J., et al., "Neuromuscular Electrical Stimulation for Quadriceps Muscle Strengthening After Bilateral Total Knee Arthroplasty: A Case Serie," Journal of Orthopaedic & Sports Physical Therapy, 34(1):21-29 (Jan. 2004).
Turley, J., "Agilent Technologies Announces 30 MHz Function/Arbitrary Waveform Generators with Unparalleled Signal Accuracy," Elec. Eng'g J., URL: <https://www.eejournal.com/article/20100804-03> (Aug. 4, 2010), 8 pages.
U.S. Appl. No. 60/848,720, inventor Burnett, D., filed Sep. 30, 2006 (Not Published).
Woehrle, J., et al., "Dry Needling and its Use in Health Care—A Treatment Modality and Adjunct for Pain Management," J. Pain & Relief, 4(5): 1-3 (Aug. 2015).
Mantis, The non-invasive solution that restores natural beauty, improves health, and offers a renewed psychophysical sense of balance, MR991 theramagnetic, 2020, 8 pages.
Mantis Theramagnetic Compact: the compact that guarantees utmost efficiency and maximum performance, theramagnetic, 2020, 8 pages.
Pollegen, K200545, Legend Pro DMA, Indications for use, dated Oct. 20, 2021, 11 pages.
Jalinous, R., "Technical and Practical Aspects of Magnetic Nerve Stimulation," Journal of Clinical Neurophysiology 8(1):10-25, Lippincott Williams & Wilkins, United States (Jan. 1991).
*Lumenis Be Ltd.* v. *BTL Healthcare Technologies A.S.*, PTAB-IPR2022-00451, Declaration of Dr. Marom Bikson (EX1002), Jan. 24, 2022, 236 pages.
*Lumenis Be Ltd.* v. *BTL Healthcare Technologies A.S.*, PTAB-IPR2022-00451, U.S. Pat. No. 10,806,943 Petition for Inter Partes Review, Jan. 24, 2022, 87 pages.
*Lumenis Be Ltd.* v. *BTL Healthcare Technologies A.S.*, PTAB-IPR2022-00452, Declaration of Dr. Marom Bikson (EX1002), Jan. 24, 2022, 229 pages.
*Lumenis Be Ltd.* v. *BTL Healthcare Technologies A.S..*, PTAB-IPR2022-00452, Pat. No. 10,806,943 Petition for Inter Partes Review, Jan. 24, 2022, 81 pages.
Operating Manual: Magstim ® $200^2$, P/N 3001-23-04, The Magstim Company Limited, Mar. 18, 2005, 34 pages.
Stallknecht, B., et al., "Are Blood Flow and Lipolysis in Subcutaneous Adipose Tissue Influenced by Contractions in Adject Muscles in Humans?," American Journal of Physiology. Endocrinology and Metabolism 292(2):E394-E399, American Physiological Society, United States (Feb. 2007).
Weyh, T., et al., "Marked Differences in the Thermal Characteristics of Figure-of-eight Shaped Coils Used for Repetitive Transcranial Magnetic Stimulation," Clinical Neurophysiology 116(6):1477-1486, Elsevier, Netherlands (Mar. 2005).
Pascual-Leone, Alvaro et al. "Handbook of Transcranial Magnetic Stimulation" 2002 Arnold Publishers, Chapters 1-4, 58 pages.

\* cited by examiner

SYSTEMS AND METHODS FOR TISSUE TREATMENT

CROSS-REFERENCE TO RELATED APPLICATIONS

This application is a continuation of U.S. patent application Ser. No. 15/603,162, filed May 23, 2017, now allowed, which claims priority to and benefit of U.S. Provisional Application No. 62/340,398 filed May 23, 2016, both of which are incorporated herein by reference in their entireties.

TECHNICAL FIELD

The field of the invention is devices and methods for providing aesthetic and therapeutic soft tissue treatment via application of a radio frequency field (RF) and electric currents into the human and/or animal soft tissue.

BACKGROUND

Skin tightening, wrinkle reduction, removal of cellulite, skin lesions, breast and lips enhancement, reduction of fatty tissue, muscle building, strengthening and/or body contouring are aesthetic treatments for which there is a growing demand. Aesthetic therapy commonly includes the application of different treatment energy sources, such as light sources, radio frequency energy sources, ultrasound energy, electric energy or other sources. Every source of energy mentioned above may have some beneficial effect.

Energy is focused to skin and/or to lower layers of body soft tissue. Human skin is composed of three basic layers: the epidermis, the dermis and the hypodermis. The epidermis is composed of the outermost layers of cells in the skin. The epidermis is a stratified squamous epithelium, composed of proliferating basal and differentiated suprabasal keratinocytes which acts as the body's major barrier against an inhospitable environment. The dermis consists of collagen, elastic tissue and reticular fibers. The hypodermis is the lowest layer of the skin and contains hair follicle roots, lymphatic vessels, collagen tissue, nerves and also fat forming a subcutaneous white adipose tissue (SWAT).

Energy may be delivered to soft tissue in order to stimulate skeletal muscle contraction, to treat fat, fibrous tissue, blood vessels and/or other supporting matrix that soft tissue include. Fat is composed mostly of adipocytes. It is possible to distinguish different types of fat tissue but in general, for aesthetic treatment, of primary interest is visceral fat located around internal organs and subcutaneous fat in the hypodermis and/or beneath the skin but above skeletal muscle.

Invasive therapies for body and/or skin enhancement such as skin tightening, wrinkle reduction, cellulite reduction, skin lesions, breast and/or lips enhancement, reduction of fatty tissue and others may be associated with relative long recovery time, discomfort during and/or after treatment (e.g. accompanying liposuction) and increased health risk. Conventional non-invasive treatments for body and/or skin enhancement includes drugs, ointments with active agents, exercise, dieting or combinations of these treatments. These may not be effective or even possible under certain circumstances and therefore the results may disappoint.

Application of RF energy to the tissue may have several benefits on the body and skin function and/or appearance. Nevertheless, methods and devices used for non-invasive ways for improving skin visual appearance and/or body shape and contour by delivering RF energy source of energy may result in irritation of the skin and/or other soft tissues, painful application especially for high intensity stimulus, discomfort during the treatment, lack of deep tissue stimulation, inappropriate localization and/or inhomogeneity of the delivered energy to the treated tissue. Some existing devices and therapies cannot compensate for unexpected circumstance which may occur during the treatment, resulting in treatment which can be insufficient, non-homogenous or risky.

Another problem is that treated cells are accumulated in the soft tissue during and/or after treatment. Accumulation of treated cells may slow healing or cause inflammation and safety concerns.

SUMMARY

It is an object of the present method and/or device to introduce an apparatus and method for improving skin viability, skin and body rejuvenation, skin tightening, scar removing, spider veins removing, restoring and restructuring collagen in the soft tissue body shaping (e.g. butt lifting, breast lifting etc.), body contouring, circumferential reduction, cellulite removing, adipose tissue reduction, adipose tissue removing, muscle relaxation, relaxation of muscle tone, muscle building, muscle strengthening, treating and stimulating pelvic floor tissue and adjacent muscles, remodeling of outer part of genitals treat sexual dysfunctions, treat or reduce incontinence problems, accelerate neocolagenesis, improving blood flow, lymph flow, stimulation of lymph nodes, movement of the vessels, bruise removing, reduce swelling, enhancing vitamin D metabolism, restoring nerve signal transfer, accelerate body metabolism, accelerate cell metabolism, pigmentation disorders, tattoos removal, stress relive, micro-dermal abrasion, hair removal, shortening of recovery time after injury and/or other skin and body affliction using application of RF energy and electrical stimulation to the soft tissue.

Different body parts may be treated, e.g.: saddlebags, abdomen, love handles, bra fat, arm, buttocks and/or others. During one session one or more body parts may be treated.

The device and/or method are based on synergic effect of combined electrotherapy and RF therapy provided by one or more applicators. Therapies may be provided simultaneously, consecutively or with partial overlay.

One or more applicators with a source of energy able to provide electrotherapy and/or RF therapy may be stationary and/or movable. The device may include one or more applicators designed as handheld applicator(s) and/or applicators attached to patients body automatically operating.

The device and method is targeted mostly to people with BMI (body mass index) in range from 18 to 40.

Currently no device and/or method is known having movable applicators with sequential or simultaneous combination for effectively applying electrotherapy (for mainly analgesic effect and/or muscle stimulation) and/or RF therapy for aesthetic treatment.

Combinations of electrotherapy with RF therapy provide a synergic effect as described below. A handheld applicator may be personalized according to an individual patient's needs. The applicator may be able to change targeting and parameters of the treatment during the treatment session without stopping the treatment. The present device and method may provide high treatment effectivity, shortening time of one treatment session, decreasing treatment costs and also provide long lasting results. The device and/or method may have a lower initial cost of the device against equipment covering whole body part treatment techniques that require more or larger treatment energy sources. More complicated and more expensive hardware and software components may be avoided while providing homogenous effective treatment with minimal health risks.

GLOSSARY

Figure 1:
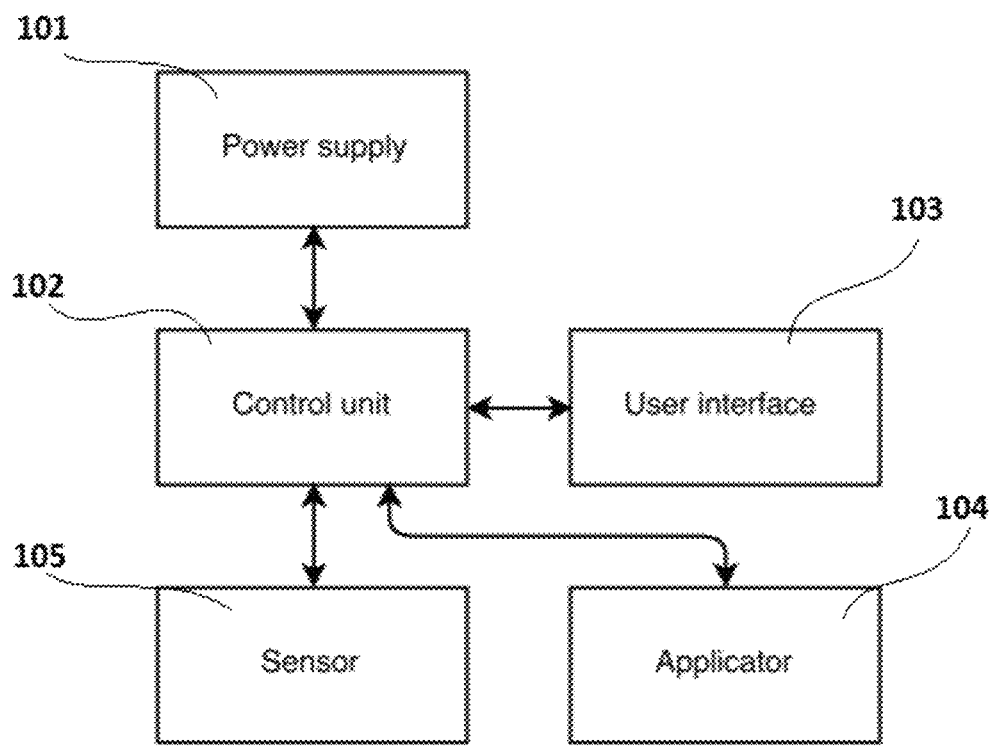
FIG. 1 is a schematic diagram of a treatment system.

Stimulating signal is a signal inducing a physiological effect in the patient's body e.g. a muscle contraction.

Electrotherapy or electrostimulation or electro-stimulation or electrical stimulation is the application of electrical energy (current) into the soft tissue for medical and aesthetic treatment with minimal and/or no thermal effect in soft tissue. Electrotherapy may have different targeted soft tissue and/or stimulating effects (e.g.: analgesic, muscle contraction, muscle relaxation and/or other as described below) depends on electrotherapy parameters. One or more electrotherapy effects or targeting may be combined during one treatment session.

RF therapy provides radio-frequency waves into the soft tissue in order to provide thermal effects in the patient's soft tissue. RF therapy may have different targeted soft tissue and/or stimulating effect (e.g.: skin tightening, cellulite removing, reduction of number and/or volume of adipose cells, collagen recovery and restructuring and/or other effects as described below) depending on RF therapy parameters. One or more RF therapy effects or targeting may be combined during one treatment session.

A treatment session starts with a first treatment therapy and ends with the last treatment therapy described below where delay between two consecutive therapies is no longer than 100 minutes.

RF therapy is application of electromagnetic waves into the soft tissue, with at least some thermal effect in soft tissue.

Soft tissue includes skin, muscle, fat, fibrous tissue, nervous tissue (e.g. neurons, motor neuron, and neuromuscular junction) and/or other supporting matrix.

Parameters of the therapy may be any parameter that can influence treatment therapy (e.g. intensity of the delivered energy, frequency of delivered energy, shape of delivered energy and its modulation, phase shift between several waves, targeting of the energy source, type of the energy source, time interval between application one/or more, the same or different types of the energy source, duration of the treatment therapy, sequence of the treatment therapy, number of the applicators, position of one or more applicators, geometry of the applicator, cooling and/or heating during the treatment, method of the treatment and other parameters that could provide changes in the treatment therapy).

A treatment energy is an energy with a treatment effect (e.g. muscle contraction, heating of the soft tissue etc.). Preferred treatment energy sources are electrodes providing RF therapy and/or electrotherapy. Treatment energy is included in RF waves and/or electric current.

Therapy is at least one of electrotherapy and/or RF therapy.

Aesthetic treatment is one or more of: skin tightening, wrinkle reduction, removal of cellulite, skin lesions, breast and lips enhancement, reduction of fatty tissue, muscle building, strengthening body shaping, body contouring and/or other skin and body affliction.

Viability is better resistance against external influences and removing of some skin affliction as acne treatment, scar removal.

Rejuvenation is younger appearance, removing symptoms of aging.

Skin tightening is change in the helical structure of collagen and results in a micro inflammatory stimulation of fibroblasts, which produces new collagen (neocollagenesis) and new elastin (neoelastogenesis), as well as other substances to enhance dermal structure (breast, lips enhancement, wrinkle reduction and others).

Body shaping is loss of fat but also muscle strengthening, increasing muscle definition and volume of the muscle.

Body contouring is loss of fat (as fat is defined above).

Signal and energy has the same meaning in the manner of delivered energy such as an electromagnetic field, RF field by electrode into the soft tissue and/or electrical energy.

The pelvic floor is formed in a bowl-like structure and contains tissues

DETAILED DESCRIPTION

The device and method may include one or more applicator providing RF therapy and/or electrotherapy. The device may include heating/cooling mechanism. Patient surface may be cooled or heated for the reason of minimizing discomfort, influence of RF therapy tissue penetration and/or decrease health risk.

Cooling/heating may be provided by thermoelectric element with heating/cooling mechanism based on Peltiere's effect and/or heating cooling may be provided by thermal diffusion provided by heated/cooled liquid, air and/or other material with good thermal conductivity. Heating may be also provided by treatment source of energy e.g.: light emitting source of energy, RF source of energy, ultrasound, source of positive and/or negative pressure applied to the patient's surface etc.

Heated or cooled may be directly patient's body and/or any part of the device (e.g. applicators head).

Warming of the tissue is based on dielectric characteristic of the tissue. Heating and/or cooling of the soft tissue may play a significant role because of the soft tissue dielectric characteristic influenced by blood flow in the tissue. Temperature of the soft tissue also influenced metabolism of the cells and organism. While the conductivity of soft tissue increases with the temperature, cooling of the soft tissue may result in less electrical conductivity. These properties may help with targeting of the delivered energy into the soft tissue. Heating and/or cooling during, before and/or after treatment session may be provided via delivering of the energy via therapy, by cooling/heating pads, plates based on thermal diffusion principle, spacing object and/or gels.

Some component of the device may be cooled to prevent overheating.

The present devices may have several possible embodiments based on invasive and/or non-invasive methods. The device sand methods use synergic effects of combination RF therapy with electrotherapy.

According another embodiment RF therapy and electrotherapy may be also combined with any one or more other treatment energy sources: e.g. heating energy source, light energy source, ultrasound energy source, shock wave energy source and/or magnetic field energy source. RF therapy and also RF electrodes may be replaced by any other(s) treatment energy source described above.

RF energy may selectively treat different tissues based on their dielectric properties and localization. Applied RF field affects treated soft tissues mainly by thermal effect. However, RF field may also influence ions and partially charged molecules in the patient's body. This effect may be beneficial in different types of therapies and may provide therapy faster, safer and more effective treatment.

On the other hand the electrotherapy is founded on effects where an electric current (a) passes through the body, and locally changes tissue polarization and ion balance that effect electric potentials in the soft tissue. The effect of electrotherapy may be muscle contraction, local analgesia and/or creating local potentials that influenced cell metabolism, membranes permeability, body metabolism and dielectric characteristic of the soft tissue. Electrotherapy may also heat specific soft tissue structures based on tissue resistivity. According to one embodiment the RF energy source and electrical stimulation may be used simultaneously or in sequence with one or more energy sources.

Electrotherapy maybe used in order to improve: analgesia, tissue regeneration, relaxation, partly tissue ionization, muscle building, muscle strengthening and/or others mentioned in the document. Combinations of above mentioned electrotherapy effects and RF therapy have desirable synergic impact on the soft tissue treatment.

Synergistic use of electro-stimulation of skeletal muscle fibers and/or other soft tissue by using electrotherapy and application of RF field has several benefits. Repeated contraction of muscle fibers improves effect to lymphatic and blood circulation in local and peripheral tissue. Increased blood circulation has positive effect to homogeneity and dissipation of delivered energy into the targeted tissue. Combined therapy (in simultaneous and/or sequential use) minimizes risk of creating of hot spots and consecutive unwanted soft tissue injury during the treatment. Without being bound to the theory it is believed that the increased blood flow in the target soft tissue and/or peripheral soft tissue has substantial influence to removal of cellulite and/or fat tissue.

Another method to reduce adipose cells is skin massaging by electro-stimulation. This method is based on improving of blood circulation and increasing fat metabolism. Improved effect of blood, lymphatic circulation and fat metabolism may be provided by skeletal muscle stimulation.

Electrotherapy may be provided simultaneously, with some overlay or sequentially, before and/or after application of RF therapy. Targeting of electrotherapy may be provided to the same and/or to the different target area as RF therapy is targeted. Electrotherapy and/or RF therapy may be provided by different types of pulses and/or by continual stimulation. Energy of RF therapy and/or electrotherapy may be modulated in different manners (e.g. shape of the signal and his envelop-curve outlining extremes of the signal, polarization of the signal, intensity, frequency, timer between one or more pulses and/or others modulation of delivered energy into the patient soft tissue).

An advantage of electrotherapy is targeting of the energy into concrete muscle fibers or muscle groups. Contracting of muscle fibers may be used for internal massage of target and/or adjacent tissue. This massage phenomenon is beneficial to lymphatic and blood circulation that cause acceleration of metabolism. Faster metabolism provide better treatment result and more effective treatment which means shorting the therapy time and the effect may be long lasting in comparison with prior art methods. Increased lymph flow, blood flow and metabolism activity caused by electrostimulation may help to remove necrotic cells damaged during RF therapy that lower risk of panniculitis.

According to another embodiment a beneficial effect is to treat the cells in order to induce apoptotic death. Due to the combined effect of the RF therapy and electrotherapy and increased blood and lymph circulation, the cells at the targeted area are treated more homogenously and removing of cells is faster.

To improve the treatment effects, the electrotherapy may be used also in several other ways: analgesia, tissue regeneration, relaxation, partly tissue ionization, muscle building, muscle strengthening and/or others mentioned in the document. Combinations of above mentioned electrotherapy effects and RF therapy have desirable impact on the soft tissue treatment.

Analgesic effects of electrotherapy may be used to minimize discomfort during the treatment. Some oversensitive individuals frequently have uncomfortable and/or painful feelings during the treatment if the treatment therapy is running in the range of safe threshold limits. If the delivered energy would be in comfortable limits for oversensitive individuals, treatment therapy would be inefficient, that is the reason why analgesic effect of electrostimulation is desirable during the RF therapy.

Without being bound to the theory, it is believed that the electrotherapy may also improve localization of RF therapy, because through electrotherapy it is possible to change impedance in soft tissue. Partial ionization of some tissue could also improve localization of delivered RF energy and make therapy faster and more effective.

It is possible to combine different effect of electrotherapy (e.g. analgesic and/or muscle stimulation) and/or RF therapy at the same and/or different time and/or at the same or different areas. This may be used to influence treatment results (e.g. tissue repair, improve cutaneous perfusion during and/or after treatment, comfort during the treatment, effectiveness of the treatment and/or other treatment process parameters and results).

Another synergic use of warming up tissue by an RF field and electrotherapy is improvement of muscle relaxation after muscle stimulus reverberation. Tissue warm up accelerates tissue regeneration and prevents or minimizes risk of muscle injury.

The applicator may use three types of the electrodes used as a treatment energy source. A first type of the electrode may be used as a source of energy for electrotherapy and also RF therapy. A second type of the electrode may provide just electrotherapy and the third type of the electrode may provide just RF therapy. One applicator may combine each type of the electrodes or just some of them.

In one embodiment the applicator may be stationary adjacent to the patient surface. In another embodiment moving the applicator or multiple applicators may be advantageous.

The one or more applicators may be placed or moved in a chosen geometry pattern comprising of e.g. linear, wavy circular, elliptical, zigzag, polygonal, oval, irregular, curvilinear or their combination. This moving may be replicated by placing one or more stationary applicators in position and switching over relevant electrodes, without moving the applicators.

The same possible movements of one or more applicators may be considered for moving the electrodes.

The applicator may have a head with removable extensions. Head extensions may be specialized for different kinds of therapies. Extension heads may have different sizes, shapes, geometry (e.g. different distance between RF electrodes that influenced treatment depth), numbers and type of the treatment energy sources (e.g. type of the electrodes) and may be made of different materials (e.g. ceramic, silicone, metal and/or polymeric materials). The applicator's extension heads may be changed during the treatment session based on treated body part or individual patient's needs. The type of the extension head may be recognized automatically by the device and/or the operator may distinguish type of the extension head in user interface 103 of FIG. 1.

The applicator may include at least one RF electrode operating in monopolar, bipolar or multipolar mode and at least one electrode providing electrotherapy operating in monopolar or bipolar mode.

A handheld applicator may include one or more RF electrodes and one or more electrodes providing electrotherapy may be attached to patient body separately from the handheld applicator and/or RF therapy may be located in the patient's body (e.g. in the vagina) in order to provide optimal targeting of treatment energy.

Electrodes as the treatment energy sources may communicate each other no matter on type of the electrodes and/or between the same type of the electrodes.

One or more electrodes may be modularly connected to the applicator to vary the treatment surface, distance between electrodes and provide treatment easier, more effective, faster and/or safer. Electrodes may be controlled individually and/or in group consists of at least two electrodes.

Controlling the electrode by control unit 102 (FIG. 1) includes changing parameters of produced energy: intensity, flux density, time between pulses, shape of signal, phase of individual pulses, type of produced therapy and/or switching on/off individual electrode or electrodes. Controlling of the electrode may be automatic by the device, according treatment protocol and/or may be changed by the operator.

Control unit 102 may be part of one or more applicators 104, individual electrodes and/or may be located out of the applicator.

The applicator and/or electrodes may be created from rigid or at least partly flexible material adaptable to curved patient's body surface.

Transfer of electrical and/or RF energy into the soft tissue and may be based on capacitive, inductive and/or resistive energy transfer.

RF therapy provides electromagnetic field which heats soft tissue. Heat is produced as a resistive loses of electromagnetic energy. RF therapy may be also used for the reason of pre-heating of the soft tissue that may influence soft tissue dielectric parameters as was mentioned above. Pre-heating before during and/or after electrotherapy or other RF therapy treatment may be provided by the same applicator's electrode(s) providing other RF therapy treatment (e.g. removing adipose tissue, heating of collagen fibers etc.) and/or by specific RF electrodes designed for pre-heating purpose.

RF thermal stimulation results in micro inflammatory stimulation of fibroblasts, which produce new collagen (neocollagenesis) and/or new elastin (neoelastogenesis), as well as other cells to enhance dermal structure.

Treatment by electromagnetic field and a spacing object enables create gradients across the soft tissue of the patient. Targeting of a thermal gradient by applied electromagnetic field and continuous but more preferably sequential heating and/or cooling of the patient surface by the spacing object and/or by other above mentioned method may improve the effect of the treatment and minimize health risk.

RF thermal stimulation of adipose tissue is also believed to result in a thermal-mediated stimulation of adipocyte metabolism and augmented activity of lipase-mediated enzymatic degradation of triglycerides into free fatty acids and glycerol. Induction of apoptosis and/or necrosis of fat cells are another proposed mechanism for removing of fat.

RF therapy can be applied to the soft tissue in various manners. The treatment system may use bipolar electrodes, where electrodes alternate between active and return function and where the thermal gradient beneath electrodes is during treatment almost the same. The system may alternatively use monopolar electrodes, where the so called return electrode has larger area than so called active electrode. The thermal gradient beneath the active electrode is therefore higher than beneath the return electrode A unipolar electrode may also optionally be used. During unipolar energy delivery there is one electrode, no grounding pad, and a large field of RF emitted in an omnidirectional field around a single electrode.

The electromagnetic field used for heating the soft tissue may be a radiofrequency field or microwave field, typically in a range of 0.1 MHz to 25 GHz. Waves of the RF therapy may be delivered preferably in range from 100 kHz to 3 500 kHz or 6 765 to 6 795 kHz or 13 553 to 13 567 kHz or 26 957 kHz to 27 283 kHz or 40.66 to 40.7 MHz or 433.05 to 434.79 MHz or 902 to 928 MHz or 2 400 to 2 500 MHz or 5 725 to 5 875 MHz or 24 to 24.25 GHz or 61 to 61.5 GHz or 122 to 123 GHz or 244 GHz to 246 GHz or optionally at other frequencies as well.

RF electrodes may be in contact with the patient's body and/or may be spaced from the patient's body contact with air gap and/or by spacing object or other material.

Energy flux density of RF therapy is preferably in the range of 0.01 mW·mm$^{-2}$ to 10 000 mW·mm$^{-2}$, 0.1 mW·mm$^{-2}$ to 5 000 mW·mm$^{-2}$, or 0.5 mW·mm$^{-2}$ to 1 000 mW·mm$^{-2}$.

Energy flux density (energy flux density on the electrode surface) of the electromagnetic field in noncontact mode, where electrodes providing RF signal are spaced from the patient body by an air gap may be preferably in range between 0.01 mW·mm-2 and 10 W·mm-2, more preferably in range between 0.01 mW·mm-2 and 1 W·mm-2, most preferably in range between 0.01 mW·mm-2 and 400 mW·mm-2.

Energy flux density of the electromagnetic field in contact mode (including the direct contact of electrodes coated by thin layer of insulator) may be preferably in range between 0.01 mW·mm-2 and 2 000 mW·mm-2, more preferably in range between 0.01 mW·mm-2 and 500 mW·mm-2, most preferably in range between 0.05 mW·mm-2 and 280 mW·mm-2.

Energy flux density of the electromagnetic field in non-contact mode where electrode is spaced from the patient body by spacing object or other material with beneficial dielectric parameters e.g.: bolus filled with water, silicon and/or other materials) may be preferably in range between 0.01 mW·mm-2 and 500 mW·mm-2, more preferably in range between 0.01 mW·mm-2 and 240 mW·mm-2 or even more preferably in the range between 0.01 mW·mm-2 and 60 mW·mm-2 or the most preferably in range between 0.05 mW·mm-2 and 12 mW·mm-2.

The source of RF waves and/or electrotherapy may be at least one electrode. When the only one electrode is applied, the electrode may serve as both the RF and the electrotherapeutic source. The therapies may be applied together, successively or in overlap. The electrode may consist of electrode itself and coating, wherein the coating may not cover the whole surface of electrode.

The soft tissue is heated to 10-70° C. more preferably to 20-60° C., most preferably to 30-50° C.

The main effects of electrotherapy are: analgesic, myorelaxation, iontophoresis, and at least partial muscle stimulation causing at least partial muscle fiber contraction and anti-edematous effect.

Each of these effects may be achieved by one or more types of electrotherapy: galvanic current, pulse direct current and alternating current.

Galvanic current (or "continuous") is a current that may have constant electric current and/or absolute value of the electric current is in every moment higher than 0. It may be used mostly for iontophoresis, or its trophic stimulation (hyperemic) effect is utilized. At the present invention this current may be often substituted by galvanic intermittent current. In some preferred embodiment galvanic component may be about 95% but due to interruption of the originally continuous intensity the frequency may reach 5-12 kHz, in more preferred embodiment 5-9 kHz, in the most preferred embodiments 5-8 kHz.

The pulse direct current (DC) is of variable intensity but only one polarity. The basic pulse shape may vary. It includes e.g. diadynamics, rectangular, triangular and exponential pulse of one polarity. Depending on the used frequency and intensity it may have stimulatory, tropic, analgesic, myorelaxation, iontophoresis, at least partial muscle contraction and anti-edematous effect and/or other.

Alternating Current (AC) where the basic pulse shape may vary—rectangular, triangular, harmonic sinusoidal, exponential and/or other shapes and/or combination of mentioned above. It can be alternating, symmetric and/or asymmetric. Use of alternating currents in contact electrotherapy implies much lower stress on the tissue under the electrode. For these types of currents the capacitive component of skin resistance is involved, and due to that these currents are very well tolerated by the patients.

AC therapies may be differentiate to five subtypes: TENS, Classic (four-pole) Interference, Two-pole Interference, Isoplanar Interference and Dipole Vector Field. It also exist some specific electrotherapy energy variants and modularity of period, shape of the energy etc.

Due to interferential electrotherapy, different nerves and soft tissue structures by medium frequency may be stimulated preferably in a range of 500 Hz to 12 kHz or in amore preferred embodiment in a range of 500 to 8 kHz, or 500 to 6 kHz, creating pulse envelopes with frequencies for stimulation of the nerves and tissues e.g. sympathetic nerves (0,1-5 Hz), parasympathetic nerves (10-150 Hz), motor nerves (10-50 Hz), smooth muscle (0-10 Hz), sensor nerves (90-100 Hz) nociceptive fibres (90-150 Hz).

Electrotherapy may provide stimulus with currents of frequency in preferred embodiment in the range from 0 Hz to 12 kHz or in more preferred embodiment from 0 Hz to 8 kHz or in the most preferred embodiment in range from 0 Hz to 6 kHz.

Time between two pulses and/or time between two band of pulses (burst) may be variable depend on some function and adjustable to type of therapy and type of the patient.

According to one embodiment an analgesic effects may be achieved. The analgesia is beneficial during the treatment of high dose RF therapy and in order to make therapy more comfortable. Some oversensitive individuals may have uncomfortable and/or painful feelings during the treatment therapy event if the treatment runs within the range of safe threshold limits. If the delivered energy would be in comfortable limits for such oversensitive individuals, treatment therapy would be inefficient. Therefore, the analgesic effect of electrostimulation may be desirable. Another beneficial effect is that if patient feels pain, the patient usually increases muscle tone in this area. Long lasting muscle contraction may cause pain in the muscle part for several days and/or damage of muscle fibers. Long lasting muscle contraction is therefore not only uncomfortable but it also may affect the blood and lymph circulation. Whereas the treatment may be improved by sufficient fluid circulation during and/or after the treatment.

Pain is a multi-factor phenomenon and there are several mechanisms through which the analgesic effect of electrotherapy is achieved.

It is possible to distinguish several pain management approaches. One of them is called gate-control theory based on a premise that the pain is transmitted through a "gate" in substantia gelatinosa in spinal dorsal horn. Stimulation of large-diameter fibers Aβ activates inhibitory spinal interneurons which prevent the passage of information by activated thin Aδ and C nerve fibres to the brain. If signal from activated Aδ and C nerve fibers is not inhibited such signal results in pain in the brain. Another pain theory is pattern theory premises that the pain excitement is transmitted from the peripheral receptor to the CNS in a pattern coded energy and the pain is interpreted by decoding the energy in CNS.

The last pain management theory is called release of endogenous opioids based on the effect of endorphins, enkephalins and dynorphins. The secretion of these three endogenous opioids may be caused of nerve fiber stimulation by low repetition rate in range 5 Hz to 20 Hz or by high repetition rate in range 110 Hz to 150 Hz time-varying magnetic and/or electric field or by the low repetition rate envelope.

Pain is usually simply defined as an unpleasant sense and emotional experience, connected with actual or potential damage of the tissue. We usually distinguish between acute and chronic pain. Acute pain is short-lasting (maximum several days or weeks). It is caused by mechanical damage of the tissue or by a disease, comes immediately after the painful stimulus and subsides after its ending. The intensity of acute pain depends on the intensity of stimulation. On the other hand, chronic pain is long-lasting (more than 3 months) or recurrent. Its intensity does not depend on the intensity of stimulation; emotions particularly play a leading role.

Effects of electrotherapy it is important to understand especially the modulating factors influencing the perception and transfer of the painful stimulus. An analgesic effect may occur by stimulation of type Aβ nerve fibres by frequency 50-150 Hz and/or type C-thin fibers by frequency 2-8 Hz.

For most of analgesic effect it is possible to choose several types of currents e.g. diadynamic current, currents changing in long lasting period, bipolar amplitude modulated medium frequency currents, TENS and/or, other of interferential currents (in range of 0,1-1 kHz). Frequencies of the currents are described above.

A myorelaxation effect may be achieved. Myorelaxation effect causes at least partially decrease the muscle fiber tone. Myorelaxative effect may be beneficial for improving homogeneity of delivered RF therapy and/or faster regeneration of the soft tissue and/or more comfortable therapy also. Long lasting permanent muscle contraction may slower body fluid circulation e.g. lymph and blood circulation, that has crucial therapy effect. Long lasting muscle contraction is also very exhausting. For better results the therapy should be comfortable because the psychological state of the patient influences human metabolism.

In order to provide myorelaxation, the amplitude modulated medium frequency currents with frequency of the pulse envelope in a range of 5-300 Hz or 10-200 Hz or 10-150 Hz may be used. It is also possible to use TENS and/or other.

Muscle fibers stimulation may be achieved, increasing muscle tone, muscle strengthening, restoration of feeling the muscle, relaxation of the musculature and/or stretching musculature.

Muscle fiber stimulation by electrotherapy may be important during and/or as a part of treatment provided RF therapy. Muscle stimulation increases blood flow and lymph circulation. It may improve removing of treated cells and/or prevent of hot spots creation. Moreover internal massage stimulation of adjoining tissues improves homogeneity of tissue and dispersing of the delivered energy. Another beneficial effect is for example during fat removing with the RF therapy. RF therapy may change structure of the fat tissue. The muscle fiber stimulation may provide internal massage, which may be for obese patient more effective than classical massage.

Muscle stimulation may be provided by e.g. intermittent direct currents, alternating currents (medium-frequency and TENS currents), faradic current as a method for multiple stimulation and/or others. Frequency of the currents and/or its envelope is typically in the range from 0.1 Hz to 200 Hz in preferred embodiment or from 0.1 Hz to 150 Hz in more preferred embodiment or from 0.1 to 140 Hz in the most preferred.

Muscle stimulation may be at least partial muscle contraction, e.g.: gluteus maximus, gluteus medius, gluteus minimus, sartorius muscle, rectus femoris muscle, vastus lateralis muscle, vastus intermedius muscle, vastus medialis muscle, biceps femoris muscle, semitendinosus muscle and semimembranosus muscle, pectineus muscle, external obturator muscle, gracilis muscle, adductor longus muscle, adductor brevis muscle and adductor magnus muscle, tensor fasciae latae muscle, latissimus dorsi muscle, abdominal internal oblique muscle, abdominal external oblique muscle, transverse abdominal muscle, pyramidalis muscle, biceps brachii muscle, brachialis muscle, coracobrachialis muscle, triceps brachii muscle, pectoralis muscle, spinal muscles, thoracic muscles. Muscles in pelvic and/or adjacent to pelvic floor may also be stimulated, helping to resolve problems with incontinence, improve sex life and/or restore relaxed muscles after birth.

A trophic effect may be achieved. A trophic effect created by electrotherapy may have beneficial influence on homogeneity, energy dissipation, creating of hot spots and/or other. Trophic effect may eliminate the risk of hyperthermia injury and/or panniculitis, which are possible to occur during RF treatments. It is also believed that a trophic effect also improves the cell metabolism (e.g. fat cell) that may have with delivered RF therapy synergic effect and better result namely for treating of fat tissue, removing of the cellulite.

Since the mechanism of hyperemia in various types of therapies is different, it is necessary to take these mechanisms into account to be able to select a suitable therapy. Generally, galvanization can be recommended. Other recommended frequency may be especially longitudinal (capillary hyperemia, vessel eutonization), low-frequency currents of the frequency 30-60 Hz or 10-100 Hz. The trophic effect may be partly caused by bringing energy into the organism and energy is used by cells (or other structures) for their activity. The trophic hyperemic effect is also usually connected with the analgesic effect.

An anti-edematous effect may be achieved. Anti-edematous effect may be practically connected with hyperemia, vessel eutonisation and higher capillary permeability. Therefore the therapies referred to as trophic are also anti-edematous. This could be beneficial for stimulation of lymph and blood circulation and removing of treated cells during, before and/or after treatment therapy include RF therapy (e.g. fat removing).

Described frequencies are just examples of the most frequently used frequencies in some embodiments. Described ranges of frequencies are not limited. The individual embodiments may be applied to the tissue simultaneously, successively and/or in overlay.

The electrostimulation may be provided in a combined manner where various treatments with various effects may be achieved. As an illustrative example, the electromagnetic stimulation may be dosed in trains where the first train of stimulation may achieve different effect than second or other successive train of stimulation. Therefore, the treatment may provide muscle fibers stimulation followed by relaxation, during continual or pulsed radiofrequency thermal heating.

Absolute value of voltage between the electrotherapy electrodes operated in bipolar, unipolar mode (electric current flow between more than two electrodes) and/or provided to at least one electrotherapy electrode may be in range between 0.8 V and 10 kV; or in range between 1 V and 1 kV; or in range between 1 V and 300 V or in range between 1 V and 100 V.

Current density of electrotherapy for non-galvanic current may be in range between 0.1 mA·cm$^{-2}$ and 30 mA·cm$^{-2}$, or in range between 0.1 mA·cm$^{-2}$ and 10 mA·cm$^{-2}$, or in range between 0.1 mA·cm$^{-2}$ and 4 mA·cm$^{-2}$, or in range between 0.1 mA·cm$^{-2}$ and 2 mA·cm$^{-2}$; for galvanic current may be preferably in range between 0.05 mA·cm$^{-2}$ and 3 mA·cm$^{-2}$, or in range between 0.1 mA·cm$^{-2}$ and 1 mA·cm$^{-2}$, or in range between 0.01 mA·cm$^{-2}$ and 0.5 mA·cm$^{-2}$.

Electrostimulation may be provided by monopolar or bipolar mode.

During bipolar electrotherapy mode two or more electrodes may be used. If polarity of at least one electrode has a non-zero value in a group of the electrodes during bipolar mode, the group of the electrodes has to include at least one electrode with opposite polarity value. Absolute values of both electrode polarities may or may not be equal. In bipolar electrostimulation mode stimulating signal passes through the soft tissue between electrodes with opposite polarities.

Distance between two electrodes operating in bipolar mode may be in range between 0.1 cm and 40 cm or in range between 1 cm and 30 cm, or in range between 1 cm and 20 cm.

During monopolar electrotherapy mode stimulating signal may be induced by excitement of action potential by changing polarity of one electrode that change polarization in the nerve fiber and/or neuromuscular plague.

During electrotherapy may be combined bipolar and monopolar electrotherapy mode or may be used just one of them.

A handheld applicator may include one or more electrodes providing electrotherapy. Providing effective electrotherapy e.g. muscle stimulation and/or analgesic with movable one or more electrodes during the treatment may be complicated. In order to provide effective analgesic and/or muscle stimulation treatment after placing applicator's head into contact with the patient's body, applicator may create one or more electric testing pulses provided to the patient's soft tissue.

Testing pulses may have increasing repetition rate, increasing intensity or may be predefined according other criteria in the treatment protocol. Testing pulses may be monitored. Feedback information from testing pulses, measurable values on the electrodes or soft tissue under or between the electrodes e.g. changed impedance of at least part of the soft tissue or changed potential in the soft tissue, may be evaluated and optimal treatment parameters in order to cause physiological effect by electrotherapy (e.g. creating nerve action potential excitation and muscle contraction) may be sets up and electrotherapy may starts.

Testing pulses may be one or more pulses. Testing pulses for actual applicator and/or electrode(s) position may last between several picoseconds to several seconds. Testing pulses may be applied every time applicator change location on the patient's body, target area or soft tissue parameters changed more than is sets up in the treatment protocol. Testing pulses may be also applied with defined time delay which is defined in the treatment protocol.

Testing pulses may be used to automatically choose an area on the patient's body where electrotherapy may be provided and/or may be used for setting optimal parameters for chosen type of applied electrotherapy (e.g. intensity, repetition rate, type of pulse sequence, shape of provided pulses and/or other parameters).

An optimal area on the patient body for electrotherapy may be saved into the device memory and testing pulses may not be provided every time when treated area is the same.

Recognition of the same treated area on the patient's body may recognize by tracing applicator moves and/or by other mechanism.

At least one electrode for electrotherapy may be included in the handheld applicator and at least other one electrode for electrotherapy may be located attached to the patient's body. Electrostimulation according such device embodiment may be based on moving with the applicator according treatment pattern across the patient surface.

Treatment patterns may be based on circular moves, curvilinear moves and/or linear moves creating treatment pattern.

All electrodes providing electrotherapy may be located outside of the handheld applicator in contact with the patient's body. Such electrode may communicate with the applicator and may adjust electrotherapy according to moving with the applicator.

Electrodes providing electrotherapy may be connect to the rest of the device by wire and/or may have its own power supply 101 (e.g. at least one batteries) and also may communicate with the device (control unit 102) wirelessly.

A wireless electrode may include its own power supply (e.g. battery) and may include hardware and/or software equipment in order to be able to communicate with control unit 102 of the device, other electrode(s) and be able to provide treatment. Wireless electrode may be attached to patient's body and provide any type of treatment therapy (e.g. RF therapy and/or electrotherapy) without wire connection with the rest of the device.

Communication, attaching applicator(s) to patient's body, provided treatment patterns and/or other features may be used as described in U.S. Provisional Application No. 62/375,796 incorporated herein by reference.

Placing the stationary electrodes providing electrotherapy may be based on operator experience, by observing physiological effect (e.g. muscle contraction) and/or may be based on impedance changes and/or specific electric potential changes as was described above.

In FIG. 1 is captured one exemplary schematic diagram of a proposed system. The system may comprise power supply 101, control unit 102, user interference 103, one or more sensors 105 and applicator 104 providing RF therapy and/or electrotherapy.

Electrodes that may provide RF therapy and also electrotherapy may be switching between these two types of therapies during one treatment session. If the treatment protocol defines switching between RF therapy and any electrotherapy on one electrode at least once during 20 second provided RF therapy last at least 40%, or 50%, or 70% or 90% of time when the electrode provides any kind of therapy.

Power supply 101 may be managed by control unit 102. Regulation of delivered energy may be controlled by control unit 102. The control unit 102 may also evaluate feedback information from one or more sensors 105, and/or treatment parameters from user interface 103. Control unit 102 may contain one or more cooperating units. Control and cooperation units are elements of the device that has influence on treatment parameters of the therapy (e.g. therapy time, amount of delivered energy, burst timing, frequency of provided energy, intensity of energy, controlling switching on/off different group of electrode/s, shape of the pulses and others).

The user interface may allow the operator to change and/or set up the treatment parameters. Treatment parameters may be set up in the range of safe thresholds (e.g. individually for each therapy). Threshold treatment parameters may be operatively changed depending on therapy and/or detected parameters from the feedback sensors. Safe dosage of the delivered energy and/or dependence of each parameter may be pre-set. Course of treatment may be provided by computer and/or operator. Treatment may be guided manually, automatically and/or semi-automatically where some of the treatment parameters were set up manually. A computer may change inappropriately set up parameters and/or alert the operator.

If treatment parameters are evaluated as safe, therapy may start. It may be possible to adjust parameters of the therapy or add therapy types e.g. galvanic current, pulse direct current and alternating current. Treatment may be time limited and stopped by if values of one or more detected parameters reached their limits e.g. time, time and temperature. Safe thresholds may be dependent on treated body part or target area. The constitution of the treated soft tissue is important. This may be classified by e.g. ultrasound, from the information of backscattered radiofrequency wave.

Treatment therapy may be guided with partially or fully predetermined treatment protocol or without predetermined protocol where the operator may adjust some or all parameters of the treatment. The system may provide information to the control unit about electrode(s) connected and ready to participate in the treatment.

Treatment may be guided automatically without need of an operator. Treatment is guided according a defined treatment protocol. During such treatment feedback information from one or more sensors may be evaluated in control unit 102 and according feedback information treatment parameters may be regulated in order to provide safe treatment.

The device may have one or more sensors 105 providing feedback information in order to improve efficiency of the treatment and minimized health risk. Based on feedback treatment information therapy parameters could be manually or automatically or semi-automatically optimized or therapy could be interrupted (as was mentioned above). The device may contain different types of sensors 105 for monitoring device parameters and/or monitoring of body biological, physical, chemical and/or other parameters (e.g. a reactive sensor; an electrochemical sensor; a biosensor; a biochemical sensor; a temperature sensor; sensor for measuring distance of applicator from the patient surface, from some area of the patient soft tissue and/or from other applicator; a sorption sensor; a pH sensor; a voltage sensor; a detector of moving velocity, gyroscope detecting moves and/or change of position; photo sensor; sensor measuring viscosity; a camera; a sensor measuring fluorescence of the patient surface; a sound detector; a current sensor; sensor for measuring of specific heat capacity of human/animal tissue; sensor for measuring impedance; permittivity; conductivity; susceptibility, value of electric field, magnetic field and/or any suitable sensor or sensors measuring biological parameters and/or combination thereof e.g.: sensor for measuring dermal tensile forces; sensor for measuring the activity of the muscle; a muscle contraction forces; skin elasticity). The device may also include at least one contact sensor for monitoring of applicator and/or electrode or more electrodes contact with body surface.

Each sensor 105 may provide feedback information to control energy delivery and/or other treatment parameters to improve efficiency of a treatment and/or minimized health risk and/or discomfort during the treatment. The treatment therapy parameters may be manually or automatically or semi-automatically optimized based on feedback information. If the treatment parameters are evaluated as not-safe, the treatment maybe stopped or the values treatment parameters may be changed.

Treatment therapy may be guided with partially or fully predetermined treatment protocol or without predetermined treatment protocol. Result of this is that the treatment may be carried automatically (allowing treatment without operator), semi-automatically and/or by operator. Operator may set up and/or adjust any parameter of treatment therapy before and/or during the treatment.

The applicator may contain a suction unit to create negative pressure and may be attached to patient's body. The applicator may contain plug-in connector for connecting one or more electrodes.

Figure 3:
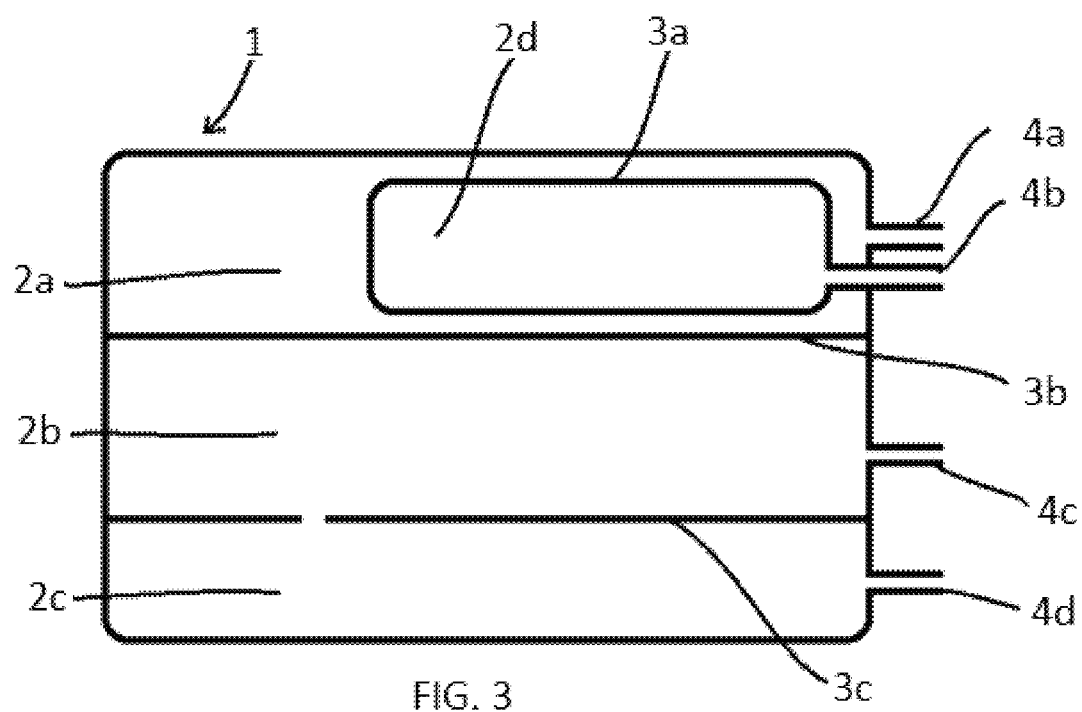
FIG. 3 is a schematic representation of a spacing object.

At least one spacing object may be provided between the applicator and patient's skin surface. A spacing object is shown in FIG. 3. Spacing object 1 may improve transfer of electromagnetic field into the soft tissue. This could be provided by the spacing object itself and/or filler inside of the spacing object and/or thanks to design of the object. Various materials having suitable dielectric constant, density and/or other parameters may be used in order to prevent backscattering of the electromagnetic wave and improve transfer of electromagnetic wave to the soft tissue and improve effectiveness of the treatment. Backscattering may occur at the interface of the materials with different physical parameters, analogous to optical phenomenon at the interface of different refractive indexes.

Inner space of the spacing object 1 may be separated or partly separated into one or more chambers 4a-4d by walls 5a-5c. Each chamber may include one or more cells which may be provide optimal ducting for the flowing substance and/or which may strengthen the walls of chamber in order to preserve the shape of the chamber and object. Each part of the spacing object inner space may have different filler and therefore function. Filling of the inner space of the spacing object 1 may be done during the manufacturing process. According to another embodiment the inner space may be filled and/or circulated during the therapy through one or more inlet/outlet valves 6a-6d. Changing and/or removing of the inner substance of the object may be provided through the inlet/outlet valve 6a-6d also.

The spacing object 1 and/or filler inside may have advantageous dielectric constants (permittivity, permeability, conductivity) and/or other parameters and constants (thermal conductivity, specific heat capacity . . . etc.). and may be used as focusing element, absorbing element, polarizing element, dispersing element, transmitting element, massaging element, reflecting element of backscattered waves, for transfer electromagnetic wave, cooler, heater and/or creator of thermal gradient in the soft tissue of the patient Filler of the spacing object may be gaseous, liquid and/or from solid material. Spacing object may be composed of any kind of ceramics, plastic material, rubber, textile material, metal, polymeric materials and/or other material that improve any therapy parameter/s. In some embodiment may be important to choose material and/or construction of the object to provide stable form and/or shape of the spacing object. Spacing object may be flexible and/or rigid and may imitate curves of the body contour.

Filler of the spacing object may provide polarization and/or reflection and/or may focus delivered electromagnetic energy and/or may be used as a filter of electromagnetic wave and/or may adjust orientation of the wave vector of the electromagnetic wave as was mentioned below. Polarization of the electromagnetic wave has different impact on different molecules and environments, so polarization may influence absorption, dispersion, penetration, targeting and/or reflection of electromagnetic wave. Polarization of the electromagnetic wave may be created by anisotropic arrangement of dielectric films (e.g. by poly(vinyl alcohol) doped by iodine or other substances based on dichroic polarizers principle) and/or by principle of the phase retardation plate and/or by material and/or geometry of the antenna. Some polarization and reflection element may have crucial influence to prevent creating hot spots due to changing of the orientation of the wave vector end selective modification of the component of the electromagnetic wave.

Treatment by electromagnetic field and spacing object enabling changing of temperature and/or other parameters (permittivity, permeability, conductivity and/or their parameters) and/or its one or more component may create temperature gradients across the soft tissue of the patient. This is important because tissue dielectric parameters (e.g. impedance, conductivity and/or other related dielectric parameters) change with different temperature and frequency of applied electromagnetic waves. Targeting of thermal gradient by applied electromagnetic field and continuous but more preferably sequential heating and/or cooling of the patient surface by the spacing object may improve the effect of the treatment and minimize health risk.

Spacing object 1 may prevent harmful influence of edge effects in connection with delivering energy by electrodes. Preventing the edge effect is achieved via dispersion of the electromagnetic energy, cooling and/or changing orientation of the Poyting's vector of the electromagnetic field in the object. Object 1 may also cause the higher homogeneity of the electromagnetic field.

Cooling or heating of tissue may be provided by a spacing object filled with a suitable substance (mostly liquid or gaseous substance e.g. water, water doped NaCl, ethanol, air, $N_2$, $CO_2$, air and others). The parameters of the substance such as temperature, viscosity, flow etc. may be monitored by one or more sensors (e.g. temperature and/or viscosity sensors and/or sensor measure inducted currents or chemical changes of the substance). Monitored parameters may provide feedback information to control unit for regulate flow of the substance through the spacing object. Object 1 may be extended by complementary connection of other one or more chambers. Extension of spacing object may share filler or may have different function e.g. protection of different area from overheating, over-radiation and/or other influences, different cooling program, modulation of the delivered energy to the patient (polarizing, filtering etc.) and/or other functions (focusing etc.).

Figure 2:
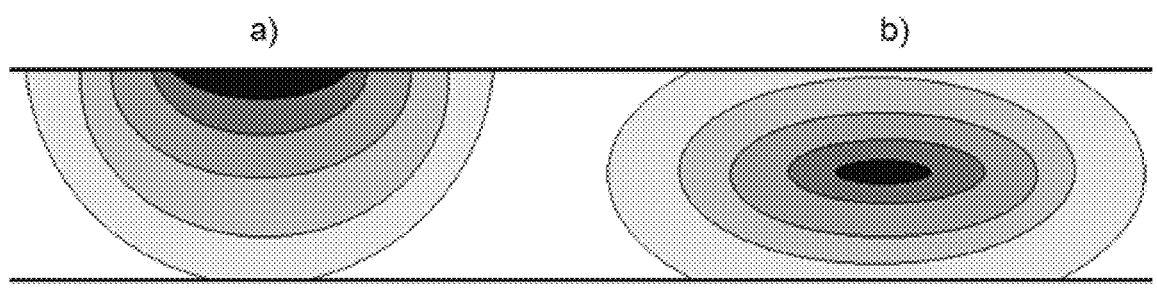
FIG. 2 illustrates example of thermal gradients.

Thermal gradients are represented in FIG. 2. In some embodiment it is possible to create a thermal gradient by heating and/or cooling surface of the patient skin with highest or lowest temperature on the skin surface FIG. 2 a) and/or it is possible to create temperature gradient with highest or lowest temperature beneath the surface of the soft tissue FIG. 2 b). The effect described at FIG. 2 b) may be provided by sequential heating/cooling of the patient surface and/or by focusing of delivered electromagnetic and/or thermal energy.

In one method, the patient's surface (epidermis) temperature may be maintained in a range between 20° C. to 44° C., or in range between 30° C. to 44° C., or in range between 30° C. to 40° C. Such treatment method may maintain lower temperature of the patient's epidermis than is temperature in the treated patient's adipose tissue.

The increase of the temperature in the dermal and the sub dermal tissues also affects the triple-helix structure of collagen fibers contained in such tissues. This may result in remodeling and rejuvenation of collagen, increase of skin density and dermal thickening Spacing 1 located between the patient's soft tissue surface and the treatment energy source may have specific properties and influence parameters of treatment energy as described in U.S. Provisional Application No. 62/331,072, incorporated herein by reference.

In one aspect the device is designed as a belt that may be modularly modified by adding and/or removing one or more part of the device (e.g.: applicators, treatment units and/or others) before and/or during the treatment. The belt is designed to fit to any type and size of treated patient body area. In one preferred embodiment the belt is in touch with patient's body surface matches the curvature of patient's body. Size of the belt may be variable by stretching and/or by plugging and/or removing of one or more parts of the belt.

In another embodiment the belt may be considered as a block of at least two treatment applicators attached in optimal working distance to the patient's body. Optimal working distance may be any distance from the skin of the patient or in direct contact with the skin of the patient. Applicators may have various sizes and shapes.

One or more treatment applicators may communicate with each other and/or with one or more control units via cables, wireless and/or via connection through the belt. Transfer of the information through the cable may be based on conductive mechanism and/or via mechanism used in an optical fibers and/or as a wave guide provide transfer of different types of the energy (e.g.: sonic, electric, electro-magnetic, pressure by liquid or gas substances and/or other). The communication may provide information about locations and/or type of the applicator/applicators, treatment protocol, treatment parameters and other information. In some embodiments it is possible to provide treatment between multiple applicators, (e.g.: multiple monopolar, unipolar and/or multipolar apparatus) or focusing of some energy sources (e.g.: RF, ultrasound, light), that may improve some treatment (e.g.: removing of fatty tissue).

Large scale modularity by changing hardware and/or treatment pattern by placing of at least one applicator and/or other parts of the device, (e.g.: adding, removing, reorganization and/or changing of spacing between of at least one applicator and/or other part of the device) before and/or during the treatment allows actualization of the device and prevents obsolescence of the device. The belt may or may not contain supporting matrix. The belt may be flexible, whole or partly elastic and may be adapted to patient surface of arbitrary size and shape. This characteristic helps to provide optimal energy transfer from an applicator to the patient soft tissue. Improved contact with the patient skin or surface may decrease or prevent an edge effect, backscattering of delivered energy and/or provides better conditions for collecting feedback information. Supporting matrix may also be connected to upper side of the applicator, keep one or more applicators in touch with the patient surface, and not be in touch with the patient.

A treatment pattern creates pattern by switching between applicators and/or treatment elements providing one or more types of the therapy across the patient surface. A treatment pattern may include different types of switching sequences, and also include at least one of: a specific treatment therapy is applied; a selection of applicators and/or treatment elements applying specific treatments; timing of the applied therapy; the distance between at least two applicators; duration of the treatment therapy applied; body location where the treatment therapy applied; cycle of applying one or more specific treatment therapies.

A treatment pattern may provide information about applying one or more types of the treatment therapies and their manner (e.g.: simultaneous, sequential and/or applying of one or more treatment therapies with some overlay). A treatment pattern may simulate moving of the one or more applicators guided by an operator by switching between applicators and/or treatment elements of one or more applicators and/or one or more treatment therapies. Simulated moves may be circular, zig-zag, spiral, other geometrical pattern, scanning and/or other pattern that may be created by moving the applicator guided by operator. A treatment pattern may also be used for scanning of the patient soft tissue.

A hardware pattern is a composition of the device and placement of the parts of the device. A hardware pattern also includes placement of the applicators which is in some embodiments not limited (e.g.: in the supporting matrix, on the patient surface etc.), placement of the treatment unit, and/or other devices adjacent/at working distance to the soft tissue (which includes direct, indirect or no contact).

The belt may be a block of more than one applicator with and/or without supporting matrix and/or with or without spacing object. Location of individual applicators (optionally including different types of applicators) creates a hardware pattern. A computer and/or operator may choose several treatment therapies and procedures that can work simultaneously, with some overlay and/or sequentially during the treatment time and/or adjust one or more parameters of the procedure before and/or during the treatment.

Figure 6:
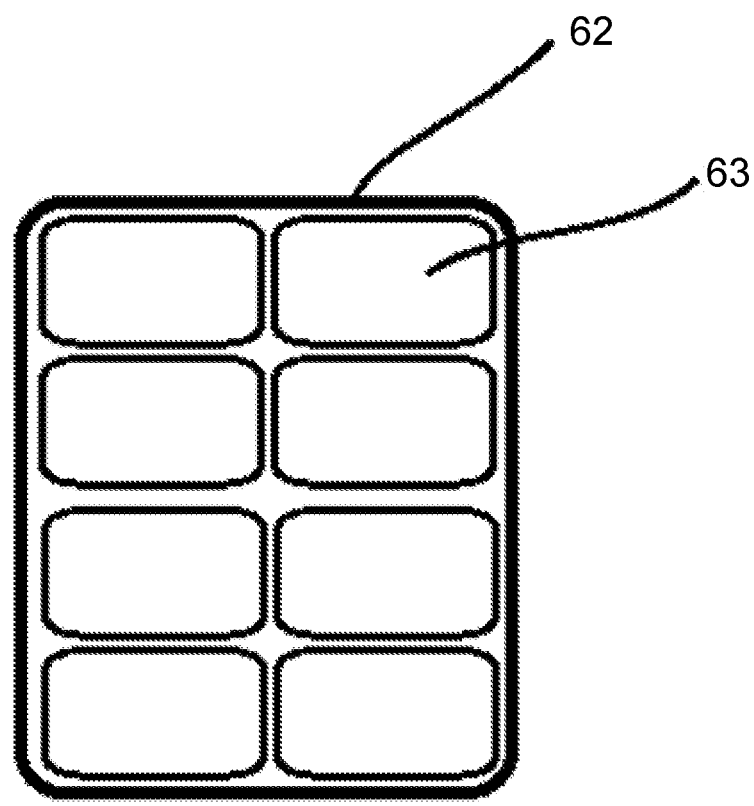
FIG. 6 is a schematic diagram of treatment elements in the applicators.

According another embodiment applicator may also create treatment pattern by switching on/off of some treatment elements included in the applicator. In FIG. 6 element number 62 is the applicator's active surface with multiple treatment elements 63. Applicator may contain different shapes of the treatment elements and number of the treatment elements in one applicator is not limited. Spacing between treatment elements may be different across the applicator's active surface. Treatment elements may also be movable during the treatment and/or spacing between treatment elements may also be variable during the time of the treatment. Switching on/off of some treatment elements during the time may be defined by protocol of the treatment procedure and may create multiple different types of the treatment pattern that may change during one treatment procedure. All of the treatment elements in one applicator may provide one therapy or in some other embodiment of the applicator, treatment elements of one applicator may provide different types of the therapies. Treatment pattern created by one applicator may also be created by moving of one or more treatment elements included in the applicator.

In another embodiment parts of the device may be attached to patient body and/or to other parts of the device by a sticky layer between contact surfaces and/or by high adhesive layer applied on one or more contacts surfaces. Contact between parts of the device and/or between one or more parts of the device and patient surface may be provided by gravitational force, by high roughness of the contact surfaces, by electric forces, by magnetic forces, by rails, by elastic, partially elastic and/or non-elastic stripes, by Lace, by Velcro, zipper, by tacks, by creating lower air pressure between contact surfaces by suction mechanism, by interaction between polar and/or non-polar group of the contact surface, by fastening mechanism described below and/or by other physical, chemical, mechanical interaction between parts of the device and/or between patient surface. Some parts of the device may also be connected to each other by individual elements of a scaffold.

The belt may include supporting matrix that can hold one or more applicators and/or its treatment elements in touch with patient's body surface and/or it may also hold one or more applicators at an optimal working distance from the patient surface. The patient surface is typically the skin of the patient. However, the patient body surface may alternatively be some spacing object e.g.: clothing worn over the skin, a sheet, pad or other thin (0.1-2 mm) covering over the skin, and/or a thicker spacing object.

Spacing object may be located between any parts of the device and/or between patient and some parts of the device. Because of mechanical, structural, physical and/or chemical properties of this spacing object, spacing object may provide and/or improve attachment of any parts of the device and/or some parts of the device and patient body surface together.

The belt may encircle the patient's torso and/or limb, and optionally including a fastening mechanism that may have various embodiments and may help to fixe applicator(s) to supporting matrix.

The supporting matrix may include fastening mechanism for attaching applicators to supporting matrix, for attaching some parts of the supporting matrix together, for attaching supporting matrix to spacing object and/or to patient's body and/or for attaching other parts of the device together. Fastening mechanism may also provide attaching one or more applicators to spacing object and/or to patient's body. Fastening mechanism may be e.g.: snap, clamp, some rails, adhesive polymer, pre-prepared holes, Velcro, zipper and/or other implemented fastening mechanisms and/or snap mechanisms) and/or may be provided by electromagnetic field, by magnetic field, by pressure lower than atmospheric pressure, by adhesive material, by interaction of chemical bounding interaction (interaction between polar and nonpolar groups) and/or others methods similar to method described above and/or other mechanisms.

The supporting matrix may contain fastening mechanism which may be permanent or removable from the supporting matrix. Position of the fastening mechanism may be variable and/or fixed before, during and/or after treatment. Fastening mechanisms may have various spacing between each other, different shapes, sizes and/or mechanism, how to be attached some of the applicators and/or how to be attached to supporting matrix and/or how to provide other types of the connection described above (based on physical, chemical and/or mechanical interaction). Fastening mechanism may be attached to supporting matrix and/or to arbitrary other part of the device at arbitrary location by similar manner as it is described above—attachment of the applicator to patient's body and/or to spacing object. Fastening mechanism may be also attached to supporting matrix and/or other parts of the device by mechanical connection.

One applicator may be attached across multiple fastening mechanisms (e.g.: applicators provide mechanical massage with movable and/or static element, RF therapy and/or other applicators provided different and/or multiple types of the therapies). It is not necessary that supporting matrix encircling whole patient torso and/or limb etc. In some embodiments applicators may be attached to both sides of the supporting matrix.

The belt may comprise applicators applied on the patient surface and/or a thin and/or a thicker spacing object and fixed by textile, polymeric and/or other strips. The strips may be at least partially elastic. The applicator(s) may be attached at the right working distance by one or more stripes located in front and/or back side of the applicator. Suitable elastic materials are elastomers or also elastic fabrics. The elastic belt material also adapts to respiratory movements and/or other movement of the patient.

The applicators may have different sizes and shapes, to improve treatment results and/or flexibility of the belt. Each applicator may be fixed to supporting matrix at arbitrary position e.g.: by inserting an applicator into the pocket in the support matrix, by Velcro and loop tape, by one or more magnets, by tacks or fasteners, fastening straps and/or by other fastening mechanism 51 as may be seen in FIG. 5 and/or by other manner described above.

The supporting matrix may be attached to the patient by different way described above and/or by encircling patient body and connect some parts of supporting matrix to each other and/or by external positive pressure acting on supporting matrix in direction to the patient surface. Supporting matrix may be designed as one or combination of more pieces where at least one piece has elastic properties. Supporting matrix may be designed as elastic clothes (e.g. elastic trousers, sleeves, shirt etc.) to fix one or more applicators at optimal location on the patient body and/or at optimal working distance with the patient body at the right position. Supporting matrix may be fixed at specific body location of the patient body and/or may be movable along the patient body.

Some parts of the supporting matrix may be created of flexible, elastic and/or rigid materials e.g.: polymeric materials, ceramics, textile materials, conductive parts and/or other materials. The supporting matrix may be at least partially flexible and/or elastic to provide improved contact with the patient body and/or set appropriate working distance for one or more applicators.

The support matrix may also contain apertures of different sizes and shapes. The support matrix may contain cooling/heating elements, massage elements that may move across the belt area and/or one or more sensors. In some embodiment mechanism for moving with attached applicators and/or other part of the belt may be provided according defined pattern. A track or path for the applicator may be created by rails (e.g.: applicator may be moved along them by mechanical forces based on pressure and/or tensile forces) and/or by a path created from conductive elements and applicators may be moved along them by electric, magnetic and/or electromagnetic forces.

Moving of one or more applicators and/or other parts of the belt across the patient body may also be provided by moving of the supporting matrix. Move of the supporting matrix may be provided by expansion and/or shrinking of some parts of the supporting matrix and/or by moving with the supporting matrix along the spacing object (e.g. by mechanic, electric, magnetic and/or combination of these forces) and/or by attaching supporting matrix to an another movable parts of the device (e.g.: mechanical arm, construction on rails).

Figure 5:
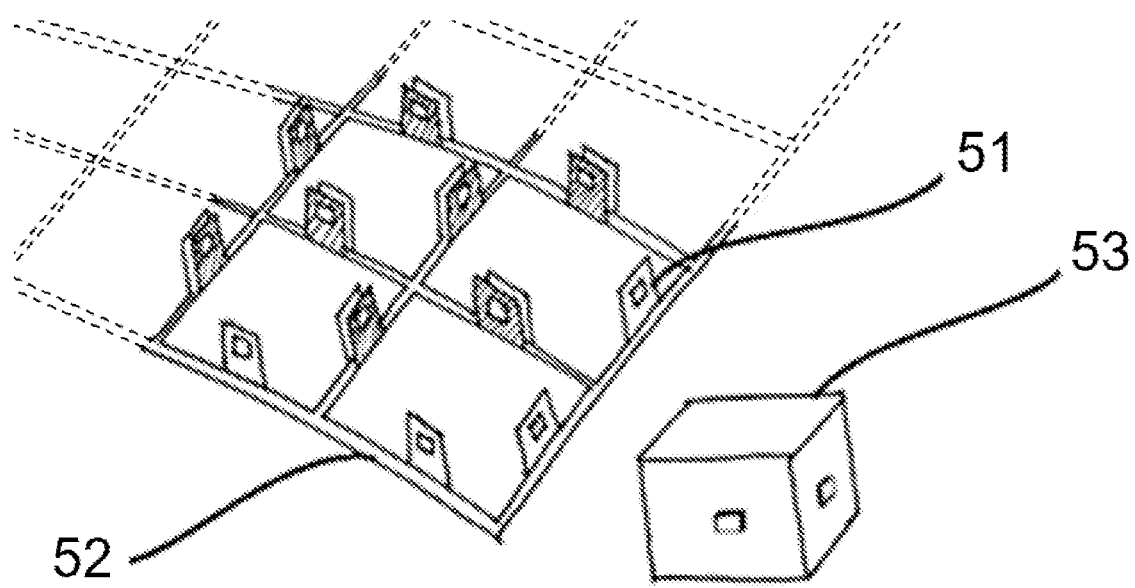
FIG. 5 is a partial perspective view of an embodiment of the belt providing hardware pattern.

The supporting matrix may have several embodiments. One of such embodiment is depicted in FIG. 5 where the support matrix consists of guiding scaffold 52, with the one or more applicators 53 attachable to the scaffold 52 by fastening mechanism 51. The supporting matrix may include conductive parts that may provide communication between applicators, communication between applicators and central control unit and/or communication between at least one applicator and treatment unit. Conductive parts in the supporting matrix may also provide power supply to the applicator(s). Applicator may also include one or more rechargeable batteries as a source of energy. These batteries may be recharged through the supporting matrix and/or through the spacing object.

In another embodiment belt may be a flexible textile and/or polymeric sheet. This sheet may contain conductive elements that may provide communication, power supply, determine of one or more applicators location and type, contact with the supporting matrix and/or patient surface, provide information about treatment protocol as was mentioned above and/or other features. In some embodiments supporting matrix may also include cooling and/or heating components. This embodiment of the belt may also include spacing object.

As a result, so-called plug and play methods may be used to modify hardware pattern of the applicators attached to patient and/or to supporting matrix (sorting and/or choosing of the applicators). This plug and play method provides a large scale of modularity. The supporting matrix also may recognize which applicator is positioned or fixed in which slot in the supporting matrix and the control unit may assign and/or accept predefined treatment protocols. Recognition of the applicator may also be provided by one or more central control units and/or by any other one or more control units. Localization of the applicator may be provided by some specific sensors described below.

Figure 4:
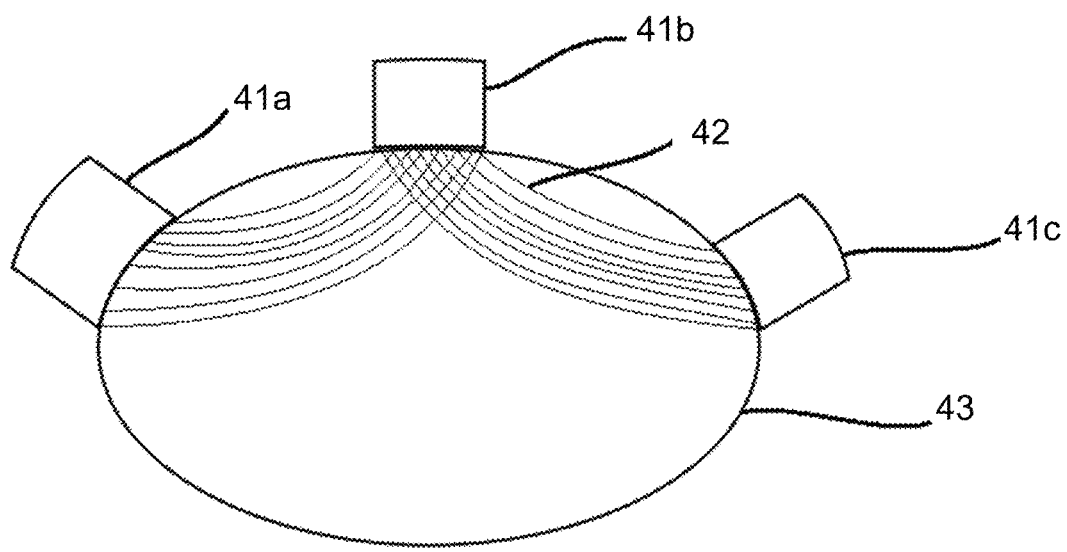
FIG. 4 is schematic representation of cooperation multiple applicators across the patient body.

Several applicators may cooperate with each other. FIG. 4 describes cooperation of multiple applicators 41a, 41b, 41c that may provide some treatment therapy (e.g. multipolar RF therapy symbolized by field lines 42 and/or others) to the patient 43. Cooperation of multiple units may be used for different therapies (e.g.: RF, ultrasound, light, massage, cooling/heating, electrotherapy, magneto-therapy and/or other therapies) in order to provide bipolar and/or multipolar treatment across large patient area, better targeting of delivered therapy, better focusing of delivered signal, creating of some gradient in the soft tissue (e.g. thermal gradient, etc.), better homogeneity of provided therapy across large patient area and/or volume of the soft tissue.

Cooperation of multiple applicators and/or treatment elements may enlarge treatment variability (e.g. treatment depth, focusing), since the electrode of each applicator and/or treatment element may represents one pole of multipolar treatment.

RF energy and electrostimulation may help with drug delivery through the skin of the patient. The present system and method may also involve an application of the substance and/or mixture of substances causing a physiological change in the body of the patient. In addition, the mixture (e.g. green tea extract) may include not yet characterized substances. Application of the substance and/or mixture of the substances may provide patient with a more comfort and/or improve the performance of the system.

In one embodiment, the substance may modulate normal metabolism and/or basal metabolism rate of the patient's body. It may provide acceleration to the metabolism related to the apoptotic cells. Such substances may include alkaloids (e.g. xanthines), antithyroid agents, metformin, octreotide and a like.

Substances may modulate efferocytosis, which is the process by which dying cells are removed by phagocytic cells. This may provide acceleration and improvement in the dead cells removal. Such substance may include prostaglandins and their analogues, modified lipids (e.g. lysophosphatidylserine, lipoxins, resolvins, protectins and/or maresins), lipoprotein lipase inhibitors, nitric oxide secretion stimulators, alkaloids (e.g. xanthines), aspirin, antioxidants (e.g. ascorbic acid), derivatives of carbohydrates and a like.

Delivered substances may modulate lipolysis rate. In case of application of electromagnetic energy to the adipocytes it may provide another way of removal of the adipose cells, which may be independent from the treatment method. Such substances may include terpens (e.g. forskolin), catecholamins, hormons (e.g. leptin, growth hormone and/or testosterone), alkaloids (e.g. synephrin), phosphodiesterase inhibitors (e.g. xanthins), polyphenols, peptides (e.g. natriuretic peptides), amino acids and a like.

Delivered substances may modulate hydration of the patient. Such substances and/or mixtures may include xanthines, lactated Ringer's solution, physiological saline solution and a like.

Delivered substances may modulate circulatory system of the patient. This may provide the higher rate of blood circulation, which may result in faster cooling rate of the skin. Such substances may include catecholamines, alkaloids (e.g. xanthins), flavanols and a like.

Delivered substances may induce the reversible decrease or absence of sensation in the specific part of the patient's body. This may provide a certain level of comfort to heat-sensitive patient. Such substances may include lidocaine, benzocaine, menthol and a like.

Delivered substances may shield the electromagnetic radiation from the patient's body. This effect may be used for protection of sensitive parts of the human body. Such substances may include mixture containing metal nanoparticles, mixture containing polymer particles and a like.

Delivered substances may modulate the effect the electromagnetic radiation applied on the patient's body. This may accelerate removal of the desired tissue, for example by heating of the tissue and/or increasing the effect of the applied radiations. Such substances may include carotens, chlorophylls, flavanols and a like.

Delivered substances may be used singularly or in various combinations with at least one suitable substance, which may be not listed as an example. For example, lidocain providing a local anesthesia may be combined with prilocaine to provide improved effect. The substance and/or mixture of the substances may be administered in different time related to the tissue treatment. It may be administered before the treatment, during the treatment and after the treatment.

Delivered substances may be administered in order of seconds, hours or even days to accumulate in the desired tissue. The subsequent application of the electromagnetic radiation may modulate the action of the accumulated substance and/or be modulated by the action of the substance. According the example of this embodiment, the chromophore may be accumulated in the treated tissue, such as adipocytes, before the treatment. Chromophore may then absorb electromagnetic radiation and heat the tissue nearby. Presented active agents or in this text called substances may have significant influence to treatment therapy as is described in U.S. Provisional Application No. 62/331,060 incorporated herein by reference.

Delivered substances may be applied to the particular part of the tissue, which is not a target of the therapy. It may change the blood perfusion, conductivity, hydration and other characteristics of the non-targeted tissue. In another embodiment, the targeted tissue may be adipose tissue and the non-targeted tissue may be any other soft tissue.

Substances mentioned above may by delivered to patient's body before, during and/or after treatment session.

The present methods and devices provide for improving skin viability, skin and body rejuvenation, skin tightening, scar removing, spider veins removing, restoring and restructuring collagen in the soft tissue body shaping (e.g. butt lifting, breast lifting etc.), body contouring, circumferential reduction, cellulite removing, adipose tissue reduction, adipose tissue removing, muscle relaxation, relaxation of muscle tone, muscle building, muscle strengthening, treating and stimulating pelvic floor tissue and adjacent muscles, remodeling of outer part of genitals treat sexual dysfunctions, treat or reduce incontinence problems, accelerate neocolagenesis, improving blood flow, lymph flow, stimulation of lymph nodes, movement of the vessels, bruising removing, reduce swelling, enhancing vitamin D metabolism, restoring nerve signal transfer, accelerate body metabolism, accelerate cell metabolism, pigmentation disorders, tattoos removal, stress relive, micro-dermal abrasion, hair removal, shortening of recovery time after injury and/or other skin and body affliction using application of RF energy and electrical stimulation to the soft tissue.

Special treatment may be targeted to areas near human genitals (e.g.: improve pigment homogeneity, downsizing of pubic lips and/or other target area) and/or treatment may be targeted inside of the human cavities as anus or vagina in order to treat pelvic floor and/or other areas inside the patient's body.

During treatment of human cavities at least part of the applicator and/or treatment energy source may be inserted inside of human cavity and may be there placed stationary or may be moved with circular and/or linear moves according any Cartesian coordinate.

According other embodiments an applicator is used for treating of human cavities and it may also be designed to treat outer side of genitals simultaneously with treating inside area of human cavity.

Part of an applicator for human cavity treatment may have a changeable volume. Such part may be inflated, deflated and/or stretch in order to provide optimal contact with soft tissue in the human cavity and so provide optimal energy transfer from at least one treatment energy source to the patient's soft tissue. Changing volume of at least part of the applicator may be by inflating/deflating such part with air or liquid and/or such volume changing applicator's part may change its volume and/or shape by properties of the material based on humidity or temperature changes and/or by changing geometry inside of the applicator caused by electromotor.

Treatment energy source providing electrotherapy in human cavity may be located on or near the applicator's surface and treatment energy source providing RF therapy may be located inside and or on the surface of the applicator.

An applicator and treatment effects, treated tissues and/or other features are described in U.S. patent application Ser. No. 15/478,943, incorporated herein by reference.

One treatment session may last between 1 minute to 120 minutes, or between 5 minutes to 40 minutes, or between 10 minutes to 30 minutes or between 10 to 20 minutes Recommended delay between two treatment sessions may be influence by provided intensities of delivered energy to the patient's body, provided therapies and/or provided active substances. Recommended delay between two treatment sessions may be in range 1 hour to 20 days, or in range 8 hours to 14 days, or in range 24 hours to 7 days.

The device and method may be used for treating patients for patients with BMI in range between 18 to 40 and/or with subcutaneous adipose tissue layer thickness in range between 1 mm to 15 cm, or between 3 mm to 7 cm, or between 3 mm to 3 cm.

Thus, novel methods and devices have been shown and described. Various changes and substitutions may of course be made without departing from the spirit and scope of the invention. The invention, therefore, should not be limited, except by the following claims, and their equivalents.

The invention claimed is:

1. A method for aesthetic tissue treatment of a patient by radiofrequency waves and electric current, comprising:
    attaching at least one applicator into a stationary position in contact with a body part of the patient,
    wherein the applicator has at least one electrode, and wherein the applicator comprises a flexible material adaptable to a body surface of the patient;
    providing an electric current and radiofrequency waves to the body part by the at least one electrode;
    applying the electric current having a frequency in a range of 0.1 Hz to 200 Hz and causing a muscle contraction within the body part; and
    heating adipose tissue within the body part with the radiofrequency waves.

2. The method of claim 1, wherein the body part comprises an abdomen, a buttock, or an arm of the patient.

3. The method of claim 2, wherein the electric current and the radiofrequency waves are provided within the same treatment.

4. The method of claim 3, further comprising providing the radiofrequency waves with a flux density in a range from $0.01$ mW·mm$^{-2}$ to $2$ W·mm$^{-2}$.

5. The method of claim 4, further comprising positioning a gel between the applicator and the body surface.

6. The method of claim 4, further comprising providing the electric current simultaneously with the radiofrequency waves.

7. The method of claim 4, further comprising providing the electric current sequentially with the radiofrequency waves.

8. A method for aesthetic tissue treatment of a patient by radiofrequency waves and electric current, comprising:
    attaching an applicator into a stationary position in contact with a body part of the patient,
    wherein the applicator has at least one flexible electrode adaptable to a body surface of the patient;

providing an electric current and radiofrequency waves to the body part by the at least one flexible electrode;

applying the electric current having a frequency in a range of 0.1 Hz to 200 Hz and causing a muscle contraction followed by a muscle relaxation within the body part; and heating adipose tissue within the body part with the radiofrequency waves.

9. The method of claim 8, further comprising switching the at least one flexible electrode between providing the radiofrequency waves and the electric current during the treatment.

10. The method of claim 9, further comprising positioning a gel between the applicator and the body surface.

11. The method of claim 10, further comprising providing a treatment protocol from a control unit.

12. The method of claim 11, further comprising modulating an intensity and the frequency of the provided electric current.

13. The method of claim 12, wherein the applicator is attached in the stationary position by a belt.

14. A method for aesthetic tissue treatment of a patient by radiofrequency waves and electric current, comprising:

attaching a plurality of electrodes into a stationary position in contact with a body part of the patient;

wherein the plurality of electrodes comprises a flexible material adaptable to a body surface of the patient;

providing an electric current and radiofrequency waves to the body part by the plurality of electrodes;

applying the electric current having a frequency in a range of 0.1 Hz to 200 Hz to provide an analgesic effect to the body part and cause a muscle contraction within the body part; and heating the adipose tissue within the body part with the radiofrequency waves.

15. The method of claim 14, wherein the electric current and the radiofrequency waves are provided within the same treatment.

16. The method of claim 14, wherein a voltage between two electrodes of the plurality of electrodes is in a range of 0.8 V to 100 V.

17. The method of claim 14, wherein a frequency of the radiofrequency waves is in a range of 100 kHz to 3500 kHz.

18. The method of claim 14, further comprising controlling an operation of the plurality of electrodes in groups comprising of at least two electrodes from the plurality of electrodes.

19. The method of claim 14, further comprising providing the electric current simultaneously with the radiofrequency waves.

20. The method of claim 14, further comprising providing the electric current sequentially with the radiofrequency waves.

* * * * *

UNITED STATES PATENT AND TRADEMARK OFFICE
CERTIFICATE OF CORRECTION

| | | |
|---|---|---|
| PATENT NO. | : 11,458,307 B2 | Page 1 of 1 |
| APPLICATION NO. | : 16/727458 | |
| DATED | : October 4, 2022 | |
| INVENTOR(S) | : Schwarz | |

It is certified that error appears in the above-identified patent and that said Letters Patent is hereby corrected as shown below:

In the Claims

In Column 25, Claim 14, Line 25, delete "patient;" and insert -- patient, --, therefor.

In Column 26, Claim 14, Line 7, delete "the" after "heating".

In Column 26, Claim 18, Line 19, delete "of" after "comprising".

Signed and Sealed this
Ninth Day of May, 2023

*Katherine Kelly Vidal*

Katherine Kelly Vidal
*Director of the United States Patent and Trademark Office*